United States Patent [19]

Green et al.

[11] 4,124,707

[45] Nov. 7, 1978

[54] 7α-HALOGENO-3,20-DIOXO-1,4-PREGNADI-ENES, METHODS FOR THEIR MANUFACTURE, THEIR USE AS ANTI-INFLAMMATORY AGENTS, AND PHARMACEUTICAL FORMULATIONS USEFUL THEREFOR

[75] Inventors: Michael J. Green, Kendall Park; Ho-Jane Shue, Belleville, both of N.J.

[73] Assignee: Schering Corporation, Kenilworth, N.J.

[21] Appl. No.: 848,856

[22] Filed: Nov. 7, 1977

Related U.S. Application Data

[63] Continuation-in-part of Ser. No. 753,256, Dec. 12, 1976, abandoned.

[51] Int. Cl.$^2$ .................... C07J 5/00; A61K 31/58

[52] U.S. Cl. .................... 424/241; 260/239.55 D; 260/397.1; 260/397.4; 260/397.45; 260/397.47; 424/243

[58] Field of Search .................... 260/397.45; 424/241

[56] References Cited

U.S. PATENT DOCUMENTS 2,819,264   1/1958   Gould et al. .................... 260/239.55

*Primary Examiner*—Elbert L. Roberts
*Attorney, Agent, or Firm*—Mary S. King

[57] ABSTRACT

Novel 3,20-dioxo-7α-halogeno-1,4-pregnadienes are described and their use as anti-inflammatory agents. Preferred are 7α-bromo- and 7α-chloro- derivatives, particularly 7α-bromo- and 7α-chloro-1,4-pregnadienes-11β,17α,21-triol-3,20-dione 17,21-dihydrocarboncarboxylates, the 16-methyl and 16-methylene derivatives thereof being particularly valuable as topical anti-inflammatory agents.

29 Claims, No Drawings

7α-HALOGENO-3,20-DIOXO-1,4-PREGNADIENES, METHODS FOR THEIR MANUFACTURE, THEIR USE AS ANTI-INFLAMMATORY AGENTS, AND PHARMACEUTICAL FORMULATIONS USEFUL THEREFOR

CROSS REFERENCE TO RELATED APPLICATION

This application is a continuation-in-part of copending application Ser. No. 753,256 filed Dec. 12, 1976 now abandoned.

FIELD OF INVENTION

This invention relates to novel compositions-of-matter, methods for the manufacture thereof, pharmaceutical formulations thereof and the method of using said formulations in the treatment and control of inflammatory conditions.

More specifically, this invention relates to novel 7-halogeno-3,20-dioxo-1,4-pregnadienes, pharmaceutical formulations thereof, and their use in the treatment and control of inflammatory conditions.

In particular, this invention relates to novel 7α-halogeno-1,4-pregnadiene-11β,17α,21-triol-3,20-dione 17,21-dihydrocarboncarboxylates, particularly 16-methyl and 16-methylene derivatives thereof, to pharmaceutical formulations thereof, and their use in the treatment and control of inflammation when applied topically.

DESCRIPTION OF THE PRIOR ART

Described in the art are 7-chloro-17α-acetoxy-6-dehydroprogesterones (R. W. Guthrie et al, J. Med. Chem., Vol. 16, p. 65 (1973)) and 7α-chloro-A-norprogesterone (P. A. Diassi et al, J. Med. Chem., Vol. 10, 551 (1967)). Both the foregoing publications disclose that the introduction of the 7-chloro atom greatly diminished the progestational activity of the corresponding 7-unsubstituted precursor. Additionally, P. A. Diassi et al teaches that no 7α-chloro-4-dehydro-3-one has ever been reported to be obtained by either DDQ-hydrogen chloride treatment of a 4-dehydro-3-one or by addition of hydrogen chloride to 4,6-bis-dehydro-3-ones. P. A. Diassi et al postulate that while said structures may exist in situ, they are unstable and convert to a 4,6-bis-dehydro-3-one structure when attempts are made to isolate said 7α-chloro-4-dehydro-3-one.

By our invention, we have developed methods of preparing 3,20-dioxo-7α-halogeno-6,7-dihydro-1,4-pregnadienes, and have discovered these compounds are, in general, valuable anti-inflammatory agents, particularly the 7α-chloro and 7α-bromo-derivatives of 16α-methyl-1,4-pregnadiene-11β,17α,21-triol-3,20-dione 17,21-dihydrocarboncarboxylates which are potent topical anti-inflammatory agents possessing enhanced activity over that exhibited by the corresponding 7-unsubstituted precursor.

DESCRIPTION OF THE COMPOSITION-OF-MATTER ASPECT OF THE INVENTION

The composition-of-matter aspect of this invention resides in the concept of a 7α-halogeno-3,20-dioxo-1,4-pregnadiene having corticoid activity, particularly 7α-halogeno-1,4-pregnadiene-11β,17α,21-triol-3,20-dione 17,21-dihydrocarboncarboxylates, useful topical anti-inflammatory agents.

Typical 7α-halogeno compounds of this invention include 3,20-dioxo-7-halogeno-1,4-pregnadienes of the following formula I:

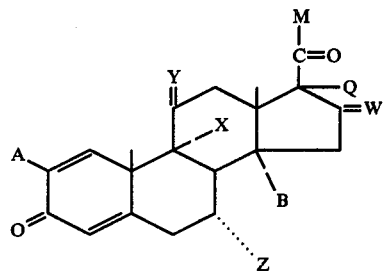

wherein A is hydrogen, and provided Y is (H,βOH), chlorine, fluorine or methyl;

B is hydrogen or, together with Q, is a 14α,17α-alkylidenedioxy derivative;

X is a member selected from the group consisting of hydrogen and halogen having an atomic weight less than 100;

Y is a member selected from the group consisting of (H,H) provided X is hydrogen, oxygen, (H,βOH), (H,βOCOH): and (H,β-halogen) provided X is chlorine or bromine, said β-halogen having an atomic weight of less than 100 and being at least as electronegative as X;

Z is fluorine, chlorine, bromine and iodine;

Q is a member selected from the group consisting of hydrogen provided W is a member selected from the group consisting of (H,H), and (H, lower alkyl); chlorine; bromine; and OV wherein V is a member selected from the group consisting of hydrogen and an acyl radical of a hydrocarboncarboxylic acid having up to 12 carbon atoms or of benzoic acid substituted by a halogen or methoxy group;

W is a member selected from the group consisting of (H,H); (H, lower alkyl); (H,α-OV₁) wherein V₁ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, and isonicotinic acid; =CHT wherein T is a member selected from the group consisting of hydrogen, lower alkyl, fluorine and chlorine; and W and Q taken together is a member selected from the group consisting of 16α,17α-lower alkylidenedioxy; 16α,17α-cycloalkylidenedioxy; the grouping

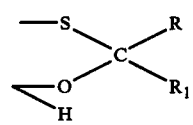

wherein R and R₁ are lower alkyl; and the grouping

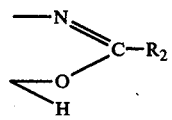

wherein R₂ is lower alkyl or phenyl;

M is a member selected from the group consisting of —OR₃ when Q is O-acyl, R₃ being lower alkyl or halogeno lower alkyl; —CHO, acetals, hemiacetals and acylals thereof; —COOR₄ wherein R₄ is a hydrocarbon radical having up to 12 carbon atoms; —CH₂G wherein G is a member selected from the group consisting of hydrogen, halogen having an atomic weight of less than 100; OV₂ wherein V₂ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, isonicotinic acid, phosphoric acid and mono- and dialkali, and alkaline earth metal salts thereof; and OV₂ together with OV is a member selected from the group consisting of alkylidenedioxy, alkylorthoalkanoate and alkylorthoarylcarboxylates;

When W is hydrogen, the D-homo analogs thereof.

Alkyl groups included within the definition of W, T, R, R₁, R₂, R₃ and R₄ are preferably lower alkyl, particularly those having up to four carbon atoms such as methyl, ethyl, n-propyl, isopropyl, n-butyl, sec.-butyl, and tert.-butyl, although higher homologs such as pentyl and hexyl fall within the scope of this invention.

Other hydrocarbon groups contemplated for the substituent R₄ are aliphatic groups having up to 12 carbon atoms including straight and branched chain alkyl groups and cycloaliphatic groups which can be saturated or unsaturated, substituted or unsubstituted; aryl, aralkyl, and alkaryl groups. Of the foregoing, preferred are alkyl groups having up to four carbon atoms. Typical unsaturated aliphatic groups are vinyl, propenyl, propynyl, and butenyl; typical cycloalkyl groups are cyclopropyl, cyclopentyl, cyclohexyl, cyclopentenyl, and p-dicyclohexyl; typical aryl groups are phenyl, α-naphthyl, and p-diphenyl; typical alkaryl groups are tolyl, xylyl, and symdiethylphenyl; and typical aralkyl groups are benzyl, phenethyl and diphenylmethyl.

As used in the specification and claims of this application, the term "acyl" denotes a radical derived from an acid by removal of a hydroxyl group; e.g. acetyl is the acyl radical of acetic acid, benzenesulfonyl is the acyl radical of benzenesulfonic acid, and benzoyl is the acyl radical of benzoic acid.

The acyl radicals of the compounds of this invention as defined by V, V₁ and V₂ in formula I hereinabove include those derived from hydrocarboncarboxylic acids having up to 12 carbon atoms which may be saturated, unsaturated, straight chain or branched chain, aliphatic, cyclic, cyclic-aliphatic, aromatic, aryl-aliphatic, or alkyl-aromatic, and may be substituted by hydroxy, alkoxy containing from 1 to 5 carbon atoms or by a halogen. Typical ester groups of the 7-halogeno-3,20-dioxo-1,4-pregnadienes of our invention are thus derived from hydrocarboncarboxylic acids such as alkanoic acids exemplified by formic, acetic, propionic, trimethylacetic, butyric, isobutyric, valeric, isovaleric, caproic, tert.-butyl-acetic, enanthic, caprylic, capric, cyclopentylpropionic, undecylic, lauric, and adamantanecarboxylic acids; substituted alkanoic acids such as phenoxyacetic, trifluoroacetic, and β-chloropropionic acids; aromatic and substituted aromatic acids including benzoic, toluic, p-chlorobenzoic, p-fluorobenzoic, p-methoxybenzoic, and 3',5'-dimethylbenzoic acids; arylalkanoic acids such as phenylacetic, phenylpropionic, and β-benzoylamino-isobutyric acids; unsaturated acids such as acrylic and sorbic acids; and dibasic acids such as succinic, tartaric, phthalic and benzene disulfonic acids.

The term "lower alkanoyloxy" is contemplated as including acid radicals of lower alkanoic acids having preferably up to 8 carbon atoms such as radicals obtained from acetic, propionic, butyric, valeric, caprylic, caproic, tert.-butylacetic acid and the like.

The halogens at C-9 as defined by X in above formula I are bromine, chlorine, and preferably fluorine. The halogens at C-21 as defined by G in above formula I are fluorine, chlorine and bromine.

The alkylidene groups contemplated in the compounds of our invention are preferably lower alkylidenes, i.e. hydrocarbon radicals having preferably up to four carbon atoms including radicals such as methylene, ethylidene, n-propylidene, isopropylidene, n-butylidene, and sec.-butylidene and the like. The 16-lower alkylidene derivatives of this invention (i.e. when W in the above formula I is =CHT) are double bonded to the D ring at C-16. The 16α,17α-alkylidenedioxy derivatives have the alkylidene terminal bonds attached to different oxygen atoms, i.e. to the oxygens at C-16 and C-17 in the case of the 16α,17α-alkylidenedioxy derivatives, to oxygens at C-17 and C-21 in the case of the 17α,21-alkylidenedioxy derivatives, and to oxygens at C-14 and C-17 in the case of the 14α,17α-alkylidenedioxy derivatives.

Of the pregnadieno (17,16α-D)-1,3-oxythiolanes of our invention (i.e. compounds of formula I wherein W and Q together form the grouping

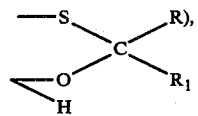

preferred are those wherein R and R₁ are both methyl groups.

Of the 5'βH-pregnadieno(17,16-d)oxazole-3,20-diones of our invention (i.e. compounds of formula I wherein W and Q together form the grouping

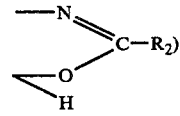

preferred are those wherein R₂ is methyl.

The physical embodiments of the 7α-halogeno-3,20-dioxo 1,4-pregnadienes of formula I are characterized by being crystalline solids, usually white to off-white in color, which are insoluble in water (with the exception of alkali metal salts of esters such as the hemisuccinate and phosphate esters thereof) and soluble in most organic solvents, particularly in acetone, dioxane, dimethylformamide, and dimethylsulfoxide, although of limited solubility in non-polar solvents such as dialkyl ethers and alkyl hydrocarbons.

The 7α-halogeno-1,4-pregnadienes are preferably kept at cool temperatures (e.g. 0° to 5° C) when stored for long periods of time to minimize decomposition to the corresponding 1,4,6-pregnatriene starting compounds. For short term storage, the 7α-chloro derivatives are relatively stable up to 100° C; however, the 7α-bromo derivatives ought be kept below 55° C.

In general, the 3,20-dioxo-7α-halogeno-1,4-pregnadienes of our invention, particularly those of formula I wherein G is hydroxy, acyloxy, or together with Q is a 17α,21-alkylidenedioxy, exhibit corticosteroid activity. Of these, those which have halogens at both C-9 and C-11 or those which have an oxygen function at C-11 and a halogen or hydrogen at C-9, possess glucocorticoid activity and are particularly valuable as anti-inflammatory agents. Of the foregoing, preferred anti-inflammatory agents (particularly when administered topically) are 3,20-dioxo-7α-halogeno-1,4-pregnadiene-17α,21-diols of formula II and esters thereof having an 11β-hydroxyl function, particularly those unsubstituted at C-9.

The 17,21-desoxy-, 17-hydroxy-21-desoxy- and 17-acyloxy-21-desoxy- derivatives of formula I, while exhibiting anti-inflammatory activity, are more valuable as progestational agents.

Of the 7-halogeno-3,20-dioxo-1,4-pregnadienes of formula I, preferred are the 7α-chloro and 7α-bromo derivatives.

Compounds of our invention which are particularly useful as topical anti-inflammatory agents are the 7α-bromo and 7α-chloro compounds of formula I having a cortical side chain at C-17, (i.e. compounds of formula I wherein M is $CH_2OV_2$ and Q is OV) and ester derivatives thereof, particularly compounds unsubstituted at C-2, C-9 and C-14. Of these, those compounds substituted at C-16 by a lower alkyl group (particularly a 16-methyl group) (e.g. 16α-methyl), or by a 16-methylene group, exhibit excellent topical anti-inflammatory activity superior to the topical anti-inflammatory activity of the corresponding 7-unsubstituted derivatives of formula I. These particularly valuable compounds of our invention are 7α-halogeno-3,20-dioxo 1,4-pregnadienes of following formula II:

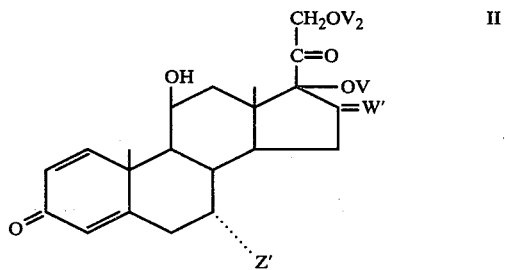

wherein Z' is chlorine or bromine;
W' is (H,CH_3) or =CH_2;
V and $V_2$ are each hydrogen or an acyl radical of a hydrocarboncarboxylic acid having up to 12 carbon atoms.

The compounds of formula II wherein V alone or both V and $V_2$ are hydrogen atoms are valuable mainly as intermediates in preparing the preferred 17-mono- and 17,21-diester derivatives.

Of the compounds of formula II, particularly useful topical anti-inflammatory agents are those wherein V and $V_2$ are acyl radicals of hydrocarboncarboxylic acids having up to 8 carbon atoms, particularly the 17-propionate, 17-n-butyrate and 17 benzoate derivatives which exhibit high topical anti-inflammatory activity with a minimum of systemic corticoid effects. When administered topically or systemically, it has been discovered that the ester group at C-17 has a much greater effect on the topical anti-inflammatory activity of the compounds of our invention than the ester group at C-21 so that the topical anti-inflammatory activity of a 17,21-dipropionate ester derivative of formula II will not be changed to any great extent by the presence at C-21 pf other hydrocarboncarboxylic esters. The 16α-methyl-17-mono- and 17,21-diacyl-derivatives of formula II are most valuable having greatly enhanced topical activity over that possessed by the corresponding 7-unsubstituted analogs.

The superior topical activity of the preferred 3,20-dioxo-7α-halogeno-1,4-pregnadienes of formula II, particularly of the 16α-methyl derivatives, are demonstrated by pharmacological tests in animals. Thus, for example, when tested in mice by a modification of the croton oil induced ear edema test (G. Tonelli et al, Endocrinology 77:625–634 (1965)), 7α-bromo-16α-methyl-1,4-pregnadiene-11β,17α,21-triol-3,20-dione 17-benzoate 21-acetate exhibits topical activity about twice that of betamethasone dipropionate (i.e. 9α-fluoro-16β-methyl-1,4-pregnadiene-11β,17α,21-triol-3,20-dione 17,21-dipropionate) with only a fraction of the systemic effect following topical application. Additionally, when tested in mice by a modification of the skin atrophy test E. G. Weirich and J. Longauer (Res. Exp. Med. 163, 229 (1974)), the foregoing 7α-bromo- compound of our invention shows markedly lower skin atrophy potency than betamethasone dipropionate. Moreover, 7α-bromo-16α-methyl-1,4-pregnadiene-11β,17α,21-triol-3,20-dione 17-benzoate 21-acetate shows great dissociation of local from systemic effects when injected locally in the rat and has minimal glucocorticoid activity when administered orally to both mice and rats.

In similar manner, when tested by the above described tests in animals, other 7αhalogeno-1,4-pregnadienes of formula II, e.g. 7α-chloro-16α-methyl-1,4-pregnadiene-11β,17α,21-triol-3,20-dione 17,21-dipropionate and the corresponding 7α-bromo- derivative, exhibit high topical anti-inflammatory activity coupled with low systemic effects following topical application and low skin atrophy as well as low parenteral and oral glucocorticoid activity.

Preferred compounds of formula II include:
the 21-acetate, 21-propionate, 21-n-butyrate, 21-isobutyrate and the 21-valerate ester derivatives of 7α-chloro-16α-methyl-1,4-pregnadiene-11β,21-triol-3,20-dione 17-propionate, and the 21-acetate, 21-propionate, 21-n-butyrate and 21-isobutyrate ester derivatives of 7α-bromo-16α-methyl-1,4-pregnadiene-11β,17α,21-triol-3,20-dione 17-propionate;

the 21-acetate, 21-propionate, and 21-n-butyrate ester derivatives of 7α-bromo-16αmethyl-1,4-pregnadiene-11β,17α,21-triol-3,20-dione 17-n-butyrate, and the 21-acetate, 21-propionate and 21-n-butyrate ester derivatives of 7α-chloro-16α-methyl-1,4-pregnadiene-11β,17α,21-triol-3,20-dione 17-n-butyrate;

the 21-acetate, 21-propionate, 21-n-butyrate and 21 benzoate ester derivatives of 7α-chloro-16α-methyl-1,4-pregnadiene 11β,17α,21triol-3,20-dione 17-benzoate, and the corresponding 7α-bromo derivatives.

Of the foregoing, particularly valuable are 7α-chloro-16α-methyl-1,4-pregnadiene-11β,17α,21-triol-3,20-dione 17,21-dipropionate and the corresponding 7α-bromo-derivative and 7α-bromo-16αmethyl-1,4-pregnadiene-11β,17α,21-triol-3,20-dione 17-benzoate 21-acetate, all of which have high topical and local anti-inflammatory activity coupled with low systemic effects following topical application, and low skin atrophy as well as low parenteral and oral glucocorticoid activity.

Other compounds of formula II include:

7α-chloro-16α-methyl-1,4-pregnadiene-11β,17α,21-triol-3,20-dione 17-valerate 21-acetate, and the corresponding 7α-bromo-derivative;

7α-chloro-16α-methyl-1,4-pregnadiene-11α,17α,21-triol-3,20-dione 17-isobutyrate 21-acetate and the corresponding 7α-bromo-derivative thereof;

7αchloro-16α-methyl-1,4-pregnadiene-11α,17α,21-triol-3,20dione and the 21-acetate, 21-benzoate, 21-pivalate, 17-propionate and 17-valerate thereof and the corresponding 7α-bromo-derivative;

the 16α-methyl epimers of the above-named 16α-methyl derivatives such as the 21-acetate, the 17,21-dipropionate, the 17-propionate 21-n-butyrate, the 17-propionate 21-acetate, the 17-benzoate 21-acetate of 7α-chloro-16β-methyl-1,4-pregnadience 11β,17α,21-triol-3,20-dione and of the corresponding 7α-bromo-derivative thereof; and 16-methylene derivatives such as 7α-chloro-16-methylene-1,4-pregnadiene-11α,17α,21-triol-3,20-dione 17,21-dipropionate.

In addition to the preferred compounds of formula II, our invention includes 7α-halogeno-3,20-dioxo-1,4-pregnadienes of formula I such as:

9α-halogeno derivatives of the compounds of formula II, particularly the 9α-fluoro and 9α-chloro derivatives thereof;

9α,11β-dihalogeno pregnadienes of formula I (i.e. wherein X and Y are both halogen) such as:

7α,9α,11β-trichloro-16α-methyl-1,4-pregnadiene-17α,21-diol-3,20-dione 17,21-dipropionate and 7α,9α,11β-trichloro-1,4-pregnadiene-17α,21-diol-3,20-dione 21-acetate;

21-halogeno-21-desoxy pregnadienes (i.e. compounds of formula I wherein M is CH₂G, G being halogen) such as 7α,21-dichloro-16α-methyl-1,4-pregnadiene-11β,17α-diol-3,20-dione 17-propionate and the 16β-methyl epimer thereof;

7α,21-dichloro-1,4-pregnadiene-11β,17α-diol-3,20-dione 17-propionate and the corresponding 7α-bromo derivative thereof;

21-desoxy pregnadienes (i.e. compounds of formula I wherein M is CH₂G, G being hydrogen) such as 7α-chloro-1,4-pregnadiene-11β,17α-diol-3,20-dione 17-propionate and the corresponding 7α-bromo derivatives;

7α-chloro-1,4-pregnadiene-17α-ol-3,20-dione, the 17-acetate, and the 17-propionate thereof, and the corresponding 7α-bromo and 7α-iodo derivatives;

16α-hydroxy pregnadienes (i.e. compounds of formula I wherein W is (H, α-OH)) and derivatives thereof such as 7α-chloro-1,4-pregnadiene-11β,16α,17α,21-tetrol-3,20-dione and the 17-propionate, the 16,21-diacetate 17-propionate, the 17-benzoate, the 17-benzoate 21-acetate, and the 16α,17α-methylorthobenzoate 21-acetate esters thereof, the 16α,17α-isopropylidenedioxy 21-acetate derivative thereof, and the corresponding 7α-bromo derivatives;

[17,16α-d] 1′,3′-oxathiolane derivatives (i.e. compounds of formula I wherein W and Q together form the grouping

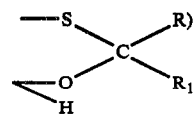

such as

7α-chloro-11β-hydroxy-2′,2′-dimethyl-1,4-pregnadieno[17,16α-d]-1′,3′-oxathiolane-3,20-dione; the 9α-chloro derivative thereof and the corresponding 7α-bromo derivatives of the foregoing;

5′βH-pregnadieno[17,16α-d]-oxazoles (i.e. compounds of formula I wherein W and Q together form the grouping

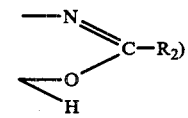

such as

7α-chloro-11β,21-dihydroxy-2′-methyl-5′βH-1,4-pregnadieno [17,16α-d]oxazole-3,20-dione 21-acetate and the corresponding 7α-bromo derivative;

20-carboxylate pregnadienes (i.e. compounds of formula I wherein M is -COOR₄, R₄ being a hydrocarbon) such as n-butyl 7α-chloro-11β-hydroxy-3,20-dioxo-16α-methyl 1,4-pregnadien-21-oate, propyl 2,7α-dichloro-11β-hydroxy-3,20-dioxo-16α-methyl-1,4-pregnadien-21-oate, and the corresponding 7α-bromo derivatives;

20-alkoxy-21-nor pregnadienes (i.e. compounds of formula I wherein M is —OR₃, R₃ being alkyl or halogenoalkyl) (also may be termed alkyl androstadiene-17β-carboxylates) such as 7α-chloro-16β-methyl-20-chloromethoxy-21-nor-1,4-pregnadiene-11β,17α-diol-3,20-dione 17-propionate.

7α-chloro-16-methylene-20-fluoromethyoxy-21-nor-1,4-pregnadiene-11β,17α-diol-3,20-dione 17-propionate.

7α-chloro-16β-methyl-20-methoxy-21-nor-1,4-pregnadiene-11β,17α-diol-3,20-dione 17-propionate and the corresponding 7α-bromo derivatives;

21-oxo pregnadienes and derivatives thereof (i.e. compounds of formula I wherein M is -CHO, and acetals, hemiacetals and acylals thereof) such as 2,7α-dichloro-9α-fluoro-16α-methyl-1,4-pregnadiene-11β,17α-diol-3,20,31-trione and the 21-methylhemiacetal thereof, 7α-chloro-9α9α-fluoro-16α-methyl-2,21-diacetoxy-1,4-pregnadiene-11β,17α-diol-3,20-dione 17-propionate, 7α-chloro-9α-fluoro-16α-methyl-,4-pregnadiene-11β,17α-diol-3,20,21-trione and the 21-ethylene ketal and the 21,21-dimethylacetal thereof, and the corresponding 7α-bromo derivatives thereof;

d-homo-pregnadienes such as

7α-chloro-p-homo-1,4-pregnadiene-11β,17α,21-triol-3,2-dione 17,21-di-n-butyrate and the corresponding 7α-bromo derivatives;

and 7α-fluoro and 7α-iodo derivatives such as 7α,9α-difluoro-16α-methyl-1,4-pregnadiene-11β,17α,21-triol-3,20-dione 21-acetate, and the 17-benzoate ester thereof, 7α-fluoro-1,4-pregnadiene-11β,17α,21-triol-3,20-dione 21-acetate and the 17,n-butyrate and 17-benzoate esters thereof and the 16α-methyl homologs of the foregoing,
and 7α-iodo-16α-methyl-1,4-pregnadiene-11β,17α,21-triol-3,20dione, the 21-acetate, 17-benzoate 2-acetate, and the 17,21-dipropionate esters therof, their 16β-methyl epimers, and the 9α-fluoro derivatives of the foregoing.

Another preferred group of compounds of this invention are the 11-oxo derivatives of formula I which, while possessing anti-inflammatory activity, ae more frequently used as intermediates in the preparation of the corresponding 11β-hydroxy derivatives according to procedures disclosed hereinbelow. Particularly valuable 11-oxo derivatives are the 11-oxo derivatives of following formula III:

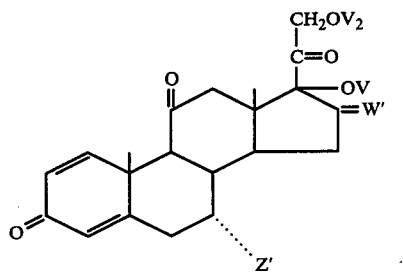

wherein Z' is chlorine or bromine;
W' is (H,CH₃) or =CH₂;
V and V₂ are each hydrogen or an acyl radical of a hydrocarboncarboxylic acid having up to 12 carbon atoms.

PROCESS OF THE INVENTION The 7α-chloro-, 7α-bromo- and 7α-iodo-9-unsubstituted- and the 7α-bromo- and 7α-iodo-9α-halogeno-3,20-dioxo-1,4-pregnadienes of our invention are conveniently prepared by the reaction of the corresponding hydrogen halide with a 9-unsubstituted- or 9α-halogeno-3,20-dioxo-1,4,6-pregnadiene in a nonreactive, organic solvent.

This process is preferably carried out under anhydrous conditions to minimize side reactions such as hydrolysis of any esters present. Saturated solutions of hydrogen halide in solvent are preferably employed to minimize reaction time.

Solvents suitable for use in this process are any nonreactive organic solvents in which the starting 3,20-dioxo-1,4,6-pregnatriene and the hydrogen halide are soluable. By "non-reactive" is meant any organic solvent which will not react with the steriod substrate or the hydrogen halide which would cause transformations resulting in competing side reactions. Thus, in our process, solvents to be avoided are water (which will cause hydrolysis of esters), alcohols (which might cause ester exchange under acid conditions), and nitriles such as acetonitrile (which would form iminoethers with steroidal alcohols).

Particularly useful solvents for our hydrogen halide addition process are ethers such as dioxane, tetrahydrofuran and diethylether; chlorinated solvents such as chloroform, methylene chloride and 1,2-ethylenedichloride; organic acids such as acetic and propionic acids; tertiary amides such as dimethylformamide, diethylformamide, and hexamethylphosphortriamide; and dimethylsulfoxide.

When carrying out our process, we usually use dioxane, acetic acid or tetrahydrofuran as solvent, tetrahydrofuran being preferred for reactions with hydrogen chloride and acetic acid for reactions with hydrogen bromide or hydrogen iodide.

Our reaction whereby a hydrogen halide is added to a 6-dehydro bond is preferably carried out at temperatures in the range of from about 0° C to about room temperature (e.g. 20° C) although lower temperatures (e.g. −20° C) and temperatures as high as about 60° C may be employed. The reaction time depends upon the hydrogen halide, solvent, and concentrate being employed. Thus, for example, the addition of hydrogen iodide in acetic acid is usually complete within one or two minutes; while the addition reaction utilizing hydrogen bromide in acetic acid at room temperature may be completed in from 20 to 60 minutes. The addition of hydrogen chloride in tetrahydrofuran is preferably carried out at 0° C since greater concentrations of hydrogen chloride in solvent are thereby obtained so that the reaction is completed within an hour. When carried out at room temperature, the addition of hydrogen chloride to a 6-dehydro bond may take up to 24 hours.

Substituents present in the 3,20-dioxo-1,4,6-pregnatriene starting steroids of our process usually remain unchanged under the conditions of our process. Indeed, it is usually preferable to have all the substituents desired in the 7α-halogeno-3,20-dioxo-1,4-pregnadiene product present in the 3,20-dioxo-1,4,6-pregnatriene starting compound. Thus, by way of example, the 3,20-dioxo-1,4,6-pregnatriene starting steroids of our process may be substituted at C-2 by methyl or halogen, at C-11 by oxygen, hydroxyl, formyloxy and halogen; at C-16 by acyloxy, alkyl, alkylidene, halogenoalkylidene, halogen; and at C-17 there may be present a corticoid side chain and derivatives thereof, or a progesterone side chain which may be substituted by a 17α-hydroxy, 17α-acyloxy or 17α-halogen and at C-21 by halogen, oxygen, and derivatives thereof.

Generally, when carrying out this process whereby a hydrogen halide is added to a 6-dehydro bond, to a saturated solution of dry hydrogen halide in anhydrous solvent (e.g. hydrogen bromide in acetic acid) usually at 0° C to 20° C, is added the starting 3,20-dioxo-1,4,6-pregnatriene (e.g. 16α-methyl-1,4,6-pregnatriene-11β,17α,21-triol-3,20-dione 17-benzoate 21-acetate) either in the solid state or in solution, the molar quantity of hydrogen halide to steroid being about 40 to 1. After the reaction is complete, as determined by thin layer chromatography, the reaction mixture is poured into ice water and the resultant precipitate of 7α-halogeno-3,20-dioxo-1,4-pregnadiene (e.g. 7α-bromo-16α-methyl-1,4-pregnadiene-11β,17α,21-triol-3,20-dione 17-benzoate 21-acetate) isolated via filtration or extraction techniques and purified utilizing known techniques usually via chromatography.

We have found, when preparing a 7α-halogeno-11β-hydroxy-3,20-dioxo-1,4-pregnadiene of formula I by the aforedescribed process, that better overall yields of pure product are obtained over that produced from the corresponding 11β-hydroxy-3,20-dioxo-1,4-pregnadiene when one hydrohalogenates the corresponding 11-oxo intermediate followed by reduction of the resulting 7α-halogeno-3,11,20-trioxo-1,4-pregnadiene with sodium borohydride (e.g. in methanol) whereby, when a 17-acyloxy group is present and when any 21-hydroxyl function is also esterified, there is obtained the corresponding 7α-halogeno-3,20-dioxo-11β-ol without reduction at the 3 or 20-oxo function. Thus, a preferred method of preparing 7α-chloro-16α-methyl-1,4 -pregnadiene-11β,17α,21-triol-3,20-dione 17,21-dipropionate comprises reaction of 16α-methyl-1,4,6-pregnatriene-17α,21-diol-3,11,20-trione 17,21-dipropionate with anhydrous hydrogen chloride in tetrahydrofuran at 0° C followed by reduction of the thereby formed 7α-chloro-16α-methyl-1,4-pregnadiene-17α,21-diol-3,11,20 -trione 17,21-dipropionate with sodium borohydride in methanol to produce excellent yields of pure 7α-chloro-16α-methyl-1,4-pregnadiene-11β,17α,21-triol-3,20-dione 17,21-dipropionate.

The 3,20-dioxo-1,4,6-pregnatriene starting compounds of the foregoing process are either known compounds or are conveniently prepared from the corresponding 3,20-dioxo-1,4-pregnadiene utilizing techniques known to effect dehydrogenation between C-6 and C-7 such as those utilizing chloranil or 2,3-dichloro-5,6-dicyanobenzoquinone (DDQ) or by bromination at C-6 followed by dehydrobromination. Since ester groups are usually present in the starting steroid, anhydrous conditions are preferably employed to minimize the possibility of hydrolysis.

The 7α-fluoro compounds of our invention are conveniently prepared by reaction of the corresponding 7β-hydroxy derivative with N-(2-chloro-1,1,2-trifluoroethyl)diethylamine (also known as fluoramine) in a halogenated solvent, preferably methylene chloride.

This process is preferably carried out at about 0° C under an inert atmosphere (e.g. argon, neon, nitrogen) under anhydrous conditions.

The starting 7β-hydroxy-3,20-dioxo-1,4-pregnadienes may be halogenated at C-9 or unsubstituted and preferably have all substituents present which are desired in the 7α-fluoro-3,20-dioxo-1,4-pregnadiene product. Also, all primary and unhindered alcohols must be protected, e.g. by an ester function.

In a preferred mode of preparing a 7α-fluoropregnadiene of our invention (e.g. 7α-fluoro-16α-methyl-1,4-pregnadiene-11β,17α,21-triol-3,20-dione 21-acetate or 9α-fluoro analog thereof), there is added fluoramine to an anhydrous solution of a 7β-hydroxy-3,20-dioxo-1,4-pregnadiene (e.g. 16α-methyl-1,4-pregnadiene-7β,11β,17α,21-tetrol-3,20-dione 21-acetate or the 9α-fluoro analog thereof) in a halogenated solvent (usually methylene chloride), at about 0° C the molar quantity of fluoramine to steroid being 6 to 1. The reaction is continued until completed as determined by thin layer chromatography and the product isolated by evaporation of the reaction mixture and purified via chromatographic techniques to obtain the desired 7α-fluoro derivative (e.g. 7α-fluoro-16α-methyl-1,4-pregnadiene-11β,17α,21-triol-3,20-dione 21-acetate or the 9α-fluoro analog thereof) sometimes in admixture with the corresponding 7-unsubstituted-6-dehydro derivative (e.g. 16α-methyl-1,4,6-pregnatriene-11β,17α,21-triol-3,20-dione 21-acetate or the 9α-fluoro analog thereof). Separation of such a mixture may be effected by converting the pregnatriene derivative to another 6,7-substituted derivative which is easily separable from the 7α-fluoro product via chromatographic techniques, e.g. to the corresponding 6β,7β-diol by reaction thereof with osmium tetroxide in dioxane in the presence of pyridine, thence separating the resulting mixture of 7α-fluoro-1,4-pregnadiene and 6β,7β-dihydroxy-1,4-pregnadiene via chromatographic techniques.

The 3,20 -dioxo-7β-hydroxy-1,4-pregnadiene precursors in the foregoing process are also useful intermediates in processes for preparing 7α-chloro-9α-halogen- and 7α-bromo-9α-halogenopregnadienes of our invention as well as the corresponding 9-unsubstituted derivatives thereof.

Thus, 7α-chloro-3,20-dioxo-1,4-pregnadienes (e.g. 7α-chloro-9α-fluoro-16α-methyl-1,4-pregnadiene-11β,17α,21-triol-3,20 -dione 21-acetate) are prepared from the corresponding 7β-hydroxy derivative by reaction thereof in a halogenated solvent (preferably methylene chloride) at about 0° C under an inert atmosphere (e.g. nitrogen) with N,N-diethyl-1,2,2-trichlorovinylamine, the molar quantity of reagent to steroid usually being in the range of 6 to 1.

Alternatively, 9α-halogeno and 9-unsubstituted-7α-chloro-3,20-dioxo-1,4-pregnadienes of our invention are prepared from the corresponding 7β-hydroxy derivative by reaction thereof with lithium chloride and fluoramine in tetrahydrofuran at about 0° C, the molar quantity of lithium chloride and fluoramine per mole of starting 7β-hydroxy-3,20 -dioxo-1,4-pregnadiene being 12 and 6, respectively.

Similarly, to prepare 7α-bromo-9α-halogeno (or 9-unsubstituted) pregnadienes of our invention (e.g 7α-bromo-9α-fluoro-16α-methyl-1,4-pregnadiene-11β,17α,21-triol-3,20-dione 21-acetate), the corresponding 7β-hydroxy derivative is reacted with fluoramine and lithium bromide at about 0° C in a halogenated solvent (usually methylene chloride), the molar quantities of lithium bromide and fluoroamine per mole of steroid being 12 and 6, respectively.

The 7β-hydroxy-3,20-dioxopregnadiene intermediates for the foregoing processes are novel compounds which are prepared by conversion of the corresponding 6β,7β-dihydroxy derivative to a 6β,7β-alkylorthoalkanoate ester by known procedures, followed by cleavage thereof with acid utilizing known techniques and thence reaction of the thereby formed 6β-acyloxy-7β-hydroxy derivative with chromous acetate, sodium acetate and aqueous acetic acid in acetone. Thus, for example, 16α-methyl-1,4-pregnadiene7β,11β,17α,21-tetrol-3,20-dione 21-acetate is prepared by reaction of the corresponding 6β-hydroxy derivative with tri-n-butylorthopropionate and p-toluenesulfonic acid monohydrate in dimethylsulfoxide followed by cleavage of the 9α-fluoro-16α-methyl-1,4-pregnadiene-6β,7β,11β,17α,21-pentol-3,20-dione 6,7-n-butylorthopropionate 21-acetate thereby formed with aqueous acetic acid and thence reaction of the resulting 6β-propionyloxy-7β-hydroxy derivative with chromous acetate and sodium acetate to give a 7β-hydroxy intermediate of this invention, 9α-fluoro-16α-methyl-1,4-pregnadiene-7β,11β,17α,21-tetrol-3,20-dione 21-acetate.

When preparing 9α-halogeno derivatives of this invention, i.e. 7α,9α,11β-trihalogeno derivatives such as 7α,9α,11β-trichloro-16α-methyl-1,4-pregnadiene-17α,21-diol-3,20-dione 17,21-dipropionate and 7α,9α-dihalogeno-11β-hydroxy derivatives such as 7α,9α-dibromo-16α-methyl-1,4-pregnadiene-11β,17α,21-triol-3,20-dione 17-benzoate 21-propionate and 7α,9α-dichloro-16α-methyl-1,4-pregnadiene-11β,17α,21-triol-3,20-dione 17,21-dipropionate, the 9α-halogeno and/or 11β-halogeno atoms may be present in the molecule prior to introduction of the 7α-halogeno. Alternatively, however, these substituents may be introduced into a 7α-halogeno-3,20-dioxo-1,4,9-(11)-pregnatriene derived from a 7α-halogeno-11β-hydroxy-3,20-dioxo-1,4-pregnadiene of this invention by reaction thereof with methanesulfonyl chloride and collidine in dimethylformamide in the presence of sulfur dioxide. For example, reaction of a 7α-halogen-9(11)-dehydro derivative (e.g. 7α-chloro-16α-methyl-1,4,9(11)-pregnatriene-17α,21-diol-3,20-dione 17,21-dipropionate) with chlorine in a halogenated solvent (e.g. chloroform) in the presence of an amine (e.g. pyridine) according to known procedures, yields the corresponding 7α,9α,11β-trichloro derivative (e.g. 7α,9α,11β-trichloro derivative (e.g. 7α,9α,11β-trichloro-16α-methyl, 1,4-pregnadiene-17α,21-diol-3,20-dione 17,21-dipropionate). Additionally, reaction of the foregoing 7α-halogeno-9(11)-dehydro derivative with N-chlorosuccinimide and perchloric acid utilizing known techniques yields the corresponding 9,11-chlorohydrin, e.g. 7α,9α-dichloro-16α-methyl-1,4-pregnadiene-11β,17α,21-triol-3,20-dione 17,21-dipropionate. Similarly, reaction of a 7α-halogeno-9(11)-dehydro derivative (e.g. 7α-bromo-16α-methyl-1,4,9(11)-pregnatriene-17α,21-diol-3,20-dione 17-benzoate 21-propionate) with N-bromosuccinimide and perchloric acid yields the corresponding 7α-halogeno-9α-bromo-11β-hydroxy compound of this invention, i.e. 7α,9α-dibromo-16α-methyl-1,4-preganadiene-17α,21-diol-3,20-dione 17-benzoate 21-propionate.

HYDROLYSIS AND PREPARATION OF ESTER DERIVATIVES

7α-Halogeno-3,20-dioxo-1,4-pregnadienes having ester functions such as at C-16, C-17 and/or at C-21 can be converted in known manner into 7α-halogeno-3,20-dioxo-1,4-pregnadienes having free hydroxyl groups as, for example, by the action of acidic saponification agents, preferably 70% perchloric acid in methanol. By regulating the reaction time and quantity of reagent, a 17,21-dihydrocarboncarboxylate can be converted to the corresponding 17-monoester or to the corresponding 17,21-diol. In view of the presence of a halogen at C-7 in the compounds of this invention, basic hydrolyzing agents are usually not desirable since side reactions will take place, such as elimination of the 7α-halogeno group; however, mild basic saponification agents such as aqueous sodium bicarbonate in methanol can successfully be employed.

When removing a hydrocarboncarboxylate ester at C-21 and at C-16, we prefer to utilize the diastase enzyme of malt in aqueous ethanol using known procedures. When a 7α-halogeno-3,20-dioxo-pregnadiene 17,21-dihydrocarboncarboxylate is reacted with malt diastase, hydrolysis occurs only at C-21 producing a 17-monohydrocarboncarboxylate which, if desired, can be reesterified at C-21 in known manner with an acylating agent containing a different acyl function than that present at C-17 so as to produce a mixed 17,21-diacyl derivative.

Another method of preparing a 7α-halogeno-3,20-dioxo-17,21-dihydroxypregnadiene is by conversion of the alkylidenedioxy functions at C-17(21) in known manner in an acidic medium (e.g. 50% aqueous acetic acid) under an atmosphere of nitrogen.

As disclosed hereinabove, the preferred compounds of our invention are those which are esterified at C-17, including 17-mono- and 17,21-diesters, the 17-propionate, 17-n-butyrate and 17-benzoate being particularly preferred ester derivatives. Usually, it is advantageous to introduce the ester groups into the 3,20-dioxo-1,4,6-pregnatriene and 7β-hydroxy-3,20-dioxo-1,4-pregnadiene precursors prior to introduction of the 7α-halogeno group.

The 17α,21-diesters are prepared according to known methods by acylation of the corresponding 17α,21-diols or 17α-hydroxy-21-acyloxy compounds, preferably by reaction of the steroid with an appropriate acid anhydride in the presence of a strong acid catalyst such as, e.g. p-toluenesulfonic acid, perchloric acid or strongly acidic cation exchange resins, or by using trifluoroacetic anhydride with an appropriate lower alkanoic acid.

Prior to esterifying a 17α-hydroxyl group, any 11β-hydroxyl function ought be protected such as by preparing the 11β-trifluoroacetate ester which, after esterification at C-17, may be hydrolyzed with mild base (e.g. dilute aqueous sodium benzoate) without hydrolyzing the other ester groups at C-17 and/or at C-21. Alternatively, the esterification may be carried out on an 11-oxo intermediate which, after esterification at C-17 and introduction of the halogen at C-7 may be reduced with sodium borohydride to produce the corresponding 7-halogeno-11β-hydroxy-17-monoacyloxypregnadiene.

The 17,21-diesters may also be prepared by acylation of the corresponding 21-hydroxy-17α-hydroxy-17α-monoesters by treatment there of with the appropriate acid anhydride or acid chloride under basic conditions, preferably in the presence of a tertiary organic base, e.g. pyridine, quinoline, N-methylpiperidine, N-methylmorpholine, p-dimethylaminopyridine or dimethylaniline.

The 17α-monoesters of our invention may be prepared by hydrolysis of a corresponding 17,21-orthoester or 17α,21-diester.

In preparing 17-monoesters via hydrolysis of a 17,21-orthoester, the 17,21-orthoester intermediate is conveniently prepared by reaction of the 17α,21-diol with an alkylorthoester followed by hydrolysis of the resulting 17,21-orthoester under mild conditions, i.e. hydrolysis in the presence of an acid catalyst (e.g. a lower alkanoic acid such as acetic or propionic) or a strong mineral acid such as hydrochloric, sulfuric acid. When no substituent is present at C-16 the hydrolysis is preferably carried out under buffered conditions at a pH in the range of 4 to 6.

To prepare 16α,17α- or 17α,21-alkylidenedioxy derivatives of the 1,4,6-pregnatriene and 7β-hydroxy-1,4-pregnadiene precursors of this invention, the corresponding 16α,17α-dihydroxy- or 17α,21-dihydroxy steroid intermediate is reacted with a ketone or aldehyde (e.g. acetone, acetaldehyde, acetophenone) in the presence of a mineral acid (e.g. hydrochloric acid) whereby is obtained the corresponding 16α,17α-alkylidenedioxy or 17α,21-alkylidenedioxy derivative.

The 21-dihydrogenphosphate esters of this invention are prepared by reaction of the corresponding 21-hydroxy compound with pyrophosphoryl chloride utilizing known techniques. Both the mono- and dialkali salts and alkaline earth metal salts of the dihydrogen phosphate ester thereby formed by be obtained by neutralizing said dihydrogen phosphate ester with an alkali methoxide or alkaline earth methoxide.

THE METHOD OF USE AND PHARMACEUTICAL FORMULATION ASPECTS OF THE INVENTION

The present invention includes within its scope the method of treating an inflammatory condition in a warm-blooded animal responsive to treatment with anti-inflammatory agents which comprises administering to said animal a non-toxic, anti-inflammatory effective amount of a 7α-halogeno-3,20-dioxo-1,4-pregnadiene of formula I.

In general, the pharmacologically active 7α-halogeno-3,20-dioxo-1,4-pregnadienes of formula I, particularly the 7α-chloro and 7α-bromo derivatives, have pharmacological effects similar to those of the corresponding 7-unsubstituted analog and may be administered in similar pharmaceutical forms and for the same indications for which the corresponding 7-unsubstituted-3,20-dioxo-1,4-pregnadiene would be applicable, the total daily dosage depending upon the nature and severity of the inflammation being treated, the age and size of the patient and the specific potency of the 7α-halogeno-3,20-dioxo-1,4-pregnadiene being administered. Thus, in general, 7α-halogen-3,20-dioxo-1,4-pregnadienes of formula I may be administered orally in the form of tablets, elixirs, capsules and the like for all inflammatory disorders, particularly arthritis, rheumatism and the like; intravenously in aqueous solution as the 21-hemisuccinate or 21-phosphate ester for the treatment of shock and intramuscularly for long-term systemic activity.

In particular, the 7α-halogeno-3,20-dioxo-1,4-pregnadienes of formula I having hydroxyl groups or esters thereof at C-17 and C-21 (i.e. compounds of formula I wherein Q is OV and M is —CH$_2$OV$_2$), particularly the 17α-hydrocarboncarboxylates thereof, and more particularly, the preferred compounds of formula II, are valuable anti-inflammatory agents when administered topically, or locally, since they have high anti-inflammatory action coupled with low glucocorticoid action on topical administration, as well as low glucocorticoid activity when administered systemically. The compounds thus have the desirable high anti-inflammatory action on topical administration with little risk of disturbance of the mineral balance or other systemic action should the compound be absorbed.

The 7α-halogeno-3,20-dioxo-17 α,21dihydroxy-1,4-pregnadienes and the 17 and/or 21-esters thereof may be applied topically or locally in any of the conventional pharmaceutical forms. For example, they may be administered intra-articularly for long-term local activity with minimal systemic effects in aqueous suspensions as the 17,21-dihydrocarboncarboxylate esters, e.g. the 17,21-dipropionate, 17,21-di-n-butyrate, and 17-benzoate 21-acetate; or topically in creams, lotions, aerosols or ointments as the 17-mono-lower alkanoate or benzoate or the 17,21-diesters (e.g. 17,21-dipropionate) in the treatment of all corticosteroid responsive dermatoses such as contact and allergic dermatitis and psoriasis or in the form of ophthalmic suspensions or nasal sprays. Advantageously, when topically administering preferred compounds of our invention, i.e. 7α-chloro and 7α-bromo-3,20-dioxo-1,4-pregnadiene of formula II, and particularly the 17,21-dihydrocarboncarboxylates thereof, the therapeutic topical dosages will generally be lower than those required when administering the corresponding 7-unsubstituted analog. Thus, a preferred mode of the method-of-use aspect of our invention comprises the method of treating a topical inflammatory condition, e.g. inflammation of the skin or mucous membrane, which comprises topically applying to the affected area in a concentration effective for the topical treatment of inflammation of 7α-halogeno-3,20-dioxo-1,4-pregnadiene of formula II in association with a pharmaceutical carrier.

Included within the term "topically applying" are topical application of skin whereby our compounds of formula II are effective in the treatment and control of all corticosteroid-responsive dermatoses, e.g., psoriasis, and of corticosteroid-responsive conditions such as alopecia areata or alopecia totalis; inhalation aerosol application whereby our preferred compounds of formula II are effective in the treatment of, e.g. respiratory inflammatory disorders such as asthma and allergic rhinitis; and intra-articular injection application whereby our preferred compounds of formula II are effective in the treatment of local inflammatory disorders such as rheumatoid arthritis, tennis elbow, bursitis, peritendinitis, capsulitis, gout, and acute shoulder dermatitis.

Particularly valuable compounds of formula II for the topical treatment of inflammatory disorders are the 16α-methyl-17α,21-dihydrocarboncarboxylates such as the 7α-chloro and 7α-bromo derivatives of 16α-methyl-1,4-pregnadiene-11β,17α,21-triol-3,20-dione 17,21-dipropionate and the 7α-chloro and 7α-bromo derivatives of 16α-methyl-1,4-pregnadiene-11β,17α,21-triol-3,20-dione 17-benzoate 21-acetate, all of which have much greater topical activity than the corresponding 7-unsubstituted precursor or than betamethasone 17-valerate (i.e. 9α-fluoro-16β-methyl-1,4-pregnadiene-11β,17α,21-triol-3,20-dione 17-valerate) which exhibit low systemic effects following topical application, and low skin atrophy as well as low parenteral and oral activities.

Also within the scope of our invention are pharmaceutical compositions for use in the treatment of inflammation comprising an effective amount of our novel 3,20-dioxo-7α-halogeno-1,4-pregnadienes of formula I in association with a compatible, pharmaceutically acceptable carrier or coating. Of the foregoing, preferred are pharmaceutical compositions for topical administration comprising the 7α-chloro- and 7α-bromo-3,20-dioxo-1,4-pregnadienes of formula II of which the 17,21-diesters, particularly those having a 16α-methyl group, are of greatest value as topical anti-inflammatories.

The pharmaceutical dosage forms are prepared according to procedures well known in the art and may contain other active ingredients, e.g. neomycin sulfate in cream for topical use.

The active steroid may be formulated into a preparation suitable for topical administration in conventional manner with the aid of one or more carriers or excipients. Examples of types of preparation include ointments, lotions, creams, sprays, powders, drops (e.g. ear drops and eye drops), suppositories or retention enemas (e.g. for the treatment of rectal or colonic inflammations) and tablets or pellets (e.g. for the treatment of aphthous ulcers) and aerosols. Ointments and creams may, for example, be formulated with an aqueous or oily base with the addition of suitable thickening and/or gelling agents. Such bases may thus, for example, include water and/or an oil such as liquid paraffin or a vegetable oil such as peanut oil or castor oil. Thickening agents which may be used according to the nature of the base include soft paraffin, aluminum stearate, cetostearyl alcohol, polyethylene glycols, woolfat, hydrogenated lanolin, beeswax, etc.

Lotions may be formulated with an aqueous or oily base and will in general also include one or more of the following, namely, stabilizing agents, emulsifying agents, dispersing agents, suspending agents, thickening agents, coloring agents, perfumes and the like.

Powders may be formed with the aid of any suitable powder base, e.g. talc, lactose, starch, etc. Drops may be formulated with an aqueous base or non-aqueous base also comprising one or more dispersing agents, suspending agents, solubilizing agents, etc.

The pharmaceutical compositions according to the invention may also include one or more preservatives or bacteriostatic agents, e.g. methyl hydroxybenzoate, propyl hydroxybenzoate, chlorocresol, benzalkonium chlorides, etc.

The compositions according to the invention may also contain other active ingredients such as antimicrobial agents, particularly antibiotics.

The proportion of active steroid in the compositions according to the invention depends on the precise type of formulations to be prepared but will generally be within the range of from 0.0001% to 5% by weight. Generally, however, for most types of preparations advantageously the proportion used will be within the range of from 0.001 to 0.5% and preferably 0.01 to 0.25%.

The following illustrate topical formulations prepared in accordance with our invention. In each, the active ingredient is 7α-chloro-16α-methyl-1,4-pregnadiene-11β,17α,21-triol-3,20-dione 17,21-dipropionate. It will be appreciated, however, that this compound may be replaced by equivalent quantities of other active 7α-halogeno compounds of this invention, e.g. by the 17,21-dipropionate or the 17-benzoate 21-propionate of 7α-bromo-16α-methyl-1,4-pregnadiene-11β,17α,21-triol-3,20-dione.

FORMULATION

| 1. Ointment | mg/g |
|---|---|
| 7α-chloro-16α-methyl-1,4-pregnadiene-11β,17α,21-triol-3,20-dione 17,21-dipropionate, Micronized | 0.1–5.0 |
| Mineral Oil | 20.0 |
| White Petrolatum to make | 1.00 g |

Melt and heat the white petrolatum to 55° C. Heat the mineral oil to 40° C. Disperse the 7α-chloro-16α-methyl-1,4-pregnadiene-11β,17α,21-triol-3,20-dione 17,21-dipropionate in the mineral oil and mill the suspension. Add the suspension to the melted white petrolatum with agitation. Start cooling and continue to agitate until the temperature reaches 30° C.

| 2. Glycol Ointment | mg/g |
|---|---|
| 7α-chloro-16α-methyl-1,4-pregnadiene-11β,17α,21-triol-3,20-dione 17,21-dipropionate | 0.1–0.5 |
| Hexylene Glycol | 100.0 |
| Propylene Glycol Monostearate | 20.0 |
| White wax | 60.0 |
| White Petrolatum to make | 1.00 g |

Melt and heat together to 60°–65° C the propylene glycol monostearate, white wax and white petrolatum. Heat the hexylene glycol to 40° C and dissolve the 7α-chloro-16α-methyl-1,4-pregnadiene-11β,17α,21-triol-3,20-dione 17,21-dipropionate in it. Add the solution of the hexylene glycol to the above oily phase (cooled to 55° C) with agitation. Start cooling and continue to agitate until the temperature reaches 30° C.

| 3. Lotion | mg/g |
|---|---|
| 7α-chloro-16α-methyl-1,4-pregnadiene-11β,17α,21-triol-3,20-dione 17,21-dipropionate | 0.1–5.0 |
| Ethyl Alcohol | 400.0 |
| Polyethylene Glycol 400 | 300.0 |

| 3. Lotion -continued | mg/g |
|---|---|
| Hydroxypropyl Cellulose | 5.0 |
| Propylene Glycol to make | 1.0 g |

Dissolve the 7α-chloro-16α-methyl-1,4-pregnadiene-11β,17α,21-triol-3,20-dione 17,21-dipropionate in the mixture of the ethyl alcohol polyethylene glycol and propylene glycol. Slowly add the hydroxypropyl cellulose and continue to agitate until the hydroxypropyl cellulose is completely dispersed and wetted and a clear lotion is produced.

| 4. Gel | mg/g |
|---|---|
| 7α-chloro-16α-methyl-1,4-pregnadiene-11β,17α,21-triol-3,20-dione 17,21-dipropionate | 0.1–5.0 |
| Ethyl Alcohol | 400.0 |
| Polyethylene Glycol 400 | 300.0 |
| Carbopol 940 (Goodrich) | 15.0 |
| Potassium Hydroxide | 3.0 |
| Propylene Glycol to make | 1.00 g |

Dissolve the 7α-chloro-16α-methyl-1,4-pregnadiene-11β,17α,21-triol-3,20-dione 17,21-dipropionate in a mixture of the ethyl alcohol, polyethylene glycol 400 and a portion of the propylene glycol. Use the remaining portion of the propylene glycol to dissolve the potassium hydroxide. Add the Carbopol 940 slowly to the above mixture and continue to agitate until the Carbopol 940 is completely dispersed and wetted. Add slowly the potassium hydroxide solution and continue to agitate until a clear gel is produced.

| 5. Cream | mg/g |
|---|---|
| 7α-chloro-16α-methyl-1,4-pregnadiene-11β,17α,21-triol-3,20-dione 17,21-dipropionate, Micronized | 0.1–5.0 |
| Isopropyl Palmitate | 100.0 |
| Glyceryl Stearate | 80.0 |
| Promulgen-Type D (Robinson, Wagner Co.) | 50.0 |
| White Wax | 50.0 |
| Propylene Glycol | 100.0 |
| Purified water to make | 1.00 g |

Melt together and heat to 75° C the white wax, glyceryl stearate, Promulgen-Type D and a portion of the isopropyl palmitate and maintain the temperature. Disperse the 7α-chloro-16α-methyl-1,4-pregnadiene-11β,17α,21-triol-3,20-dione 17,21-dipropionate in the remaining portion of the isopropyl palmitate and mill the dispersion. While agitating add the dispersion to the above oily phase. Heat together the water and the propylene glycol to 75° C. Add the solution to the above oily phase with agitation. Start cooling and continue to agitate until the temperature reaches 30° C.

| 6. Topical Aerosol | mg/can |
|---|---|
| 7α-chloro-16α-methyl-1,4-pregnadiene-11β,17α,21-triol-3,20-dione 17,21-dipropionate | 6.4 |
| Mineral Oil | 1,250.0 |
| Neobee M-5 (Caprylic/Capric Glyceride) (PVO International, Inc.) | 3,743.6 |
| Dichlorodifluoromethane | 17,200.0 |
| Trichloromonofluoromethane | 68,800.0 |
| | 91,000.0 |

Dissolve the 7α-chloro-16α-methyl-1,4-pregnadiene-11β,17α,21-triol-3,20-dione 17,21-dipropionate in Neobee M-5 (Caprylic/Capric Glyceride) and add mineral oil. Place this concentrate into an aerosol and crimp a valve on the can. Inject the dichlorodifluoromethane and trichloromonofluoromethane mixture into the container through the valve.

| 7. Inhalation Aerosol | mg/can |
|---|---|
| 7α-chloro-16α-methyl-1,4-pregnadiene-11β,17α,21-triol-3,20-dione 17,21-dipropionate | 12.60 |
| Oleic Acid | 1.26 |
| Trichloromonofluoromethane | 5,686.14 |
| Dichlorodifluoromethane | 14,700.00 |
| | 20,400.00 |

Disperse the 7α-chloro-16α-methyl-1,4-pregnadiene-11β,17α,21-triol-3,20-dione 17,21-dipropionate in trichloromonofluoromethane containing oleic acid and meter the resulting suspension into the cans. Crimp a valve onto the can and inject dichlorodifluoromethane into the container through the valve.

| 8. Intra-Articular Injection | mg/ml |
|---|---|
| 7α-chloro-16α-methyl-1,4-pregnadiene-11β,17α,21-triol-3,20-dione 17,21-dipropionate | 0.1–5.0 |
| Sodium Phosphate, dibasic, anhydrous R | 2.00 |
| Sodium Chloride, USP | 5.00 |
| Disodium EDTA, USP | 0.10 |
| (Disodium Ethylene diamine tetraacetate) | |
| Polysorbate 80, USP | 0.50 |
| Benzyl Alcohol, R | 9.00 |
| Methylparaben, USP | 1.80 |
| Propylparaben, USP | 0.20 |
| Sodium CMC | 5.00 |
| (Sodium Carboxymethylcellulose) | |
| Polyethylene Glycol 4000, USP | 20.00 |
| HCl 1N qs pH 7.1 | |
| Distilled Water qs ad | 1.00 ml |

| Method of Manufacture: Vehicle A (10X) | mg/ml | gm/5 liters (required to make 50 liters final suspension |
|---|---|---|
| Sodium Phosphate, Dibasic, Anhydrous, R | 20.0 | 100.0 |
| Sodium Chloride, R | 50.0 | 250.0 |
| Disodium EDTA, Dihydrate, R | 1.0 | 5.0 |
| Polysorbate 80, USP | 5.0 | 25.0 |
| 1N HCl qs pH 7.10 | | |
| Water for Injection qs ad | 1.0 ml | 5.0 liters |

1. Collect approximately 80% of water for injection of the final volume of Vehicle A. Sparge with nitrogen.
2. Dissolve with agitation the disodium EDTA, dibasic sodium phosphate, sodium chloride. Discontinue nitrogen sparging and disperse the Polysorbate 80 while overlaying with nitrogen.
3. 3. Adjust the pH of the solution to 7.1 with 1.0 N hydrochloric acid solution, then add sufficient water to bring Vehicle A to the required volume. Sterile filter, overlay with sterile nitrogen.

| Vehicle B (1.33X) | mg/ml | gm/37.5 liters (required to make 50 liters final suspension |
|---|---|---|
| Benzyl Alcohol, R | 12.000 | 450.0 |
| Methylparaben, USP | 2.400 | 90.0 |
| Propylparaben, USP | 0.266 | 10.0 |
| Sodium Carboxymethylcellulose | 6.670 | 250.0 |
| Polyethylene Glycol 4000, USP | 26.670 | 1,000.0 |
| Water for Injection qs ad | 1.000 ml | 37.5 liters |

1. Charge approximately 95% (35.6 liters) of the water for injection.
2. Separately dissolve the methyl- and propylparaben in the benzyl alcohol, then add the sodium carboxymethylcellulose and add this slurry to the water for injection.
3. Charge the polyethylene glycol 4000, USP.
4. Bring the volume of Vehicle B to the final volume and pass through an 8.0 μ Millipore membrane into containers for autoclaving.

| Final Suspension | per liter | per 50 liters |
|---|---|---|
| 7α-chloro-16α-methyl-1,4-pregnadiene-11β,17α,21-triol-3,20-dione 17,21-dipropionate | 0.1 to 5.0 gm | 5.0 to 250 gm |
| Vehicle A | 100.00 ml | 5,000.0 ml |
| Vehicle B | 750.00 ml | 37,500.0 ml |
| Water for Injection qs ad | 1,000.00 ml | 50.0 liters |

1. In a suitable sterile area, charge 27.5 liters of Vehicle B to a compounding tank.
2. Disperse the steroid in a minimum quantity of Vehicle A, and pass the slurry through a colloid mill until the particles are well dispersed, then rinse the mill with the remainder of Vehicle A.
3. Add to the slurry an approximate equal volume of Vehicle B, pass the resultant flocculated suspension through the mill, then pass the suspension through a sterile mesh screen into the compounding tank.
4. Rinse the mill with part of Vehicle B followed by water, pass the rinse through the screen into the compounding tank. Add the remainder of Vehicle B, then water, to bring the batch up to the required volume. Mix well.
5. Fill aseptically into siliconed vials and/or ampules, overlay with nitrogen, and stopper.

| 9. Solution | mg/ml |
|---|---|
| 7α-chloro-16α-methyl-1,4-pregnadiene-11β,17α,21-triol-3,20-dione 17,21-dipropionate | 0.1–5.0 |
| N-methylpyrrolidone | 200 |
| Isopropyl myristate | 50 |
| Isopropyl alcohol | qs to 1.0 ml. |

Dissolve the 7α-chloro-16α-methyl-1,4-pregnadiene-11β,17α,21-triol-3,20-dione 17,21-dipropionate in a portion of the N-methylpyrrolidone. Mix the isopropyl myristate with a portion of isopropyl alcohol. Mix the two solutions, add the remainder of the N-methylpyrrolidone, then isopropyl alcohol to the desired volume.

The processes described hereinabove are illustrated in detail in the Examples hereinbelow and should not be construed as limiting the invention, equivalents thereof and products produced thereby which will be obvious to one skilled in the art being considered a part of the invention.

The molecular structure of the compounds of the invention described in detail hereinbelow were assigned on the basis of their method of preparation and study of their chromatographic characteristics and of their nuclear magnetic resonance (nmr), mass spectra and ultraviolet spectra, and were confirmed by the correspondence between calculated and found values of elementary analyses for the elements.

PREPARATION 1

16α-METHYL-1,4,6-PREGNATRIENE-11β,17α,21-TRIOL-3,20-DIONE AND 21-ESTERS THEREOF

A. 16α-Methyl-1,4,6-Pregnatriene 11β,17α,21-Triol-3,20-Dione 21-Acetate

To a solution of dry hydrogen chloride gas (22 gms.) in dioxane (660 ml.), add 16α-methyl-1,4-pregnadiene-11β,17α,21-triol-3,20-dione 21-acetate (10 gms.) followed by 2,3-dichloro-5,6-dicyanobenzoquinone (DDQ) (6.55 gms.) and stir at room temperature for 24 hours. Filter the reaction mixture and evaporate the filtrate at 40° C in vacuo. Dissolve the resultant residue in chloroform:ethyl acetate (1:1) and filter the solution through a column of neutral alumina, washing the column with the same solvent system. Evaporate the eluates and crystallize the resultant residue from methanol:hexane to give 16α-methyl-1,4,6-pregnatriene-11β,17α,21-triol-3,20-dione 21-acetate.

B. 16α-Methyl-1,4,6-Pregnatriene-11β,17α,21-Triol-3,20-Dione

To a solution of 16α-methyl-1,4,6-pregnatriene-11β,17α,21-triol-3,20-dione 21-acetate (1.5 gms.) in methanol (360 ml.) add saturated aqueous sodium bicarbonate solution (40 ml.). Stir at room temperature for 2 hours, then filter and evaporate in vacuo. Dissolve the resultant residue in ethyl acetate, wash the ethyl acetate solution with water, dry over magnesium sulfate and evaporate in vacuo to obtain 16α-methyl-1,4,6-pregnatriene-11β,17α,21-triol-3,20-dione.

C. 16α-Methyl-1,4,6-Pregnatriene-11β,17α,21-Triol-3,20-Dione 21-Benzoate (1) To 16α-methyl-1,4,6-pregnatriene-11β,17α,21-triol-3,20-dione (0.68 gms.) in pyridine (6.12 ml.) add benzoyl chloride (1.36 ml.). Stir at room temperature for 30 minutes, then pour into a 0.1 N hydrochloric acid solution (550 ml.). Extract the aqueous mixture with ethyl acetate, wash the organic extracts with aqueous saturated sodium bicarbonate solution, then with water, then dry over magnesium sulfate and evaporate in vacuo to a residue of 16α-methyl-1,4,6-pregnatriene-11β,17α,21-triol-3,20-dione 21-benzoate.

(2) In the above procedure, by substituting for benzoyl chloride equivalent quantities of substituted benzoyl chloride, e.g. p-toluyl chloride, p-fluorobenzoyl chloride and 3',5'-dimethylbenzoyl chloride, there is obtained the corresponding 21-substituted benzoate ester, e.g. the 21-p-toluate, 21-p-fluorobenzoate and 21-(3',5'-dimethylbenzoate) of 16α-methyl-1,4,6-pregnatriene-11β,17α,21-triol-3,20-dione.

D. 16α-Methyl-1,4,6-Pregnatriene-11β,17α,21-Triol-3,20-Dione 21-Hydrocarboncarboxylates (1) 16α-Methyl-1,4,6-Pregnatriene-11β,17α,21-Triol-3,20-Dione 21-Trimethylacetate To 16α-methyl-1,4,6-pregnatriene-11β,17α,21-triol-3,20-dione (0.4 gms.) in pyridine (3 ml.) at 0° C, add dropwise a solution of trimethylacetyl chloride (0.4 ml.) in pyridine (1 ml.). Allow the reaction mixture to warm to room temperature, then leave at room temperature for 30 minutes. Pour the reaction mixture into water (250 ml.), extract the aqueous mixture with ethyl acetate, then wash the organic extracts successively with 1 N hydrochloric acid, aqueous saturated sodium bicarbonate, then water. Dry over magnesium sulfate and evaporate in vacuo to a residue of 16α-methyl-1,4,6-pregnatriene-11β,17α,21-triol-3,20-dione 21-trimethylacetate.

(2) In the above procedure, by substituting for trimethylacetyl chloride, equivalent quantities of other hydrocarboncarboxylic acid chlorides, e.g. propionyl chloride, dodecanoyl chloride, valeryl chloride, n-butyryl chloride, cyclopentylpropionyl chloride, cyclohexylcarbonyl chloride, 1-adamantylacetyl chloride, and 1-adamantylcarboxylic acid chloride, there is obtained the corresponding 21-hydrocarboncarboxylate ester, e.g. the 21-propionate, 21-dodecanoate, 21-valerate, 21-n-butyrate, 21-cyclopentylpropionate, 21-cyclohexanecarboxylate, 21-(1'-adamantylacetate) and 21-(1'-adamantylcarboxylate) of 16α-methyl-1,4,6-pregnatriene-11β,17α,21-triol-3,20-dione.

PREPARATION 2

16α-METHYL-1,4,6-PREGNATRIENE-11β,17α,21-TRIOL-3,20-DIONE 17-LOWER ALKANOATES AND 17,21-ALKYLORTHOALKANOATES

A. 16α-Methyl-1,4,6-Pregnatriene-11β,17α,21-Triol-3,20-Dione 17-Propionate (1) 16α-Methyl-1,4,6-Pregnatriene-11β,17α,21-Triol-3,20-Dione 17,21-Ethylorthopropionate To 16α-methyl-1,4,6-pregnatriene-11β,17α,21-triol-3,20-dione (1.9 gms.) in dimethylsulfoxide (9.5 ml.), add triethylorthopropionate (3.8 ml.) and p-toluenesulfonic acid monohydrate (0.142 gms.). Stir for 2 hours at room temperature, then pour into water (250 ml.), add saturated aqueous sodium bicarbonate (150 ml.) and extract with ethyl acetate. Combine the ethyl acetate extracts and wash with water, dry over magnesium sulfate and evaporate in vacuo to a residue comprising 16α-methyl-1,4,6-pregnatriene-11β,17α,21-triol-3,20-dione 17,21-ethylorthopropionate.

(2) Dissolve the product of Preparation 2A(1) in glacial acetic acid (15 ml.) and water (0.3 ml.). Allow to stand for one hour at room temperature, then pour into water (300 ml.) and add an 8% aqueous sodium hydroxide solution (50 ml.). Separate the resultant precipitate by filtration, wash with water and dry at room temperature to give 16α-methyl-1,4,6-pregnatriene-11β,17α,21-triol-3,20-dione 17-propionate. Further purify by recrystallization from acetone/hexane.

B. 16α-Methyl-1,4,6-Pregnatriene-11β,17α,21-Triol-3,20-Dione 17-Lower alkanoates (1) 16α-Methyl-1,4,6-Pregnatriene-11β,17α,21-Triol-3,20-Dione 17,21-Alkylorthoalkanoate In the procedure of Preparation 2A(1), substitute for triethylorthopropionate the following trialkylorthoalkanoates, e.g. triethylorthoacetate, triethyltortho-n-butyrate, triethylorthoisobutyrate and tri-n-butylorthovalerate to obtain the corresponding 17,21-alkylorthoalkanoate, e.g. the 17,21-ethylorthoacetate, the 17,21-ethylortho-n-butyrate, the 17,21-ethylorthoisobutyrate, and the 17,21-n-butylorthovalerate, respectively of 16α-methyl-1,4,6-pregnatriene-11β,17α,21-triol-3,20-dione.

(2) 16α-Methyl-1,4,6-Pregnatriene-11β,17α,21-Triol-3,20-Dione 17-Lower alkanoate Treat each of the 17,21-alkylorthoalkanoates prepared in Preparation 2B(1) with aqueous acetic acid in the manner of Preparation 2A(2) to obtain, respectively, the 17-acetate, 17-n-butyrate, 17-isobutyrate, and 17-valerate esters of 16α-methyl-1,4,6-pregnatriene-11β,17α,21-triol-3,20-dione.

C. 16α-Methyl-1,4,6-Pregnatriene-11β,17α,21-Triol-3,20-Dione 17-Benzoate (1) 16α-Methyl-1,4,6-Pregnatriene-11β,17α,21-Triol-3,20-Dione 17,21-Methylorthobenzoate To a solution of 16α-methyl-1,4,6-pregnatriene-11β,17α,21-triol-3,20-dione (1 gm.) in dioxane (56 ml.) and benzene (84 ml.) add pyridinium p-toluenesulfonate (0.25 gms.) and trimethylorthobenzoate (1.5 ml.). Heat the reaction mixture at reflux temperature for 2 days, then add additional pyridinium p-toluenesulfonate (0.1 gms.) and trimethylorthobenzoate (1 ml.). Heat at reflux temperature an additional 3 days, then again add additional pyridinium p-toluenesulfonate (0.1 gms.) and trimethylorthobenzoate (1 ml.). Heat at reflux temperature another 3 days, cool, add pyridine (0.45 ml.) and evaporate in vacuo. Dissolve the resultant residue in ethyl acetate, wash the ethyl acetate solution with water, dry over magnesium sulfate and evaporate to a residue comprising 16α-methyl-1,4,6-pregnatriene-11β,17α,21-triol-3,20-dione 17,21-methylorthobenzoate.

In the above procedure by substituting for trimethylorthobenzoate an equivalent quantity of trimethylortho-(p-fluorobenzoate) there is obtained 16α-methyl-1,4,6-pregnatriene-11β,17α,21-triol-3,20-dione 17,21-methylortho-(p-fluorobenzoate).

(2) Treat 16α-methyl-1,4,6-pregnatriene-11β,17α,21-triol-3,20-dione 17α,21-methylorthobenzoate in aqueous acetic acid in a manner similar to that described in Preparation 2A(2) and isolate the resultant product in a manner similar to that described to obtain 16α-methyl-1,4,6-pregnatriene-11β,17α,21-triol-3,20-dione 17-benzoate.

In similar manner, by treating 16α-methyl-1,4,6-pregnatriene-11β,17α,21-triol-3,20-dione 17α,21-methylortho-(p-fluorobenzoate) with aqueous acetic acid, there is obtained 16α-methyl-1,4,6-pregnatriene-11β,17α,21-triol-3,20-dione 17-p-fluorobenzoate.

PREPARATION 3

16α-METHYL-1,4,6-PREGNATRIENE-11β,17α,21-TRIOL-3,20-DIONE 17,21-DIHYDROCARBONCARBOXYLIC ACID ESTERS

A. 16α-Methyl-1,4,6-Pregnatriene-11β,17α,21-Triol-3,20-Dione 17-Propionate 21-Alkanoate (1) 16α-Methyl-1,4,6-Pregnatriene-11β,17α,21-Triol-3,20-Dione 17,21-Dipropionate To 16α-methyl-1,4,6-pregnatriene-11β,17α,21-triol-3,20-dione 17-propionate (2.8 gms.) in pyridine (23 ml.), add propionic acid anhydride (4.6 ml.) and allow to stand at room temperature for 3.5 hours. Pour into water (250 ml.) containing 1 N hydrochloric acid (50 ml.). Extract with ethyl acetate (100 ml.), wash the combined organic extracts with water, dry over magnesium sulfate and evaporate in vacuo. Chromatograph the resultant residue on a silica gel column eluting with chloroform:ethyl acetate (4:1). Evaporate the combined eluates to a residue comprising 16α-methyl-1,4,6-pregnatriene-11β,17α,21-triol-3,20-dione 17,21-dipropionate.

(2) In the procedure of Preparation 3A(1) by substituting for propionic acid anhydride equivalent quantities of other alkanoic anhydrides, e.g. acetic anhydride, n-butyric anhydride, isobutyric anhydride, caprylic acid anhydride and valeric anhydride, there is obtained the corresponding 17-propionate 21-alkanoate ester, e.g. the 17-propionate 21-acetate, 17-propionate 21-n-butyrate, 17-propionate 21-isobutyrate, 17-propionate 21-caprylate, and 17-propionate 21-valerate of 16α-methyl-1,4,6-pregnatriene-11β,17α,21-triol-3,20-dione.

(3) Treat 16α-methyl-1,4,6-pregnatriene-11β,17α,21-triol-3,20-dione 17-propionate with benzoyl chloride in a manner similar to that described in Preparation 1C(1) to obtain 16α-methyl-1,4,6-pregnatriene-11β,17α,21-triol-3,20-dione 17-propionate 21-benzoate.

In the above procedure, by substituting for benzoyl chloride equivalent quantities of substituted benzoyl chloride, e.g. p-toluyl chloride, p-fluorobenzoyl chloride and 3',5'-dimethylbenzoyl chloride, there is obtained the 21-substituted benzoate ester, e.g. the 17-propionate 21-p-toluate, 17-propionate 21-p-fluorobenzoate, and the 17-propionate 21-(3',5'-dimethylbenzoate) of 16α-methyl-1,4,6-pregnatriene-11β,17α,21-triol-3,20-dione.

B. 16α-Methyl-1,4,6-Pregnatriene-11β,17α,21-Triol-3,20-Dione 17,21-Dihydrocarboncarboxylates (1) In a manner similar to that described in Preparation 3A(1), treat each of the 17-acetate, the 17-n-butyrate, the 17-isobutyrate, the 17-valerate, and the 17-benzoate esters of 16α-methyl-1,4,6-pregnatriene-11β,17α,21-triol-3,20-dione in pyridine with each of the following alkanoic acid anhydrides: acetic anhydride, propionic anhydride, n-butyric anhydride, isobutyric anhydride and valeric anhydride. Isolate and purify each of the resultant products in a manner similar to that described to obtain the corresponding 17-hydrocarboncarboxylate 21-alkanoates, respectively, i.e. the 17,21-diacetate, the 17-acetate 21-propionate, 17-acetate 21-n-butyrate, 17-acetate 21-isobutyrate, and the 17-acetate 21-valerate of 16α-methyl-1,4,6-pregnatriene-11β,17α,21-triol-3,20-dione; the 17-n-butyrate 21-acetate, 17-n-butyrate 21-propionate, 17,21-di-n-butyrate, 17-n-butyrate 21-isobutyrate, 17-n-butyrate 21-valerate of 16α-methyl-1,4,6-pregnatriene-11β,17α,21-triol-3,20-dione; the 17-isobutyrate 21-acetate, 17-isobutyrate 21-propionate, 17-isobutyrate 21-n-butyrate, 17,21-diisobutyrate, and the 17-isobutyrate 21-valerate of 16α-methyl-1,4,6-pregnatriene-11β,17α,21-triol-3,20-dione; the 17-benzoate 21-acetate, 17-benzoate 21-propionate, 17-benzoate 21-n-butyrate, 17-benzoate 21-isobutyrate, 17-benzoate 21-isovalerate of 16α-methyl-1,4,6-pregnatriene-11β,17α,21-triol-3,20-dione; the 17-valerate 21-acetate, 17-valerate 21-propionate, 17-valerate 21-n-butyrate, 17-valerate 21-isobutyrate, and 17,21-divalerate of 16α-methyl-1,4,6-pregnatriene-11β,17α,21-triol-3,20-dione.

In a manner similar to that described in Preparation 1C treat each of the 16α-methyl-1,4,6-pregnatriene-11β,17α,21-triol-3,20-dione 17-monoester starting compounds of Preparation 3B(1) in pyridine with each of benzoyl chloride, p-toluyl chloride, p-fluorobenzoyl chloride and 3',5'-dimethylbenzoyl chloride to obtain the corresponding 21-benzoate of substituted benzoate ester, i.e. the 21-benzoate, 21-p-toluate, 21-p-fluorobenzoate, and 21-(3',5'-dimethylbenzoate) of each of the 16α-methyl-1,4,6-pregnatriene-11β,17α,21-triol-3,20-dione 17-monoester starting compounds.

PREPARATION 4

THE 17-ESTERS, 21-ESTERS, AND 17,21-DIESTERS OF 16β-METHYL-1,4,6-PREGNATRIENE-11β,17α,21-TRIOL-3,20-DIONE AND OF 16α-METHYL-1,4,6-PREGNATRIENE-17α,21-DIOL-3,11,20-TRIONE AND THE 16β-METHYL EPIMERS THEREOF (1) In the procedure of Preparation 1A by utilizing as starting compound 16β-methyl-1,4-pregnadiene-11β,17α,21-triol-3,20-dione 21-acetate, there is obtained 16β-methyl-1,4,6-pregnatriene-11β,17α,21-triol-3,20-dione 21-acetate which, when carried through the sequence of reactions described in Preparations 1-3, will produce the 16β-methyl epimers of the 16α-methyl products described therein.

(2) In similar manner, in the procedure of Preparation 1A by utilizing as starting compound 16α-methyl-1,4-pregnadiene-17α,21-diol-3,11,20-trione 21-acetate, there is obtained 16α-methyl-1,4,6-pregnatriene-17α,21-diol-3,11,20-trione 21-acetate which, when carried through the sequence of reactions described in Preparations 1-3, will produce 11-oxo-16α-methyl pregnatriene derivatives corresponding to the 11β-hydroxy-16α-methyl pregnatriene products named therein.

(3) In the procedure of Preparation 1A by utilizing as starting compound 16β-methyl-1,4-pregnadiene-17α,21-diol-3,11,20-trione 21-acetate, there is obtained 16β-methyl-1,4,6-pregnatriene-17α,21-diol-3,11,20-trione 21-acetate which, when carried through the sequence of reactions described in Preparations 1-3, will produce the 11-oxo-16β-methyl pregnatriene derivatives corresponding to the 11β-hydroxy-16α-methyl pregnatriene products named therein.

PREPARATION 5

ALTERNATE PROCEDURE FOR PREPARING 1,4,6-PREGNATRIENE-17α,21-DIOL-3,11,20-TRIONES AND 17,21-DIESTERS THEREOF

A. 6β-Bromo-16α-Methyl-1,4-Pregnadiene-17α,21-Diol-3,11,20-Trione 21-Acetate

To a solution of 16α-methyl-1,4-pregnadiene-17α,21-diol-3,11,20-trione 21-acetate (11 gms.) in carbon tetrachloride (110 ml.) and chlorobenzene (110 ml.) at reflux temperature, add N-bromosuccinimide (7 gms.) followed by azobisisobutyronitrile (530 mg.). Heat at reflux temperature for 30 minutes, cool, add with stirring 300 ml. of a 10% aqueous sodium bisulfite solution. Add chloroform (150 ml.), separate the organic layer, wash with water and dry over anhydrous magnesium sulfate. Evaporate in vacuo to a residue comprising 6β-bromo-16α-methyl-1,4-pregnadiene-17α,21-diol-3,11,20-trione.

B. 16α-Methyl-1,4,6-pregnatriene-17α,21-Diol-3,11,20-Trione 21-Acetate

To a solution of 6β-bromo-16β-bromo-16α-methyl-1,4-pregnadiene-17α,21-diol-3,11,20-trione 21-acetate prepared in Preparation 5A in dimethylacetamide (125 ml.) add lithium bromide (4.4 gms.) and calcium carbonate (7.75 gms.). Heat the reaction mixture at at 120° C under an atmosphere of nitrogen for 1 hour. Cool, filter and dilute the filtrate with chloroform (500 ml.). Wash the chloroform solution with water, dry over magnesium sulfate and evaporate to a residue comprising 16α-methyl-1,4,6-pregnatriene-17α,21-diol-3,11,20-trione 21-acetate.

C. 16α-Methyl-1,4,6-pregnatriene-17α,21-Diol-3,11,20-Trione

In a manner similar to that described in Preparation 1B treat 16α-methyl-1,4,6-pregnatriene-17α,21-diol-3,11,20-trione 21-acetate with aqueous sodium bicarbonate in methanol and isolate the resultant product in a manner similar to that described to obtain 16α-methyl-1,4,6-pregnatriene-17α,21-diol-3,11,20-trione.

D. 16α-Methyl-1,4,6-Pregnatriene-17α,21-Diol-3,11,20-Trione 17,21-Dialkanoate (1) Stir at room temperature for 1 hour a solution of trifluoroacetic anhydride (8 ml.), propionic acid (200 ml.) and p-toluene sulfonic acid monohydrate (200 mg.), then add 16α-methyl-1,4,6-pregnatriene-17α,21-diol-3,11,20-trione (2 gms.). Stir the reaction mixture for 17 hours, then add an additional 6 ml. of trifluoroacetic anhydride. Continue stirring for 5 hours, then pour into water (400 ml.) containing 1 N sodium hydroxide (200 ml.). Extract the aqueous mixture with chloroform, wash the combined chloroform extracts with water, dry over magnesium sulfate and evaporate in vacuo. Dissolve the resultant residue in methanol and steam distill to remove the volatile impurities. Decant the water from the residue of the distillation and dry the residue to obtain 16α-methyl-1,4,6-pregnatriene-17α,21-diol-3,11,20-trione 17,21-dipropionate.

(2) In the above procedure, by substituting for propionic acid equivalent quantities of other alkanoic acids, e.g. acetic acid, valeric acid and n-butyric acid there is obtained the corresponding 17,21-dialkanoate, e.g. the 17,21-diacetate, 17,21-divalerate, and 17,21-dibutyrate of 16α-methyl-1,4,6,-pregnatriene-17α,21-diol-3,11.20-trione.

PREPARATION 6

16α,17α-ISOPROPYLIDENEDIOXY-1,4,6,-PREGNATRIENE-11β,21-diol-3,20-DIONE (1) In a manner similar to that described in Preparation 3A, treat 16α,17α-isopropylidenedioxy-1,4-pregnadiene-11β,21-diol-3,20-dione with acetic anhydride in pyridine and isolate the resultant product to obtain 16α,17α-isopropylidenedioxy-1,4,-pregnadiene-11β,21-diol-3,20-dione 21-acetate.

(2) In a manner similar to that described in Preparation 1A, treat 16α,17α-isopropylidenedioxy-1,4-pregnadiene -11β,21-diol-3,20-dione 21-acetate with DDQ and dry hydrogen chloride in dioxane and isolate the resultant product to obtain 16α,17α-isopropylidenedioxy-1,4,6-pregnatriene-11β,21-diol-3,20-dione 21-acetate.

PREPARATION 7

21-HALOGENO-1,4,6-PREGNATRIENE-11β,17α-DIOL-3,20-DIONE 17-HYDROCARBONCARBOXYLATES

A. 21-Halogeno-1,4-Pregnadiene-11β,17α-Diol-3,20-Dione 17-Hydrocarboncarboxylates (1) 16α-Methyl-21-Chloro-1,4-Pregnadiene-11β,17α-Diol-3,20-Dione 17-Propionate To a solution of 16α-methyl-1,4-pregnadiene-11β,17α,21-triol-3,20-dione 17,21-n-butylorthopropionate (0.87 gms.) in chloroform (87 ml.) add trimethylsilyl chloride (1.15 ml.) and heat at reflux temperature for 24 hours. Evaporate the reaction mixture in vacuo and place the resultant residue on a silica gel column (80 gms.) eluting with chloroform:ethyl acetate (2:1). Evaporate the combined eluates to a residue comprising 16α-methyl-21-chloro-1,4-pregnadiene-11β,17α-diol-3,20-dione 17-propionate.

(2) 16α-Methyl-21-Bromo-1,4-Pregnadiene-11β,17α-Diol-3,20-Dione 17-Propionate

In the above procedure, by utilizing trimethylsilyl bromide as reagent, there is obtained the corresponding 21-bromo derivative, i.e. 16α-methyl-21-bromo-1,4-pregnadiene-11β,17α-diol-3,20-dione 17-propionate.

(3) Treat each of the following with trimethylsilyl chloride in the manner described in Preparation 7A(1): 16α-methyl-1,4-pregnadiene-11β,17α,21-triol-3,20-dione 17,21-ethylorthoacetate, 16α-methyl-1,4-pregnadiene-11β,17α,21-triol-3,20; -dione 17,21-ethylortho-n-butyrate, 16α-methyl-1,4-pregnadiene-11β,17α,21-triol-3,20-dione 17,21-n-butylorthovalerate, and 16α-methyl- 1,4-pregnadiene-11β,17α,21-triol-3,20-dione 17m21-methylorthobenzoate. Isolate and purify each of the resultant products in a manner similar to that described to obtain, respectively, 16α-methyl-21-chloro-1,4-pregnadiene-11β,17α-diol-3,20-dione 17-acetate, 16α-,etju;-21-chloro-1,4-pregnadiene-11β,17α,-diol-3,20-dione 17-n-butyrate, 16α-methyl-21-chloro-1,4-pregnadiene-11β,17α-diol-3,20-dione 17-valerate, and 16α-methyl-21-chloro-1,4-pregnadiene-11ε,17α-diol-3,20-dione 17-benzoate.

In the above procedure, by utilizing trimethylsilyl bromide as reagent, there is obtained the 21-bromo derivatives corresponding to each of the 21-chloro derivatives.

(4) In the procedures of Preparation 7A(1)- 7A(3), by utilizing as starting steroids the 16β-methyl epimer of the 16α-methyl compounds named therein, there is obtained the corresponding 16β-methyl epimer of the 21-halogeno pregnadiene products named therein. Similarly, by starting with derivatives having an 11-oxo function instead of an 11β-hydroxyl function, there are obtained the corresponding 21-halogeno derivatives containing an 11-oxo function.

B. 16α-Methyl-21-Halogeno-1,4,6-Pregnatriene-11β,17α-Diol-3,20-Dione 17-Alkanoate (1) 16α-Methyl-1,4,6-pregnatriene-11β,17α-Diol-3,20-Dione 17-Propionate Treat each of 16α-methyl-21-chloro-1,4-pregnadiene-11β,17α-diol-3,20-dione 17-propionate and 16α-methyl-21-bromo-11β,17α-diol-3,20-dione 17-propionate with DDQ and dry hydrogen chloride in dioxane in the manner described in Preparation 1A to obtain, respectively, 16α-methyl-21-chloro-1,4,6-pregnatriene-11β,17α-diol-3,20-dione 17-propionate and 16α-methyl-21-bromo-1,4,6-pregnatriene-11β,17α-diol-3,20-dione 17-propionate.

(2) In similar manner, treat each of the 1,4-pregnadiene-21-halogeno products of Preparation 7A(3) and 7A(4) with DDQ in dry hydrogen chloride in dixoane to obtain the corresponding 1,4,6-pregnatriene derivative.

(3) 16α-Methyl-21-Fluoro-1,4,6-Pregnatriene-11β,17α-Diol-3,20-Dione 17-Propionate In a manner similar to that described in Preparation 1C, treat 16α-methyl-1,4,6-pregnatriene-11β,17α,21-triol-3,20-dione 17-propionate with methanesulfonyl chloride in pyridine to obtain 16α-methyl-1,4,6-pregnatriene-11β,17α-diol-3,20-dione 17-propionate 21-methanesulfonate.

Treat the foregoing 21-methanesulfonate ester derivative with silver fluoride in acetonitrile according to known procedures to obtain 16α-methyl-21-fluoro-1,4,6-pregnatriene-11β,17α-diol-3,20-dione 17-propionate.

PREPARATION 8

1,4,6-PREGNATRIENE-11β,17α-DIOL-3,20-DIONE 17-HYDROCARBONCARBOXYLATES

A. 1,4-Pregnadiene-11β,17α-Diol-3,20-Dione 17-Hydrocarboncarboxylates (1) To 1,4-pregnadiene-11β,17α,21-triol-3,20-dione 17,21-ethylorthopropionate (4gms.) in methylene chloride (100 ml.) under at atmosphere of nitrogen at 0° C add trimethylsilyl iodide (3.68 ml.) and, after 1 minute, pour the reaction mixture into 1.0 N sodium thiosulfate solution (300 ml.) with efficient stirring. Extract the reaction mixture with methylene chloride, wash with water, dry over magnesium sulfate and evaporate. Purify the resultant residue on a column of silica gel (300 gms.) eluting with chloroform:ethyl acetate (4:1) to obtain 1,4-pregnadiene-11β,17α-diol-3,20-dione 17-propionate.

(2) In similar manner, treat each of 1,4-pregnadiene-11β,17α,21-triol-3,20-dione 17,21-ethylortho-n-butyrate, 1,4-pregnadiene-11β,17α,21-triol-3,20-dione 17,21-n-butylorthovalerate, 1,4-pregnadiene-11β,17α,21-triol-3,20-dione 17,21-ethylorthoacetate, and 1,4-pregnadiene-11β,17α,21-triol-3,20-dione 17,21-methylorthobenzoate with trimethylsilyl iodide followed by the immediate isolation of the resultant product to obtain, respectively, the 17-n-butyrate, the 17-valerate, the 17-acetate, and the 17-benzoate of 1,4-pregnadiene-11β,17α-diol-3,20-dione.

B. 1,4,6-Pregnatriene-11β,17α-Diol-3,20-Dione 17-Hydrocarboncarboxylates

In a manner similar to that described in Preparation 1A, treat each of the 1,4-pregnadiene 17-ester products of Preparation 8A with DDQ and hydrogen chloride in dioxane to obtain, respectively, 1,4,6-pregnatriene-11β,17α-diol-3,20-dione 17-propionate, 1,4,6-pregnatriene-11β,17α-diol-3,20-dione 17-n-butyrate, 1,4,6-pregnatriene-11β,17α-diol-3,20-dione 17-valerate, 1,4,6,-pregnatriene-11β,17α-diol-2,20-dione 17-acetate and 1,4,6-pregnatriene-11β,17α-diol-3,20-dione 17-benzoate.

PREPARATION 9

16-METHYLENE-1,4,6PREGNATRIENE-11β,17α,21-TRIOL-3,20-DIONE 21-HYDROCARBONCARBOXYLATES AND 17,21-DIHYDROCARBONCARBOXYLATES

A. 16-Methylene-1,4-Pregnadiene-11β,17α,21-Triol-3,20-dione 21-Hydrocarboncarboxylate (1) In a manner similar to that described in Preparation 3A(1), treat 16-methylene-1,4-pregnadiene-11β,17α,21-triol-3,20-dione (5 gms.) in pyridine (100 ml.) with propionic acid anhydride (10 ml.). Isolate and purify the resultant product in a manner similar to that described to obtain 16-methylene-1,4-pregnadiene-11β,17α,21-triol-3,20-dione 21-propionate.

(2) In the above procedure, by using other alkanoic acid anhydrides in place of propionic acid anhydride, e.g. acetic anhydride, n-butyric anhydride, and valeric anhydride, there is obtained the corresponding 21-lower alkanoic ester, e.g. the 21-acetate, 21n-butyrate, and 21-valerate of 16-methylene-1,4-pregnadiene-11β,17α,21-triol-3,20-dione.

(3) Similarly, by treating 16-methylene-1,4-pregnadiene-11β,17α,21-triol-3,20-dione with benzoyl chloride in a manner similar to that described in Preparation 1C, there is obtained 16-methylene-1,4-pregnadiene-11β,17α,21-triol-3,20-dione 21-benzoate.

B. 16-Methylene-1,4-Pregnadiene-11β,17α,21-Triol-3,20-Dione 11-Trifluoroacetate 21-Propionate (1) To a solution of 16-methylene-1,4-pregnadiene-11β,17α,21-triol-3,20-dione 21-propionate (1 gm.) in pyridine (10 ml.) cool to −23° C, add trifluoroacetic anhydride (1 ml.) precooled to −23° C. Allow the reaction mixture to stand at −23° C for 40 minutes, then pour into ice water (200 ml.) containing concentrated hydrochloric acid (8.8 ml.). Separate the resultant precipitate by filtration, wash with water and dry to give 16-methylene-1,4-pregnadiene-11β,17α,21-triol-3,20-dione 11-trifluoroacetate 21-propionate.

(2) In similar manner by treating each of 21-hydrocarboncarboxylates prepared in Preparation 9A(2) and (3), there is obtained the corresponding 11-trifluoroacetate ester thereof.

C. 16-Methylene-1,4-Pregnadiene-11β,17α,21-Triol-3,20-Dione 11-Trifluoroacetate 17,21-Dihydrocarboncarboxylate To a solution of 16-methylene-1,4-pregnadiene-11β,17α,21-triol-3,20-dione 11-trifluoroacetate 21-propionate (1.07 gms.) in propionic acid (10 ml.), contanining p-toluenesulfonic acid monohydrate (0.1 gm.) at 0° C, add trifluoroacetic anhydride (4ml.) dropwise. Allow the reaction mixture to stand at 0° C for 5 minutes, then warm to room temperature and let remain at room temperature for 3 hours. Pour the reaction mixture into water, extract the aqueous mixture with ethyl acetate, wash the combined organic extracts with 5% sodium hydroxide then with water, dry over magnesium sulfate and evaporate to a residue comprising 16-methylene-1,4-pregnadiene-11β,17α,21-triol-3,20-dione 11-trifluoroacetate 17,21-dipropionate.

(2) In similar manner, treat each of the 11-trifluoroacetate esters prepared in Preparation 9B(2 ) in the manner described above to obtain the corresponding 17-propionate ester, i.e. the 17-propionate 21-acetate, the 17-propionate 21-n-butyrate, the 17-propionate 21-valerate and the 17-propionate 21-benzoate of 16-methylene-1,4-pregnadiene-11β,17α,21-triol-3,20-dione 11-trifluoroacetate.

(3) In the procedure of Preparation 9C(1), by substituting for propionic acid other hydrocarboncarboxylate acids, e.g. n-butyric acid and acetic acid, there is obtained, respectively, 16-methylene -1,4-pregnadiene-11β,17α,21-triol-3,20-dione 11-trifluoroacetate 17-n-butyrate 21-propionate and 16-methylene-1,4-pregnadiene-11β,17α,21-triol-3,20-dione 11-trifluoroacetate 17-acetate 21-propionate.

(4) In a manner similar to that described in Preparation 9C(3), by utilizing as starting compounds the products of Preparation 9B(2), there is obtained the corresponding 17-n-butyrate and 17-acetate esters thereof.

D. 16-Methylene-1,4,6-Pregnatriene-11β,17α,21-Triol-3,20-Dione 11-Trifluoroacetate 17,21-Dihydrocarboncarboxylate (1) In a manner similar to that described in Preparation 1A, treat 16-methylene-1,4-pregnadiene-11β,17α,21-triol-3,20-dione 11-trifluoroacetate 17,21-dipropionate with dry hydrogen chloride and DDQ to obtain 16-methylene-1,4,6-pregnatriene-11β,17α,21-triol-3,20-dione 11-trifluoroacetate 17,21-dipropionate.

(2) In similar manner, treat each of the products of Preparations 9C(2) - (4) with DDQ in dry hydrogen chloride in dixoane to obtain the corresponding 6-dehydro analog thereof.

E. 16-Methylene-1,4,6-Pregnatriene-11β,17α,21-Triol-3,20-Dione 17,21-Dipropionate (1) To a solution of 16-methylene-1,4,6-pregnatriene-11β,17α,21-triol-3,20-dione 11-trifluoroacetate 17,21-dipropionate (0.52 gms.) in methanol (26 ml.) add sodium benzoate (1.5 gms.) and stir at room temperature for 2½ hours. Evaporate the solution in vacuo at room temperature and wash the resultant residue thoroughly with water. Separate the solids by filtration and dry to obtain 16-methylene-1,4,6-pregnatriene-11β,17α,21-triol-3,20-dione 17,21-dipropionate. Additional product is obtained by extracting the combined water washes and filtrate with ethyl acetate, washing the organic extract with water, drying over magnesium sulfate and evaporating to obtain a residue of 16-methylene-1,4,6-pregnatriene-11β,17α,21-triol-3,20-dione 17,21-dipropionate.

(2) In similar manner, treat each of the 11-trifluoroacetate products of Preparation 9D(2) in methanol with sodium benzoate to obtain the corresponding 11β-hydroxy derivative.

PREPARATION 10

16-METHYLENE-1,4,6-PREGNATRIENE-17α,21-DIOL-3,11,20-TRIONE 17,21-DIHYDROCARBONCARBOXYLATES

A. 16-Methylene-1,4-Pregnadiene-17α,21-Diol-3,11,20-Trione 17,21-Alkylorthohydrocarboncarboxylates (1) In a manner similar to that described in Preparation 2C(1), treat 16-methylene-1,4-pregnadiene-17α,21-diol-3,11,20-trione in dioxane and benzene with pyridinium p-toluenesulfonate and trimethylorthobenzoate. Isolate and purify the resultant product in a manner similar to that described to obtain 16-methylene-1,4-pregnadiene-17α,21-diol-3,11,20-trione 17,21-methylorthobenzoate.

(2) In a manner similar to that described in Preparation 2A(2), treat 16-methylene-1,4-pregnadiene-17α,21-diol-3,11,20-trione in dimethylsulfoxide in the presence of p-toluenesulfonic acid with each of triethylorthopropionate, triethylortho-n-butyrate, and tri-n-butylorthovalerate, to obtain the corresponding 17,21-alkylorthoalkanoate, e.g. the 17,21-ethylorthopropionate and 17,21-ethylortho-n-butyrate, and 17,21-n-butylorthovalerate, respectively, of 16-methylene-1,4-pregnadiene-17α,21-diol-3,11,20-trione.

B. 16-Methylene-1,4-Pregnadiene-17α,21-Diol-3,11,20-Trione 17-Hydrocarboncarboxylates (1) Dissolve 16-methylene-1,4-pregnadiene-17α,21-diol-3,11,20-trione 17,21-methylorthobenzoate (2 gms.) in glacial acetic acid (15 ml.) and water (0.3 ml.). Allow to stand at room temperature for 20 minutes, then pour into water (300 ml.) and add an 8% sodium hydroxide solution (50 ml.). Separate the resultant precipitate by filtration, wash with water and dry at room temperature. Isolate the desired compound via preparative thin layer chromatography on silica gel utilizing as developing solvent a mixture of ethyl acetate:chloroform (1:1). Remove the most polar band as visualized by ultraviolet light and elute with ethyl acetate. Evaporate to a residue comprising 16-methylene-1,4-pregnadiene-17α,21-diol-3,11,20-trione 17-benzoate.

(2) Treat each of the 17,21-alkylorthoalkanoates prepared in Preparation 10A(2) with aqueous acetic acid in the manner described above to obtain, respectively, the 17-propionate, 17-n-butyrate, and the 17-valerate of 16-methylene-1,4-pregnadiene-17α,21-diol-3,11,20-trione.

C. 16-Methylene-1,4-Pregnadiene-17α,21-Diol-3,11,20-trione 17,21-Dihydrocarboncarboxylates (1) Treat each of the 16-methylene-1,4-pregnadiene-17α,21-diol-3,11,20-trione 17-hydrocarboncarboxylates prepared in Preparation 10B with benzoyl chloride in pyridine according to the procedure of 1C to obtain, respectively, the 17α,21-dibenzoate, the 17-propionate 21-benzoate, the 17-n-butyrate 21-benzoate and the 17-valerate 21-benzoate of 16-methylene-1,4-pregnadiene-17α,21-diol-3,11,20l-trione.

(2) In a manner similar to that described in Preparation 3A(1), treat each of the 17-hydrocarboncarboxylates of 16-methylene-1,4-pregnadiene-17α,21-diol-3,11,20-trione of Preparation 10B in pyridine with propionic acid anhydride to obtain, respectively, the 17-benzoate 21-propionate, the 17,21-dipropionate, the 17-n-butyrate 21-priopionate, and the 17-valerate 21-propionate of 16-methylene-1,4-pregnadiene-17α,21-diol-3,11,20-trione.

D. 16-Methylene-1,4,6-Pregnatriene-17α,21-Diol-3,11,20-Trione 17,21-Dihydrocarboncarboxylates In a manner similar to that described in Preparation 1A, treat each of the 16-methylene-1,4-pregnadienes prepared in Example 10C in dioxane with dry hydrogen chloride and DDQ, and isolate and purify each of the respective products to obtain the corresponding 1,4,6-pregnatrienes, i.e. the 17-benzoate 21-propionate, 17-benzoate 21-n-butyrate, 17-benzoate 21-valerate, 17-propionate 21-butyrate, 17,21-dipropionate, 17-n-butyrate 21-propionate, and 17-valerate 21-propionate.

PREPARATION 11

7α-HYDROXY-1,4-PREGNADIENE-3,20-DIONES

A. 9α-Fluoro-16α-Methyl-1,4-Pregnadiene-7β,11β,17α,21-Tetrol-3,20-Dione 21-Acetate (1) 9α-Fluoro-16α-Methyl-1,4-Pregnadiene-6β,7β,11β,17α,21-Pentol-3,20-Dione 21-Acetate To 9α-fluoro-16α-methyl-1,4,6-pregnatriene-11β,17α,21-triol 21-acetate (8.3 gms.) in dioxane (350 ml.) and pyridine (5 ml.) add osmium tetroxide (4.9 gms.). Stir the reaction mixture at room temperature for 5 days, then saturate the solution with hydrogen sulfide and filter the reaction solution through Celite. Evaporate the filtrate in vacuo at room temperature and triturate the resultant residue with chloroform:methanol and separate the resultant precipitate by filtration to obtain 9α-fluoro-16α-methyl-1,4-pregnadiene-6β,7β,11β,17α,21-pentol-3,20-dione 21-acetate.

(2) 9α-Fluoro-16α-Methyl-1,4-Pregnadiene-6β,7β,11β,17α,21-Pentol-3,20-Dione 6,7-n-butylorthopropionate 21-Acetate To 9α-fluoro-16α-methyl-1,4-pregnadiene-6β,7β,11β,17α,21-pentol-3,20-dione 21-acetate (3 gms.) in dimethylsulfoxide (15 ml.) add tri-n-butylorthopropionate (5.4 ml.) and P-toluenesulfonic acid monohydrate (0.225 gms.) and stir at room temperature for 3.5 hours. Pour the reaction mixture into water (500 ml.) and saturated aqueous sodium bicarbonate (100 ml.). Extract the aqueous mixture with ethyl acetate, wash the combined extracts with water, dry over magnesium sulfate and evaporate to a residue comprising 9α-fluoro-16α-methyl-1,4-pregnadiene-6β,7β,11β,17α,21-pentol-3,20-dione 6,7-n-butylorthopropionate 21-acetate.

(3) 9α-Fluoro-16α-Methyl-1,4-Pregnadiene-6β,7β,11β,17α,21-Pentol-3,20-Dione 6-Propionate 21-Acetate Dissolve the product of Preparation 11A(2) in glacial acetic acid (50 ml.) and water (1 ml.). Allow the reaction mixture to stand at room temperature for 1 hour, then pour into ice water (500 ml.) and separate the resultant precipitate by filtration. Wash the precipitate with water and dry at room temperature to give 9α-fluoro-16α-methyl-1,4-pregnadiene-6β,7β,11β,17α,21-pentol-3,20-dione 6-propionate 21-acetate.

(4) 9α-Fluoro-16α-Methyl-1,4-Pregnadiene-7β,11β,17α,21-Tetrol-3,20-Dione 21-Acetate To 9α-fluoro-16α-methyl-1,4-pregnadiene-6β,7β,11β,17α,21-pentol-3,20-dione 6-propionate 21-acetate (3 gms.) in acetone (750 ml.) add a solution of sodium acetate (21 gms.), water (60 ml.) and acetic acid (15 ml.) followed by chromous acetate sludge (freshly prepared from 70 gms. of chromic chloride reduced by zinc amalgam followed by treatment with sodium acetate according to known procedures). Stir the reaction mixture at room temperature for 2½ hours, filter and evaporate. Add water to the resultant residue, extract with ethyl acetate, wash the combined organic extracts with water, dry and evaporate in vacuo to a residue comprising 9α-fluoro-16α-methyl-1,4-pregnadiene-7β,11β,17α,21-tetrol-3,20-dione 21-acetate. Purify by crystallization from acetone:hexane; m.p. 181°–185° C; $[\alpha]_D^{26}$ +48.7° (dimethylformamide).

B. Similarly, treat each of 9α-chloro-16α-methyl-1,4,6-pregnatriene-11β,17α,21-triol-3,20-dione 21-acetate, 9α-bromo-16α-methyl-1,4,6-pregnatriene-11β,17α,21-triol-3,20-dione 21-acetate and 16α-methyl-1,4,6-pregnatriene-11β,17α,21-triol-3,20-dione 21-acetate in a manner similar to that described in Preparation 11A to obtain, respectively, 9α-chloro-16α-methyl-1,4-pregnadiene-7β,11β,17α,21-tetrol-3,20-dione 21-acetate, 9α-bromo-16α-methyl-1,4-pregnadiene-7β,11β,17α,21-tetrol-3,20-dione 21-acetate and 16α-methyl-1,4-pregnadiene-7β,11β,17α,21-tetrol-3,20-dione 21-acetate.

C. (1) Similarly, by treating each of the pregnatrienes prepared in Preparations 1–8 according to the procedures described in Preparation 11A, there is obtained the corresponding 7β-hydroxy-1,4-pregnadiene derivative.

(2) Similarly, by treating each of the corresponding 9α-fluoro-, 9α-chloro-, and 9α-bromo- analogs of the 9-unsubstituted-1,4,6-pregnatrienes prepared in Preparations 1–8 according to the procedure of Preparation 11A, there is obtained the corresponding 7β-hydroxy-9α-fluoro-1,4-pregnadiene derivatives.

D. 7β-Hydroxy-16-Methylene-1,4-Pregnadienes (1) 16β-Methyl-16α,17α-Oxido-1,4-Pregnadiene-6β,7β,11β,21-Tetrol-3,20-Dione 21-Acetate In a manner similar to that described in Preparation 11A, treat 16β-methyl-16α,17α-oxido-1,4,6-pregnatriene-11β,21-diol-3,20-dione 21-acetate in dioxane and pyridine with osmium tetroxide. Isolate the resultant product in a manner similar to that described to obtain 16β-methyl-16α,17α-oxido-1,4-pregnadiene-6β,7β,11β,21-tetrol-3,20-dione 21-acetate.

(2) 16-Methylene-1,4-Pregnadiene-6β,7β,11β,17α,21-Pentol-3,20-Dione 21-Acetate

To a solution comprising 16β-methyl-16α,17α-oxido-1,4-pregnadiene-6β,7β,11β,21-tetrol 21-acetate (100 mg.) in acetic acid (1 ml.) and p-toluenesulfonic acid (10 mg.) at 5° C, add trifluoroacetic anhydride (0.1 ml.).

Allow the reaction mixture to stand at room temperature for 25 minutes, then pour into water and collect by filtration 16-methylene-1,4-pregnadiene-6β,7β,11β,17α,21-pentol-3,20-dione 21-acetate.

(3) 16-Methylene-1,4-Pregnadiene-7β,11β,17α,21-Tetrol-3,20-Dione 21-Acetate

Treat 16-methylene-1,4-pregnadiene-6β,7β,11β,17α,21-pentol-3,20-dione 21-acetate in a manner similar to that described in Procedures 11A(2), (3) and (4) to obtain 16-methylene-1,4-pregnadiene-7β,11β,17α,21-tetrol-3,20-dione 21-acetate.

(4) In similar manner, treat each of 16β-methyl-16α,17α-oxido-1,4,6-pregnatriene-21-ol-3,20-dione 21-acetate, the 9α-fluoro and 9α-chloro analogs thereof, and 9α-fluoro-16β-methyl-16α,17α-oxido-1,4,6-pregnatriene-11β,21-diol-3,20-dione 21-acetate and 16β-methyl-16α,17α-oxido-9α-chloro-1,4,6-pregnatriene-11β,21-diol-3,20-dione 21-acetate in a manner similar to that described in Preparations 11D(1)-(3) to obtain, respectively, 16-methylene-1,4-pregnadiene-7β,17α,21-triol-3,11,20-trione 21-acetate and the 9α-fluoro- and 9α-chloro- analogs thereof, and 9α-fluoro-16-methylene-1,4-pregnadiene-7β,11β,17α,21-tetrol-3,20-dione 21-acetate and 9α-chloro-16-methylene-1,4-pregnadiene-7β,11β,17α,21-tetrol-3,20-dione 21-acetate.

EXAMPLE 1

7α-CHLORO-16α-METHYL-1,4-PREGNADIENE-11β,17α,21-TRIOL-3,20-DIONE 17,21-DIPROPIONATE

A. Add 16α-methyl-1,4,6-pregnatriene-11β,17α,21-triol-3,20-dione 17,21-dipropionate (2.0 gms.) to dioxane (24 ml.) which has been saturated with dry hydrogen chloride gas. Stir at room temperature for 16 hours, pour into ice water (600 ml.), separate the resultant precipitate by filtration, wash the precipitate with water and dry in air. Separate the components in the foregoing precipitate on silica gel via thin layer chromatography utilizing as developing solvent ether:hexane (2:1), and elute with ethyl acetate the band containing 7α-chloro-16α-methyl-1,4-pregnadiene-11β,17α,21-triol-3,20-dione 17,21-dipropionate as shown by ultraviolet light. Evaporate the combined ethyl acetate eluates and triturate the resultant residue with acetone:ether, then filter and dry the triturated precipitate to obtain 7α-chloro-16α-methyl-1,4-pregnadiene-11β,17α,21-triol-3,20-dione 17,21-dipropionate.

Alternatively, the compound of this Example is prepared according to following procedures 1B and 1C.

B. 7α-Chloro-16α-Methyl-1,4-Pregnadiene-17α,21-Diol-3,11,20-Trione 17,21-Dipropionate Saturate dry tetrahydrofuran (137 ml.) at 0° C with dry hydrogen chloride gas. Add 16α-methyl-1,4,6-pregnatriene-17α,21-diol-3,11,20-trione 17,21-dipropionate (6.85 gms.) and stir the reaction mixture at 0° C for 1 hour. Pour into ice water (1 liter) and stir for ½ hour. Separate the resultant precipitate by filtration, wash with water, and air dry to give 7α-chloro-16α-methyl-1,4-pregnadiene-17α,21-diol-3,11,20-trione 17,21-dipropionate. Purify from methanol:acetone containing a trace of propylene oxide; $[\alpha]_D^{26}$ + 76.2° (dimethylformamide); $[M]^+$ 520, 518.

C. To a solution of 7α-chloro-16α-methyl-1,4-pregnadiene-17α,21-diol-3,11,20-trione 17,21-dipropionate (3.2 gms.) in tetrahydrofuran (24 ml.) and methanol (8 ml.) at 0° C under an atmosphere of nitrogen add sodium borohydride (0.697 gms.) and stir the reaction mixture for 15 minutes at 0° C. Pour into ice water (1.8 liters) and 250 ml. of 1 N hydrochloric acid. Separate the resultant precipitate by filtration and air dry to give 7α-chloro-16α-methyl-11β,17α,21-triol-3,20-dione 17,21-dipropionate. Purify by crystallizing twice from acetone:methanol:isopropyl ether; m.p. 212°–216° C; $[\alpha]_D^{26}$ + 42.6° (dimethylformamide); $[M]^+$ 522, 520; $\lambda_{max}^{methanol}$ 242 nm (ε15,600); $\nu_{max}^{nujol}$ 1743, 1730, 1720, 1652, 1610, 1595 cm$^{-1}$; nmr (dmso-d$_6$) δ 0.84 (C$_{16}$-CH$_3$, d J7Hz), 1.02 (C$_{13}$-CH$_3$, s), 1.42 (C$_{10}$-CH$_3$, s), 4.38 (11α-H, mult.), 4.67 (7β-H, mult.), 4.80 (C$_{21}$-H, s), 5.95 (C$_4$-H, s), 6.20 (C$_2$-H, dd J10,2Hz), 7.35 (C$_1$-H, d J10Hz).

EXAMPLE 2

7α-BROMO-16α-METHYL-1,4-PREGNADIENE-11β,17α,21-TRIOL-3,20-DIONE 17,21-DIPROPIONATE

A. Add 16α-methyl-1,4,6-pregnatriene-11β,17α,21-triol-3,20-dione 17,21-dipropionate (0.29 gms.) to a solution of 30% (w/v) dry hydrogen bromide in acetic acid (4 ml.) precooled to 0° C. Stir the reaction mixture at 0° C for 1 hour, pour into ice water, separate the resultant solids by filtration, wash the precipitate with water and dry. Purify by triturating with acetone:ether and drying the triturated precipitate to obtain 7α-bromo-16α-methyl-1,4-pregnadiene-11β,17α,21-triol-3,20-dione 17,21-dipropionate.

Alternatively, the compound of this example is prepared according to following procedures 2B and 2C.

B. 7α-Bromo-16α-Methyl-1,4-Pregnadiene-17α,21-Diol-3,11,20-Trione 17,21-Dipropionate To a solution of 16α-methyl-1,4,6-pregnatriene-17α,21-diol-3,11,20-trione 17,21-dipropionate (0.5 gms.) in glacial acetic acid (2 ml.), at 0° C, add a solution of dry hydrogen bromide gas (3 gms.) in glacial acetic acid (8 ml.) freshly prepared at 0° C. Stir the reaction mixture for 1 hour at 0° C, pour into ice water (400 ml.), stir for 30 minutes, then separate the resultant precipitate by filtration, wash the precipitate with water until the water washings are neutral, air dry the precipitate to obtain 7α-bromo-16α-methyl-1,4-pregnadiene-17α,21-diol-3,11,20-trione 17,21-dipropionate.

C. To a mixture of 7α-bromo-16α-methyl-1,4-pregnadiene-17α,21-diol-3,11,20-trione 17,21-dipropionate (2.84 gms.) and sodium borohydride (0.573 gms.) under an atmosphere of nitrogen at 0° C add methanol (8 ml.) precooled to 0° C and stir the reaction mixture for 5 minutes at 0° C. Pour the reaction mixture into ice water (2 liters) and 1 N hydrochloric acid (300 ml.), separate the resultant precipitate by filtration, wash the precipitate with water and air dry to obtain 7α-bromo-16α-methyl-1,4-pregnadiene-11β,17α,21-triol-3,20-dione 17,21-dipropionate. Purify by crystallization from acetone:ether:hexane; m.p. > 295° C; $[\alpha]_D^{26}$ + 37.3° (dimethylformamide); $\lambda_{max}^{methanol}$ 242 nm (ε 15,350); $\nu_{max}^{nujol}$ 1743, 1735, 1660, 1612, 1600 cm$^{-1}$; nmr (dmso-d$_6$) δ 0.85 (C$_{16}$-CH$_3$, d J7Hz), 1.03 (C$_{13}$-CH$_3$, s), 1.43 (C$_{10}$-CH$_3$, s), 4.38 (11α-H, mult.), 4.75 (7β-H, mult.), 4.81 (C$_{21}$-H, s), 5.86 (C$_4$-H, s), 6.19 (C$_9$-H, dd J10,2Hz), 7.31 (C$_1$-H, d J10 Hz).

EXAMPLE 3

7α-BROMO-16α-METHYL-1,4-PREGNADIENE-11β,17α,21-TRIOL-3,20-DIONE 17-BENZOATE 21-ACETATE

A. To 16α-methyl-1,4,6-pregnatriene-11β,17α, 21-triol-3,20-dione 17-benzoate 21-acetate (0.31 gms.) add a solution of 30% dry hydrogen bromide in glacial acetic acid (6.2 ml.) at 0° C. Pour into ice water, separate the resultant precipitate by filtration, wash the precipitate with water, and air dry. Purify the precipitate via thin layer chromatography on silica gel using as developing solvent ether:hexane (2:1) and eluting with ethyl acetate the band containing the desired product as shown by ultraviolet light. Evaporate the combined ethyl acetate eluates to a residue comprising 7α-bromo-16α-methyl-1,4-pregnadiene-11β,17α,21-triol-3,20-dione 17-benzoate 21-acetate. Further purify by triturating the residue with isopropyl ether.

Alternatively, the compound of this example is prepared according to following procedures 3B and 3C.

B. 7α-Bromo-16α-Methyl-1,4-Pregnadiene-17α,21-Diol-3,11,20-Trione 17-Benzoate 21-Acetate To a freshly prepared solution of dry hydrogen bromide gas (9.3 gms.) in glacial acetic acid (16 ml.) at 0° C add dropwise a solution of 16α-methyl-1,4,6-pregnatriene-17α,21-diol-3,11,20-trione 17-benzoate 21-acetate (1.56 gms.) in glacial acetic acid (5 ml.) Stir the reaction for 1 hour at 0° C, pour into ice water, stir the aqueous mixture for 30 minutes, then separate the resultant precipitate by filtration, wash the precipitate with water, and air dry to give 7α-bromo-16α-methyl-1,4-pregnadiene-17α,21-diol-3,11,20-trione 17-benzoate 21-acetate. Further purify by crystallization from acetone:hexane; m.p. 190°–192.5°; $[\alpha]_D^{26}$ + 77.3° (dimethylformamide); $\lambda_{max}^{methanol}$ 232 nm ($\epsilon$ 27,600).

C. (1) To a mixture of 7α-bromo-16α-methyl-1,4-pregnadiene-17α,21-diol-3,11,20-trione 17-benzoate 21-acetate (1.05 gms.) and sodium borohydride (0.1 gms.) under an atmosphere of nitrogen at 0° C, add a precooled solution of tetrahydro-furan (7.5 ml.) and methanol (2.5 ml.) and stir the reaction mixture for 25 minutes at 0° C. Pour into ice water (500 ml.) and 1 N hydrochloric acid (100 ml.). Separate the resultant precipitate by filtration, wash the precipitate with water and air dry to obtain 7α-bromo-16α-methyl-1,4-pregnadiene-11β,17α,21-triol-3,20-dione 17-benzoate 21-acetate. Further purify by crystallization from acetone:hexane:ether, m.p. 156°–159° C; $[\alpha]_D^{26}$ + 21.1° (dimethylformamide); $\lambda_{max}^{methanol}$ 233 nm ($\epsilon$26,800); nmr (dmso-D$_6$) δ0.89 (C$_{16}$-CH$_3$, d J7Hz), 1.12 (C$_{13}$-CH$_3$, s), 1.48 (C$_{10}$-CH$_3$, s), 2.13 (OAc, s), 4.46 (11α-H, mult.), 4.96 (C$_{21}$-H, quart. 4.90 (7β-H, mult.), 6.00 (C$_4$-H, s), 6.28 (C$_2$-H, d,d J10,2Hz), 7.39 (C$_1$-H, d, J10Hz), 7.50–8.00 (phenyl, mult.). (2) Alternatively, the compound of this example is prepared as follows. To a mixture of 7α-bromo-16α-methyl-1,4-pregnadiene-17α,21-diol-3,11,20 -trione 17-benzoate 21-acetate (0.65 gms.) and sodium borohydride (61.7 mg.) under an atmosphere of nitrogen at room temperature, add dimethylformamide (6.2 ml.) and water (0.3 ml.). Stir at room temperature under an atmosphere of nitrogen for 1 hour, pour into a mixture of water (200 ml.) and 1 N hydrochloric acid (50 ml.). Separate the resultant precipitate by filtration, wash the precipitate with water and air dry to give 7α-bromo-16α-methyl-1,4-pregnadiene-11β,17α,21-triol-3,20-dione 17-benzoate 21-acetate. Further purify by crystallization from ether:acetone.

EXAMPLE 4

7α-CHLORO- AND 7α-BROMO-11-OXO-1,4-PREGNADIENE-17α,21-DIOL-3,20-DIONES AND ESTERS THEREOF

A. 7α-Chloro Derivatives

In a manner similar to that described in Example 1B treat each of the following 11-oxo-1,4,6-pregnatrienes with dry hydrogen chloride in tetrahydrofuran:

the 21-acetate, 21-n-butyrate, 21-isobutyrate, 21-valerate, 21-caprylate, 21-(1'-adamantyl)-carboxylate, 21-(1'-adamantyl)-acetate, 21-benzoate, and 21-p-methoxybenzoate esters of 16α-methyl-1,4,6-pregnatriene-17α,21-diol-3,11,20-trione 17-propionate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 16α-methyl-1,4,6-pregnatriene-17α,21-diol-3,11,20 -trione 17-n-butyrate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 16α-methyl-1,4,6-pregnatriene-17α,21-diol-3,11,20-trione 17-benzoate;

16α-methyl-1,4,6-pregnatriene-17α,21-diol-3,11,20-trione 17,21-diacetate;

the 21-acetate, 21-propionate and 21-valerate esters of 16α-methyl-1,4,6-pregnatriene-17α,21-diol-3,11,20-trione 17-valerate;

16α-methyl-1,4,6-pregnatriene-17α,21-diol-3,11,20-trione 17-isobutyrate 21-acetate;

and 16α-methyl-1,4,6-pregnatriene-17α,21-diol-3,11,20-trione 17-dodecanoate 21-propionate;

and the 16β-epimers and 16-unsubstituted analogs of the foregoing and the 16-methylene derivatives corresponding to the foregoing.

Isolate and purify each of the resulting products in a manner similar to that described in Example 1B to obtain, respectively, the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-chloro-16α-methyl-1,4-pregnadiene-17α,21-diol-3,11,20 -trione 17-propionate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 7α-chloro-16α-methyl-1,4-pregnadiene-17α,21-diol-3,11,20-trione 17-n-butyrate;

the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters 7α-chloro-16α-methyl-1,4-pregnadiene; 17α,21-diol-3,11,20-trione 17-benzoate;

7α-chloro-16α-methyl-1,4-pregnadiene-17α,21-diol-3,11,20-trione 17,21-diacetate;

the 21-acetate, 21-propionate, and 21-valerate esters of 7α-chloro-16α-methyl-1,4-pregnadiene-17α,21-diol-3,11,20-trione 17-valerate;

7α-chloro-16α-methyl-1,4-pregnadiene-17α,21-diol-3,11,20-trione 17-isobutyrate 21-acetate;

and 7α-chloro-16α-methyl-1,4-pregnadiene-17α,21-diol-3,11,20-trione 17-dodecanoate 21-propionate;

and the 16β-epimers and 16-unsubstituted analogs of the foregoing and the 16-methylene derivatives corresponding to the foregoing.

B. 7α-Bromo Derivatives

In a manner similar to that described in Examples 2B and 3B, treat each of the starting compounds listed in Example 4A with dry hydrogen bromide in glacial acetic acid. Isolate and purify each of the resultant products in a manner similar to that described in Examples 2B and 3B to obtain, respectively, the 7α-bromo derivatives corresponding to the 7α-chloro products of Example 4A.

EXAMPLE 5

7α-CHLORO- AND 7α-BROMO-11β-HYDROXY-1,4-PREGNADIENE-17α,21-DIOL-3,20-DIONES AND ESTERS THEREOF

A. Via Reduction of 11-Keto Analogs

In a manner similar to that described in Examples 1c, 2C and 3C, treat each of the 7α-chloro- and 7α-bromo-11-oxo-1,4-pregnadienes prepared in Example 4 with sodium borohydride in tetrahydrofuran and methanol at 0° C, under an atmosphere of nitrogen, then isolate and purify each of the resultant products in a manner similar to that described to obtain, respectively, the 7α-chloro- and the 7α-bromo- derivatives of each of the 21-acetate, 21-n-butyrate, 21-isobutyrate, 21-valerate, 21-caprylate, 21-(1'-adamantyl)-carboxylate, 21-(1'adamantyl)-acetate, 21-benzoate and 21-p-methoxybenzoate esters of 16α-methyl-1,4-pregnadiene-11β,17α,21-triol-3,20-dione 17-propionate;

the 7α-chloro- and the 7α-bromo- derivatives of each of the 21-acetate, 21n-butyrate, 21-isobutyrate, 21-valerate, 21-caprylate, 21-(1'-adamantyl)carboxylate, 21-(1'-adamantyl)-acetate, 21-benzoate and 21-p-methoxybenzoate esters of 16α-methyl-1,4-pregnadiene-11β,17α,21-triol-3,20-dione 17-n-butyrate;

the 7α-chloro- and the 7α-bromo- derivatives of each of the 21-acetate, 21-n-butyrate, 21-isobutyrate, 21-valerate, 21-caprylate, 21-(1'-adamantyl)-carboxylate, 21-(1'-adamantyl)-acetate, 21-benzoate and 21-p-methoxybenzoate esters of 16α-methyl-1,4-pregnadiene-11β,17α,21-triol-3,20-dione 17-benzoate;

the 7α-chloro- and the 7α-bromo- derivatives of 16α-methyl-1,4-pregnadiene-11β,17α,21-triol-3,20-dione 17,21-diacetate;

the 7α-chloro- and the 7α-bromo derivatives of each of the 21-acetate, 21-propionate, and 21-valerate esters of 16α-methyl-1,4-pregnadiene-11β,17α,21-triol-3,20-dione 17-valerate;

the 7α-chloro- and 7α-bromo- derivatives of 16α-methyl-1,4-pregnadiene-11β,17α,21-triol-3,20-dione 17-isobutyrate 21-acetate;

and the 7α-chloro- and the 7α-bromo- derivatives of 16α-methyl-1,4-pregnadiene-11β,17α,21-triol-3,20-dione 17-dodecanoate 21-propionate;

and the 16β-epimers and 16-unsubstituted analogs of the foregoing and the 16-methylene derivatives corresponding to the foregoing.

B. Alternatively, the compounds of this example are prepared by treating the corresponding 11β-hydroxy-7-unsubstituted 1,4,6-pregnatriene, e.g. the 21-acetate, 21-pivalate and 21-benzoate of 16α-methyl-1,4-pregnadiene-11β,17α,21-triol-3,20-dione with hydrogen chloride or hydrogen bromide in the manner described in Examples 1A, 1B and 1C and isolating and purifying each of the resulting products in the described manner to obtain the corresponding 7α-chloro- and 7α-bromo-1,4-pregnadiene derivative.

EXAMPLE 6

7α,9α,11β-TRIHALOGENO-1,4-PREGNADIENE-17α,21-DIOL-3,20-DIONE 17,21-DIHYDROCARBONCARBOXYLATES

A. 7α-Chloro-16α-Methyl-1,4,9(11)-Pregnatriene-17α,21-Diol-3,20-Dione 17,21-Dipropionate (1) To 7α-chloro-16α-methyl-1,4-pregnadiene-11β,17α,21-triol-3,20-dione 17,21-dipropionate (0.37 gms.) in diemethylformamide (11.1 ml.) and collidine (0.67 ml.) add a 3.5% by weight solution of sulfur dioxide in methanesulfonyl chloride (0.22 ml.). Stir the reaction mixture at 0° C for ½ hour, then at room temperature for ½ hour. Add aqueous 1 N hydrochloric acid, extract the reaction mixture with ethyl acetate, wash the combined organic extracts with water, dry over magnesium sulfate and evaporate in vacuo to a residue comprising 7α-chloro-16α-methyl-1,4,9(11)-pregnatriene-17α,21-diol-3,20-dione 17,21-dipropionate. Purify by triturating the residue with ether and separating the resultant precipitate by filtration. (2) In similar manner, treat each of 7α-bromo-16α-methyl-1,4-pregnadiene-11β,17α,21-triol-3,20-dione 17,21-dipropionate and 7α-bromo-16α-methyl-1,4-pregnadiene-11β,17α,21-triol-3,20-dione 17-benzoate 21-acetate in dimethylformamide and collidine with a 5.5% by weight solution of sulfur dioxide in methanesulfonyl chloride to obtain, respectively, 7α-bromo-16α-methyl-1,4,9(11)-pregnatriene-17α,21-diol-3,20-dione 17,21-dipropionate and 7α-bromo-16α-methyl-1,4,9(11) -pregnatriene-17α,21-diol-3,20-dione 17-benzoate 21-acetate.

B. 7α,11β-Trichloro-16α-Methyl-1,4-Pregnadiene-17α,21-Diol-3,20-Dione 17,21-Dipropionate (1) To a solution of 7α-chloro-16α-methyl-1,4,9(11)-pregnatriene-17α,21-diol-3,20-dione 17,21-dipropionate (0.18 gms.) in chloroform (5 ml.) and pyridine (0.9 ml.), add a solution of dry chlorine gas (28 mg., 1.1 equivalents) in a chloroform (4 ml.) and let the mixture stand at room temperature for 3 hours. Add methylene chloride (300 ml.) and wash the reaction mixture sequentially with 10% aqueous sodium thiosulfate solution, 1 N hydrochloric acid, and water. Dry over magnesium sulfate and evaporate. Purify the resultant residue on silica gel via thick layer chromatography utilizing as developing solvent chloroform:ethyl acetate (9:1). Remove the least polar band as shown by ultraviolet light and elute with ethyl acetate. Evaporate the combined ethyl acetate eluate to a residue comprising 7α,9α,11β-trichloro-16α-methyl-1,4-pregnadiene-17α,21-diol-3,20-dione 17,21-dipropionate. Further purify by trituration with acetone, and filtering the triturated precipitate; m.p. 225°–228° C; $\lambda MeOH_{max}$ 236 nm ($\epsilon$15,600). (2) In similar manner, treat the 7α-bromo-1,4,9(11)-pregnatrienes prepared in Example 6A(2) with chlorine to obtain, respectively, 7α-bromo-9α,11β-dichloro-16α-methyl-1,4-pregnadiene-17α,21-diol-3,20-dione 17,21-dipropionate and 7α-bromo-9α,11β-dichloro-16α-methyl-1,4-pregnadiene-17α,21-diol-3,20-diene 17-benzoate 21-acetate.

C. 7α,9α-Dichloro-11β-Fluoro-16α-Methyl-1,4-Pregnadiene-17α,21-Diol-3,20-Dione 17,21-Dipropionate (1) To a solution of 7α-chloro-16α-methyl-1,4,9(11)-pregnatriene-17α,21-diol-3,20-dione 17,21-dipropionate (0.5 gms.) in chloroform (10 ml.) and pyridine (1 ml.), add a solution of hydrogen fluoride (5 gms.) in tetrahydrofuran (5 ml.) followed by N-chlorosuccinimide (128 mg.). Dilute the reaction mixture with sufficient methylene chloride to form a solution, and stir the reaction mixture for 48 hours at room temperature. Pour the reaction mixture into aqueous sodium carbonate, extract the aqueous mixture with methylene chloride, wash the combined organic extracts successively with water, dilute hydrochloric acid and finally with water. Dry over magnesium sulfate, filter and evaporate to a residue comprising 7α,9α-dichloro-11β-fluoro-16α-methyl-1,4-pregnadiene-17α,21-diol-3,20-dione 17,21-dipropionate. Purify by triturating the residue with ether, filter and crystallize from acetone:thexane. (2) In similar manner, treat the 7α-bromo-1,4,9(11)-pregnatrienes prepared in Example 6A(2) in chloroform with hydrogen fluoride and N-chlorosuccinimide in the presence of pyridine and isolate the resultant products to obtain, respectively, 7α-bromo-9α-chloro-11β-fluoro-16α-methyl-1,4-pregnadiene-17α,21-diol-3,20-dione 17,21-dipropionate and 7α-bromo-9α-chloro-11β-fluoro-16α-methyl-1,4-pregnadiene-17α,21-diol-3,20-dione 17-benzoate 21-acetate.

D. 7α-Chloro-9α-Bromo-11β-Fluoro-16α-Methyl-1,4-Pregnadiene-17α,21-Diol-3,20-Dione 17,21-Dipropionate (1) To a solution of 7α-chloro-16α-methyl-1,4,9(11)-pregnatriene-17α,21-diol-3,20-dione 17,21-dipropionate (0.5 gms.) in chloroform (10 ml.) and pyridine (1 ml.) add a solution of hydrogen fluoride (5 gms.) in tetrahydrofuran (5 ml.) followed by N-bromoacetamide (130 mg.). Dilute the reaction mixture with sufficient methylene chloride to form a solution and stir for 48 hours at room temperature. Pour the reaction mixture into aqueous sodium carbonate, extract the aqueous mixture with methylene chloride, wash the combined organic extracts successively with water, dilute hydrochloric acid and finally with water. Dry the solution over magnesium sulfate, filter and evaporate. Dissolve the resultant residue in acetone:ether and filter through a column of Florisil and elute with ether. Combine the eluates and evaporate in vacuo to a residue comprising 7α-chloro-9α-bromo-11β-fluoro-16α-methyl-1,4-pregnadiene-17α,21-diol-3,20-dione 17,21-dipropionate. (2) In the foregoing procedure by utilizing as starting compounds the 7α-bromo-1,4,9(11)-pregnatrienes prepared in Example 6A(2), there is obtained, respectively, 7α,9α-dibromo-11β-fluoro-16α-methyl-1,4-pregnadiene-17α,21-diol-3,20-dione 17,21-dipropionate and 7α,9α-dibromo-11β-fluoro-16α-methyl-1,4-pregnadiene-17α,21-diol-3,20-dione 17-benzoate 21-acetate.

E. 7α,11β-Dichloro-9α-Bromo-16α-Methyl-1,4-Pregnadiene-17α,21-Diol-3,20-Dione 17,21-Dipropionate (1) To a stirred solution of 7α-chloro-16αα-methyl-1,4,9(11)-pregnatriene-17α,21-diol-3,20-dione 17,21-dipropionate (0.5 gms.) in chloroform (10 ml.) and pyridine (1 ml.), cool to −20° C, add N-bromoacetamide (130 mg.) and a solution of hydrogen chloride (100 mg.) in tetrahydrofuran (5 ml.). Continue stirring at −20° C for 15 minutes, then allow the reaction mixture to attain room temperature for an additional 15 minutes. Add methylene chloride to the reaction mixture and wash the reaction mixture with thiosulfate solution, water, 10% aqueous sodium bicarbonate and finally with water. Dry over magnesium sulfate, filter and evaporate in vacuo. Crystallize the resultant residue from acetone:hexane to give 7α,11β-dichloro-9α-bromo-16α-methyl-1,4-pregnadiene-17α,21-diol-3,20-dione 17,21-dipropionate. (2) In the foregoing procedure, by utilizing as starting compound the 7α-bromo-1,4,9(11)-pregnatrienes prepared in Example 6A(2), there is obtained, respectively, 7α,9α-dibromo-11β-chloro-16α-methyl-1,4-pregnadiene-17α,21-diol-3,20-dione 17,21-dipropionate and 7α,9α-dibromo-11β-chloro-16α-methyl-1,4-pregnadiene-17α,21-diol-3,20-dione 17-benzoate 21-acetate.

F. Treat each of the 7α-chloro- and 7α-bromo-11β-hydroxy-1,4-pregnadiene-17α,21-diol-3,20-diones prepared in Example 5 in a manner similar to that described in Example 6A followed by reaction of the corresponding 7α-chloro- and 7α-bromo-1,4,9(11)-pregnatriene-17α,21-diol-3,20-diones thereby formed, with chlorine in the manner described in Example 6B or with a mixture of halogenating reagents in a manner similar to that described in Example 6C–6E to obtain the corresponding 7α-chloro- and 7α-bromo-9,α,11β-dihalogeno-1,4-pregnadiene-17α,21-diol-3,20-diones thereby formed.

EXAMPLE 7

7α-CHLORO-9α-HALOGENO-1,4-PREGNADIENE-17α,21-DIOL-3,20-DIONES

A. 7α-Chloro-9α-Fluoro-16α-Methyl-1,4-Pregnadiene-11β,17α,21-Triol-3,20-Dione 21-Acetate To 9α-fluoro-16α-methyl-1,4-pregnadiene-7β,11β,17α,21-tetrol-3,20-dione 21-acetate (0.5 gms.) in methylene chloride (100 ml.) at 0° C under an atmosphere of nitrogen add N,N-diethyl-1,2,2-trichlorovinylamine (1.67 ml.). Stir at 0° C for 7 hours, evaporate in vacuo, place the resultant residue on a silica gel column (50 gms.) and elute with chloroform:ethyl acetate (3:1). Combine the like fractions containing the desired compound as determined by thin layer chromatography and evaporate. Further purify the resultant residue on this layer silica gel plates developing with chloroform-ethyl acetate (3:1). Remove the band containing the desired product as visualized under ultraviolet light and elute with ethyl acetate. Evaporate the eluate to a residue comprising: 7α-chloro-9α-fluoro-16α-methyl-1,4-pregnadiene-11β,17α,21-triol-3,20-dione 21-acetate. Further purify by crystallization from acetone:hexane.

B. In the procedure of Example 7A, by starting with each of the 9α-chloro- and 9α-bromo- analogs of the 9α-fluoro-7β-hydroxy-1,4-pregnadiene starting compound, there is obtained the corresponding 7α-chloro derivative, i.e. 7α,9α-dichloro-16α-methyl-1,4-pregnadiene-11β,17α,21-triol-3,20-dione 21-acetate and 7α-chloro-9α-bromo-16αmethyl-1,4-pregnadiene-11β,17α,21-triol-3,20-dione 21-acetate, respectively.

C. Similarly, utilizing the procedure of Example 7A, by starting with the corresponding 7β-hydroxy derivative prepared as described in Preparation 11, there is obtained 7α-chloro-9α-fluoro-16α-methyl-1,4-pregnadiene-11β,17α,21-triol-3,20-dione 17,21-dipropionate, 7α-chloro-9α-fluoro-16α-methyl-1,4-pregnadiene-11β,17α,21-triol-3,20-dione 17-benzoate 21-propionate, 7α-chloro-9α-fluoro-16α-methyl-1,4-pregnadiene-11β,17α,21-triol-3,20-dione 17-n-butyrate 21-propionate, the 9α-bromo- and 9α-chloro- analogs of the foregoing, and the 16β-methyl epimers and 16-unsubstituted analogs and 16-methylene derivatives corresponding to the foregoing.

EXAMPLE 8

7α-FLUORO-1,4-PREGNADIENE-3,20-DIONES

A. 7α-Fluoro-16α-Methyl-1,4-Pregnadiene-11β,17α,21-Triol-3,20-Dione 21-Acetate

To 16α-methyl-1,4-pregnadiene-7β,11β,17α,21-tetrol-3,20-dione 21-acetate (0.13 gms.) in methylene chloride (15 ml.) at 0° C under an atmosphere of nitrogen, add N-(2-chloro-1,1,2-trifluoroethyl)-diethylamine (fluoramine) (0.286 ml.). Stir at 0° C for 18 hours, then evaporate in vacuo and purify the resultant residue via thin layer chromatography developing with chloroform: ethyl acetate (5:2) to obtain a mixture comprising 7α-fluoro-16α-methyl-1,4-pregnadiene-11β,17α,21-triol-3,20-dione 21-acetate and 16α-methyl-1,4,6-pregnatriene-11β,17α,21-triol-3,20-dione 21-acetate. Treat the foregoing mixture (55 mg.) in dioxane (0.58 ml.) and pyridine (3 drops) with osmium tetroxide (10 mg.) at room temperature for 5 days. Saturate the reaction mixture with hydrogen sulfide, filter the reaction mixture, evaporate the filtrate an vacuo at room temperature and purify the resultant residue via thin layer chromatography on silica gel developing with chloroform:ethyl acetate (2:1). Evaporate the combined eluates containing the desired product and triturate the resultant residue with ether:hexane to obtain 7α-fluoro-16α-methyl-1,4-pregnadiene-11β,17α,21-triol-3,20-dione 21-acetate.

B. 7α,9α-Difluoro-16α-Methyl-1,4-Pregnadiene-11β,17α,21-Triol-3,20-Dione 21-Acetate To 9α-fluoro-16α-methyl-1,4-pregnadiene-7β,11β,17α21-tetrol-3,20-dione 21-acetate (0.35 gms.) in methylene chloride (350 ml.) at 0° C and under an atmosphere of nitrogen, add fluoramine (0.76 ml.). Stir at 0° C for 24 hours, and evaporate the reaction mixture in vacuo. Chromatograph the resultant residue on silica gel via thin layer chromtography developing with chloroform: ethyl acetate (2:1) and eluting with ethyl acetate the band containing the desired product as visualized under ultraviolet light. Evaporate the combined eluates to a residue of 7α,9α-difluoro-16α-methyl-1,4-pregnadiene-11β,17α,21-triol-3,20-dione 21-acetate. Further purify by crystallization from acetone:methanol:hexane; m.p. 234°-237° C; $[\alpha]^{26}$ + 45.4°; (dimethylformamide).

C. Similarly, by treating any of the 7β-hydroxy-1,4-pregnadienes prepared as described in Preparation 11 with fluoramine according to the procedures of Examples 8A and 8B, there is obtained the corresponding 7α-fluoro-1,4-pregnadiene.

EXAMPLE 9

7α-IODO-9α-UNSUBSTITUTED-1,4-PREGNADIENE-3,20-DIONES

A. 7α-Iodo-16α-Methyl-1,4-Pregnadiene-11β,17α,21-Triol-3,20-Dione 21-Acetate

Add 16α-methyl-1,4,6-pregnatriene-11β, 17α,21-triol-3,20-dione 21-acetate (0.1 gms.) to a solution of dry hydrogen iodide (0.512 gms.) in glacial acetic acetic acid (2 ml.) and stir the reaction mixture at room temperature for 50 minutes. Pour into ice water, separate the resultant precipitate by filtration and dry the precipitate. Triturate the precipitate with ether, separate the solid by filtration, dissolve the solid in methylene chloride, wash the methylene chloride solution with aqueous 0.1 N sodium thiosulfate solution, then with water, dry over magnesium sulfate and evaporate in vacuo. Triturate the resultant residue with hexane and filter to obtain 7α-iodo-16α-methyl-1,4-pregnadiene-11β,17α,21-triol-3,20-dione 21-acetate. B. In similar manner, treat each of the 9-unsubstituted-1,4,6-pregnatriene-3,20-dione intermediates prepared as described in Preparations 1-10 with hydrogen iodide in acetic acid according to the procedure of Example 9A to obtain the corresponding 7α-iodo-9-unsubstituted-1,4-pregnadiene-3,20-dione derivative.

EXAMPLE 10

7α-BROMO-9α-HALOGENO-1,4-PREGNADIENE-3,20-DIONES

A.
7α-Bromo-9α-Fluoro-16α-Methyl-1,4-Pregnadiene-11β,17α,21-Triol-3,20-Dione 21-Acetate To a solution of 7β-hydroxy-9α-fluoro-16α-methyl-1,4-pregnadiene-11β,17α,21-triol-3,20-dione 21-acetate (0.1 gms.) and lithium bromide (0.1gms.). in methylene chloride (100 ml.) cooled to 0° C, add fluoramine (0.23 ml.). Stir at 0° C for 24 hours, then evaporate in vacuo. Dissolve the resultant residue in chloroform, wash the chloroform solution with water, dry over magnesium sulfate and evaporate. Purify via thin layer chromatography utilizing as developing solvent chloroform-ethyl acetate (2:1). Remove the band containing the desired product as visualized under ultraviolet light and elute with ethyl acetate. Evaporate the combined ethyl actate eluates in vacuo to a residue comprising 7α-bromo-9α-fluoro-16α-methyl-1,4-pregnadiene-11β,17α,21-triol-3,20-dione 21-acetate. B. In the procedure of Example 10A, by starting with each of the 9α-chloro and 9α-fluoro-7β-hydroxy-1,4-pregnadiene starting compound, there is obtained the corresponding 7α-bromo derivative, i.e. 7α-bromo-9α-chloro-16α-methyl-1,4-pregnadiene-11β,17α,21-triol-3,20-dione 21-acetate and 7α,9α-dibromo-16α-methyl-1,4-pregnadiene-11β,17α,21-triol-3,20-dione 21-acetate, respectively. C. Similarly, by treating any of the 7β-hydroxy-1,4-pregnadienes prepared in Preparation 11 with fluoramine and lithium bromide according to the procedure of Example 10A, there is obtained the corresponding 7α-bromo-1,4-pregnadiene derivative. D. In the procedure of Example 10A, by substituting for lithium bromide an equivalent quantity of lithium chloride and by utilizing tetrahydrofuran as solvent instead of methylene chloride, there is obtained the corresponding 7α-chloro compound, i.e. 7α-chloro-9α-fluoro-16α-methyl-1,4-pregnadiene-11β,17α,21-triol-3,20-dione 21-acetate.

EXAMPLE 11

7α-HALOGENO-21-DESOXY-1,4-PREGNADIENE-3,20-DIONES

A. 7α-Chloro-21-Desoxy-1,4- Pregnadiene-3,20-Dione
(1) 7α-Chloro-1,4-Pregnadiene-17α-01-3.20-Dione To 17α-hydroxy-1,4,6-pregnatriene-3,20-dione (0.5 gms.) add glacial acetic acid (20 ml.) saturated with dry hydrogen chloride gas and lithium chloride (2 gms.). Stir at room temperature for 45 minutes, then pour into an aqueous sodium carbonate solution and extract the aqueous mixture with ether. Wash the combined organic extracts with water, dry over magnesium sulfate and evaporate to a residue comprising 7α-chloro-1,4-pregnadiene-17α-ol-3,20-dione. Purify by crystallization from methanol; m.p. 229°-231°; $[\alpha]^{26}$ + 50.7° (dioxane). (2) In the above procedure, by utilizing as starting compounds each of the 17-propionate, 17-n-butyrate, 17-valerate and 17-benzoate of 1,4-pregnadiene-11β,17α-diol-3,20-dione, there is obtained the corresponding 7α-chloro derivative, i.e. the 17-propionate, 17-n-butyrate, 17-valerate and 17-benzoate of 7α-chloro-1,4-pregnadiene-11β,17α-diol-3,20-dione, respectively.

B. 7α-Bromo-21-Desoxy-1,4-Pregnadiene-3,20-Diones (1) In the procedure of Example 11A(1), by utilizing as reagents an equivalent quantity of dry hydrogen bromide instead of dry hydrogen chloride and an equivalent quantity of lithium bromide instead of lithium chloride, there is obtained the corresponding 7α-bromo derivative, i.e. 7α-bromo-1,4-pregnadiene-17α-ol-3,20-dione.

(2) Treat each of the starting compounds of Example 11A (2) with dry hydrogen bromide and lithium bromide in glacial acetic acid in the manner of Example 11B(1) to obtain, respectively, the 17-propionate, 17n-butyrate, 17-valerate and 17-benzoate of 7-α-bromo-1,4-pregnadiene-11β,17α-diol-3,20-dione.

C. 7α-Fluoro-21-Desoxy-1,4-Pregnadiene-3,20-Diones (1) In a manner similar to that described in Example 8A, treat each of 1,4-pregnadiene-7β,17α-diol-3,20-dione and the 17-propionate, 17-n-butyrate, 17-valerate and 17-benzoate of 1,4-pregnadiene-7β,11β,17α-triol-3,20-dione with fluoramine in methylene chloride under an atmosphere of nitrogen. Isolate and purify each of the resultant products in a manner similar to that described to obtain, respectively, 7α-fluoro-1,4-pregnadiene-17α-ol-3,20-dione and the 17-propionate, 17-n-butyrate, 17-valerate and 17-benzoate of 7α-fluoro-1,4-pregnadiene-11β,17α-diol-3,20-dione.

D. 7α-Iodo 21-Desoxy-1,4-Pregnadiene-3,20-Diones

In a manner similar to that described in Example 9A, treat each of the pregnatriene starting compounds of Example 11A(1) and 11A(2) with hydrogen iodide in glacial acetic acid and isolate each of the resultant products in the described manner to obtain, respectively, 7α-iodo-1,4-pregnadiene-17α-ol-3,20-dione, and the 17-propionate, 17-n-butyrate, 17-valerate and 17-benzoate of 7α-iodo-1,4-pregnadiene-11β,17α-diol-3,20-dione.

EXAMPLE 12

7α,21-DIHALOGENO-1,4-PREGNADIENE-3,20-DIONES

A. 7α-Chloro-21-Halogeno Derivatives (1) 7α,21-Dichloro-16α-Methyl-1,4-Pregnadiene-11β,17α-Diol-3,20-Dione 17-Propionate In a manner similar to that described in Example 1A, treat 16α-methyl-21-chloro-1,4,6-pregnatriene-11β,17α-diol-3,20-dione 17-propionate with dry hydrogen chloride gas in dioxane and isolate the resultant product in a manner similar to that to obtain 7α,21-dichloro-16α-methyl-1,4-pregnadiene-11β,17α-diol-3,20-dione 17-propionate.

(2) In similar manner, in the procedure of Example 12A(1), by utilizing as staring compound each of the 21-fluoro and 21-bromo analogs of the 21-chloro starting compound named therein, there is obtained the corresponding 21-fluoro and 21-bromo derivative, i.e. 7α-chloro-21-fluoro-1,4-pregnadiene-11β,17α-diol-3,20-dione 17-propionate, and 7α-chloro-21-bromo-1,4-pregnadiene-11β,17α-diol-3,20-dione 17-propionate, respectively.

(3) In the procedure of Example 12A, by utilizing starting compounds having different ester at C-17, e.g. the 17-n-butyrate -n-butyrate and 17-benzoate -diol-and the 17-benzoate corresponding to the 17-propionate ester named therein, there is obtained the corresponding 7α-chloro-21-halogeno derivative, i.e. the 17-n-benzoate of 7α,21-dichloro-16α-methyl-1,4-pregnadiene-11β,17α-dol-3,20-dione, 7α-chloro-21-fluoro-1,4-pregnadiene-11β,17α-diol-3,20-dione and of 7α-chloro-21-bromo-1,4-pregnadiene-11β,17α-diol-3,20-dione.

(4) In the procedures of Examples 12A(1)-(3), by utilizing as starting compounds the 16β-methyl epimer or the 16-unsubstituted or 16-methylene derivatives of 16α-methyl starting compounds named therein, there is obtained the corresponding 16β-methyl, 16-unsubstituted or 16-methylene derivatives of the 7α,21-dihalogeno products named therein.

B. 7α-Bromo- and 7α-Iodo-21-Halogeno Derivatives

Treat each of the 1,4,6-pregnatriene starting compounds of Example 12A(1)-(4) with dry hydrogen bromide in acetic acid in a manner similar to that described in Example 2A and B or with dry hydrogen iodide in acetic acid according to the procedure of Example 9A to obtain each of the 7α-bromo- and 7α-iodo analogs corresponding to the 7α-chloro derivatives of Example 12A.

C. 7α-Fluoro-21Halogeno Derivatives (1) 7α-Fluoro-21-Chloro-16α-Methyl-1,4-Pregnadiene-11β,17α-Diol-3,20-Dione 17-Propionate In a manner similar to that described in Example 8A, treat 16α-methyl-21-chloro-1,4-pregnadiene-7β,11β,17α-triol-3,20-dione 17-propionate with fluoramine in methylene chloride under an atmosphere of nitrogen and isolate and purify the resultant product in the described manner to obtain 7α-fluoro-21-chloro-16α-methyl-1,4-pregnadiene-11β,17α-diol-3,20-dione 17-propionate. (2) In the procedure of Example 12C(1), by utilizing as starting compounds each of the 21-fluoro- and 21-bromo- analogs of the 21-chloro starting compounds named therein, there is obtained the corresponding 21-fluoro- and 21-bromo derivative, i.e. 7α-fluoro-21-bromo-16α-methyl-1,4-pregnadiene-11β,17α-diol-3,20-dione 17-propionate and 7α,21-difluoro-16α-methyl-1,4-pregnadiene-11β,17α-diol-3,20-dione 17-propionate, respectively. (3) In Example 12C(1) and 12C(2), by utilizing the 9α-fluoro- and 9α-chloro- analogos of the starting compounds named therein, there is obtained the corresponding 9α-fluoro- and 9α-chloro- analogs of the 7α-fluoro-1,4-pregnadiene products obtained therein.

EXAMPLE 13

OTHER 7α-HALOGENO-9-UNSUBSTITUTED-1,4-PREGNADIENE-3,20-DIONES

A. 9α-Unsubstituted,1,4,6-Pregnatriene-3,20-Diones (1) In a manner similar to that described in Preparation 1A treat each of the following 1,4-pregnadiene-3,20-diones with dry hydrogen chloride gas in dioxane and DDQ.

(1) 16α,17α-isopropylidenedioxy-1,4-pregnadiene-11β,21-diol-3,20-dione 21-acetate.

(2) 14α,17α-butylidenedioxy-1,4-pregnadiene-11β,21-diol-3,20-dione 21-acetate, (3) 2′,2′-dimethyl-1,4-pregnadieno[17,16α-d]-1′,3′-oxathiolane-3,11,20-trione, (4) 11β-hydroxy-2',2'-dimethyl-1,4-pregnadieno[17,16α-d]-1',3'-oxathiolane-3,20-dione,
(5) D-homo-1,4-pregnadiene-17α,21-diol-3,11,20-trione 17,21-dipropionate,
(6) D-homo-1,4-pregnadiene-11β,17α,21-triol-3,20-dione 17,21-di-n-butyrate,
(7) n-butyl 11β-hydroxy-3,20-dioxo-16α-methyl-1,4-pregnadien-21-oate,
(8) propyl 2-chloro-11β-hydroxy-3,20-dioxo-16α-methyl-1,4-pregnadiene-21-oate,
(9) 16β-methyl-20-chloromethoxy-21-nor-1,4-pregnadiene-11β,17α-diol-3,20-dione 17-propionate,
(10) 16β-methyl-20-fluoromethoxy-21-nor-1,4-pregnadiene-11β,17α-diol-3,20-dione 17-propionate,
(11) 16-methylene-20-chloromethoxy-21-nor-1,4-pregnadiene-11β,17α-diol-3,20-dione 17-propionate,
(12) 16-methylene-20-fluoromethoxy-21-nor-1,4-pregnadiene-11β,17α-diol-3,20-dione 17-propionate,
(13) 16-fluoromethylene-1,4-pregnadiene-11β,17α,21-triol-3,20-dione 17,21-dipropionate,
(14) 16-chloromethylene-1,4-pregnadiene-17α,21-diol-3,11,20-trione 17-benzoate 21-propionate,
(15) 16-butylidene-1,4-pregnadien-17α-ol-3,20-dione 17-propionate,
(16) 16-ethylidene-1,4-pregnadiene-17α,21-diol-3,11,20-trione 17,21-dipropionate,
(17) 16α,17α-cyclopentylidenedioxy-1,4-pregnadiene-11β,21-diol-3,20-dione 21-acetate,
(18) 16β-methyl-21-nor-1,4-pregnadiene-11β,17α-diol-3,20-dione 20-methoxy 17-propionate,
(19) 16α-methyl-1,4-pregnadiene-11β,21-diol-3,20-dione 21-pivalate.

Isolate and purify each of the resultant products in a manner similar to that described in Preparation 1A to obtain the 6-dehydro analog of each of the starting compounds, respectively. (2) Treat each of the following compounds with dry hydrogen chloride in the manner described in Preparation 1A in dioxane followed by DDQ.

(1) 14α,17α-(2'-butenylidenedioxy)-1,4-pregnadiene-11β,21-diol-3,20-dione 21-isonicotinate,
(2) 11β,21-dihydroxy-2'-methyl-5'βH-1,4-pregnadiene[17,16α-d]-oxazole-3,20-dione 21-acetate.

After stirring the reaction mixture at room temperature for 24 hours, filter and evaporate the filtrate at 40° C in vacuo. Dissolve the resultant residue in water, neutralize with sodium hydroxide and extract with chloroform. Wash the organic solution with water, dry over magnesium sulfate and filter through a column of neutral alumina, washing the column with chloroform:ethyl acetate. Evaporate each of the eluates to a residue comprising the 6-dehydro analog of each of the starting compounds.

B. 7α-Chloro-9-Unsubstituted-1,4-Pregnadienes (1) In a manner similar to that described in Example 1A, treat each of the 1,4,6-pregnatriene-3,20-diones prepared in Example 13A(1) with dry hydrogen chloride in dioxane, and isolate and purify each of the resultant products in a manner similar to that described to obtain the 7α-chloro derivative of each of the starting compounds of Example 13A(1). (2) Treat each of 14α,1-7α-(2'-butenylidenedioxy)-1,4,6-pregnatriene-11β,21-diol-3,20-dione 21-isonicotinate and 11β,21-dihydroxy-2'-methyl-5'βH-1,4,6-pregnadieno[17,16α-d]oxazole-3,20-dione 21-acetate with hydrogen chloride gas in dioxane for 16 hours at room temperature in a manner similar to that described in Example 1A. Pour each of the reaction mixtures into ice water, neutralize the aqueous solution with sodium hydroxide, then separate the resultant precipitate by filtration, wash with water and dry in air. Separate the components in each of the foregoing precipitates in a manner similar to that described in Example 1 to obtain, respectively, 7α-chloro-14α,1-7α-(2'-butenylidenedioxy)-1,4-pregnadiene-11β,21-diol-3,20-dione 21-isonicotinate and 7α-chloro-11β,21-dihydroxy-2'-methyl-5'βH-1,4-pregnadieno-[17,16α-d]oxazole-3,20-dione 21-acetate.

C. 7α-Bromo-9-Unsubstituted-1,4-Pregnadienes (1) In a manner similar to that described in Example 2, treat each of the 1,4,6-pregnatriene-3,20-diones prepared in Example 13A(1) with dry hydrogen bromide in acetic acid. Isolate and purify each of the resultant products to obtain the corresponding 7α-bromo derivative of each of the starting compounds of Example 13A(1), respectively.

(2) Treat each of the 1,4,6-pregnatriene-3,20-dione derivatives prepared in Example 13A(2) with dry hydrogen bromide in acetic acid in a manner similar to that described in Example 2A. After stirring the reaction mixture at 0° C for 1 hour, pour into water, neutralize with sodium hydroxide, separate the resultant precipitate by filtration, wash each of the precipitates with water and dry. Purify each of the foregoing precipitates in a manner similar to that described in Example 2A to obtain, respectively, the 7α-bromo derivatives of each of the starting compounds of Example 13A(2).

D. 7α-Iodo-9-Unsubstituted-1,4-Pregnadienes (1) In a manner similar to that described in Example 9A, treat each of the 1,4,6-pregnatriene-3,20-dione derivatives prepared in Example 13A(1) with dry hydrogen iodide in glacial acetic acid. Isolate and purify each of the resultant products in a manner similar to that described to obtain the 7α-iodo derivative of each of the 1,4-pregnadiene-3,20-dione starting compounds of Example 13A(1), respectively.

(2) Treat each of the 1,4,6-pregnatriene-3,20-dione compounds of Example 13A(2) with dry hydrogen iodide in acetic acid in the manner described in Example 9A. After stirring the reaction mixture at room temperature for 15 minutes, pour into ice water, neutralize with sodium hydroxide, separate the resultant precipitate by filtration, and purify each of the precipitates in a manner similar to that described in Example 9A to obtain the 7α-iodo derivative of each of the 1,4-pregnadiene-3,20-dione starting compounds of Example 13A(2).

E. 7α-Fluoro-9-Unsubstituted-1,4-Pregnadienes (1) 7β-Hydroxy-1,4-Pregnadiene-3,20-Diones Subject the following 1,4,6-pregnatriene-3,20-diones to a sequence of reactions similar to those described in Preparation 11A(1)-(4).

(1) 16α,17α-isopropylidenedioxy-1,4,6-pregnatriene-11β,21-diol-3,20-dione 21-acetate,
(2) 14α,17α-n-butylidenedioxy-1,4,6-pregnatriene-11β,21-diol-3,20-dione 21-acetate,
(3) D-homo-1,4,6-pregnatriene-17α,21-diol-3,11,20-trione 17,21-dipropionate,
(4) D-homo-1,4,6-pregnatriene-11β,17α,21-triol-3,20-dione 17,21-di-n-butyrate,
(5) 16β-methyl-20-chloromethoxy-21-nor-1,4,6-pregnatriene-11β,17α-diol-3,20-dione 17-propionate,
(6) 16β-methyl-20-fluoromethoxy-21-nor-1,4,6-pregnatriene-11β,17α-diol-3,20-dione 17-propionate,
(7) 16α,17α-cyclopentylidenedioxy-1,4,6-pregnatriene-11β,21-diol-3,20-dione 21-acetate.

Isolate and purify each of the respective products in a manner similar to that described in Preparation 11A(4) to obtain, respectively,
(1) 16α,17α-isopropylidenedioxy-1,4-pregnadiene-7β,11β,21-triol-3,20-dione 21-acetate,
(2) 14α,17α-n-butylidenedioxy-1,4-pregnadiene-7β,11β,21-triol-3,20-dione 21-acetate,
(3) D-homo-1,4-pregnadiene-7β,17α,21-triol-3,11,20-trione 17,21-dipropionate,
(4) D-homo-1,4-pregnadiene-7β,11β,17α,21-tetrol-3,20-dione 17,21-di-n-butyrate,
(5) 16β-methyl-20-chloromethoxy-21-nor-1,4-pregnadiene-11β,17α-diol-3,20-dione 17-propionate,
(6) 16β-methyl-20-fluoromethoxy-21-nor-1,4-pregnadiene-7β,11β,17α-triol-3,20-dione 17-propionate,
(7) 16α,17α-cyclopentylidenedioxy-1,4-pregnadiene-7β,11β,21-triol-3,20-dione 21-acetate.

(2) In a manner similar to that described in Example 8A, treat each of the 7β-hydroxy derivatives of Example 13E(1) with fluoramine in methylene chloride at 0° C under an atmosphere of nitrogen. Isolate and purify each of the resultant products in a manner similar to that described to obtain, respectively,
(1) 7α-fluoro-16α,17α-isopropylidenedioxy-1,4-pregnadiene-11β,21-diol-3,20-dione 21-acetate,
(2) 7α-fluoro-14α,17α-n-butylidenedioxy-1,4-pregnadiene-11β,21-diol-3,20-dione 21-acetate,
(3) 7α-fluoro-D-homo-1,4-pregnadiene-17α,21-diol-3,11,20-trione 17,21-dipropionate,
(4) 7α-fluoro-D-homo-1,4-pregnadiene-11β,17α,21-triol-3,20-dione 17,21-di-n-butyrate,
(5) 7α-fluoro-16β-methyl-20-chloromethoxy-21-nor-1,4-pregnadiene-11β,17α-diol-3,20-dione 17-propionate,
(6) 7α-fluoro-16β-methyl-20-fluoromethoxy-21-nor-1,4-pregnadiene-11β,17α-diol-3,20-dione 17-propionate,
(7) 7α-fluoro-16α,17α-cyclopentylidenedioxy-1,4-pregnadiene-11β,21-diol-3,20-dione 21-acetate.

EXAMPLE 14

OTHER 7α,9α-DIHALOGENO-11β-HYDROXY-1,4-PREGNADIENE-3,20-DIONES

A. 7β-Hydroxy-9α-Halogeno-1,4-Pregnadiene-3,20-Diones (1) Treat each of the following 6,7-unsubstituted-9α-halogeno-1,4-pregnadiene-3,20-diones with dry hydrogen chloride gas and DDO in dioxane in a manner similar to that described in Preparation 1A, thence subject each of the thereby formed 9α-halogeno-1,4,6-pregnatriene-3,20-diones to a sequence of reactions similar to those described in Preparation 11A(1)-(4).
(1) 9α-fluoro-11β,21-dihydroxy-2′-methyl-5′βH-1,4-pregnadieno-[17,16α-d]oxazole-3,20-dione 21-acetate,
(2) 9α-fluoro-16α,17α-cyclopentylidenedioxy-1,4-pregnadiene-11β,21-diol-3,20-dione 21-acetate,
(3) 9α-fluoro-11β-hydroxy-2′,2′-dimethyl-1,4-pregnadieno[17,16α-d]-1′,3′-oxathiolane-3,20-dione,
(4) 9α-chloro-11β-hydroxy-21,21-dimethyl-1,4-pregnadieno-[17,16α-d]-1′,3′-oxathiolane-3,20-dione,
(5) 9α-fluoro-16α-methyl-2′,2′-diacetoxy-1,4-pregnadiene-11β,17α-diol-3,20-dione 17-propionate,
(6) 9α-fluoro-16α-methyl-1,4-pregnadien-11β-ol-3,20,21-trione 21,21-dimethylacetal,
(7) 9α-fluoro-16α-methyl-1,4-pregnadien-11β-ol-3,20,21-trione 21-ethyleneketal,
(8) 2-chloro-9α-fluoro-16α-methyl-1,4-pregnadiene-11β,17α-diol-3,20,21-trione,
(9) 2-chloro-9α-fluoro-16α-methyl-1,4-pregnadiene-11β,17α-diol-3,20,21-trione 21-methylhemiacetal,
(10) 9α-fluoro-16β-methyl-20-fluoromethoxy-21-nor-1,4-pregnadiene-11β,17α-diol-3,20-dione 17-propionate,
(11) 9α-fluoro-16β-methyl-20-chloromethoxy-21-nor-1,4-pregnadiene-11β,17α-diol-3,20-dione 17-propionate,
(12) 9α-fluoro-16α-methyl-1,4-pregnadiene-11β,21-diol-3,20-dione 21-acetate.

Isolate and purify each of the resultant products in a manner similar to that described in Preparation 11A(4) to obtain the corresponding 7β-hydroxy derivatives of the foregoing starting compounds.

(2) In a manner similar to that described in Example 1A treat each of the following 6,7-unsubstituted-9α-fluoro-1,4-pregnadiene-3,20-diones with dry hydrogen hloride and DDQ in dioxane followed by treatment of the resulting corresponding 9α-fluoro-1,4,6-pregnatriene-3,20-dione in a manner similar to that described in Preparation 11D.
(1) 9α-fluoro-16-methylene-20-fluoromethoxy-21-nor-1,4-pregnadiene-11β,17α-diol-3,20-dione 17-propionate,
(2) 9α-fluoro-16-methylene-20-chloromethoxy-21-nor-1,4-pregnadiene-11β,17α-diol-3,20-dione 17-propionate,
(3) 9α-fluoro-16-fluoromethylene-1,4-pregnadiene-11β,17α,21-triol-3,20-dione 21-acetate.

Isolate and purify each of the resultant products in a manner similar to that described in Preparation 11D(3) to obtain the corresponding 7β-hydroxy derivative, i.e.
(1) 9α-fluoro-16-methylene-20-fluoromethoxy-21-nor-1,4-pregnadiene-7β,11β,17α-triol-3,20-dione 17-propionate,
(2) 9α-fluoro-16-methylene-20-chloromethoxy-21-nor-1,4-pregnadiene-7β,11β,17α-triol-3,20-dione 17-propionate,
(3) 9α-fluoro-16-fluoromethylene-1,4-pregnadiene-7β,11β,17α,21-tetrol-3,20-dione 21-acetate.

(3)(a) Treat n-butyl 9α-fluoro-11β-hydroxy-16α,17α-isopropylidenedioxy-3,20-dioxo-1,4-pregnadien-21-oate with dry hydrogen chloride and DDQ in dioxane according to the procedure of Example 1A followed by treatment of the corresponding 1,4,6-pregnatriene derivative thereby produced in a manner similar to that described in Preparation 11A(1), (2) and (3) to obtain n-butyl 6β-propionyloxy-7β,11β-dihydroxy-9α-fluoro-16α,17α-isopropylidenedioxy-3,20-dioxo-1,4-pregnadien-21-oate.

(3) (b) Treat n-butyl 6β-propylidenedioxy-7β,11β-dihydroxy-9α-fluoro-16α,17α-isopropylidenedioxy-3,20-dioxo-1,4-pregnadien-21-oate (1 gm.) with zinc (1 gm.) and acetate acid (10 ml.) at room temperature for 1 hour. Filter the reaction mixture, pour the filtrate in water, and separate the resultant precipitate by filtration and air dry to obtain n-butyl 7β,11β-dihydroxy-9α-fluoro-16α,17α-isopropylidenedioxy-3,20-dioxo-1,4-pregnadien-21-oate.

B. 7α-Fluoro-9α-Halogeno-1,4-Pregnadiene-3,20-Diones

In a manner similar to that described in Example 8A, treat each of the 7β-hydroxy-1,4-pregnadienes prepared in Example 14A with fluoramine in methylene chloride at 0° C under an atmosphere of nitrogen. Isolate and purify each of the resultant products in a manner similar to that described to obtain, respectively, the 7α-fluoro derivative of each of the starting compounds of Example 14A(1), 14A(2) and 14(3).

c. 7α-Bromo-9α-Halogeno-1,4-Pregnadiene-3,20-Diones

In a manner similar to that described in Example 10A, treat each of the 7β-hydroxy-1,4-pregnadiene-3,20-diones prepared in Example 14A with fluoramine and lithium bromide in methylene chloride and isolate and purify each of the resultant products in the described manner to obtain, respectively, the 7α-bromo derivative of each of the starting compounds listed in Examples 14A(1), 14A(2) and 14A(3).

D. 7α-Chloro-9α-Halogeno-1,4-Pregnadiene-3,20-Diones

In a manner similar to that described in Example 10D, treat each of the 7β-hydroxy-1,4-pregnadiene-3,20-diones prepared in Example 14A with fluoramine and lithium chloride in methylene chloride and isolate and purify each of the resultant products in a manner similar to that described to obtain, respectively, the 7α-chloro derivative of each of the starting compounds listed in Examples 14A(1), 14A(2) and 14A(3).

E. 7α,9α,17α-Trihalogeno-1,4-Pregnadiene-3,20-Diones (1) 7α,9α-Difluoro-17α-Chloro-16α-Methyl-1,4-Pregnadiene-11β,21-Diol-3,20-Dione21-Acetate and the Corresponding 17α-Bromo Derivative At −78° C add anhydrous hydrogen fluoride (15 ml.) to a mixture of 7α,9α-difluoro-16α-methyl-1,4-pregnadiene-11β,21-diol-3,20-dione 21-acetate (5 gms.) and N-chlorosuccinimide (2 gms.) in tetramethylene sulfone (5 ml.). Allow the reaction mixture to stand at 3° C for 7 days, then pour with stirring into a mixture of equal parts of water, ice and 25% aqueous ammonium hydroxide (300 ml.). Isolate the resultant precipitate by filtration, wash the precipitate with water, and dissolve in methylene chloride. Wash the organic solution with 10% aqueous sodium sulfite, then water, dry over sodium sulfate and evaporate in vacuo. Chromatograph the resultant residue on silica gel eluting with chloroform:ethyl acetate (2:1). Combine the like eluates containing the desired compound as determined by thin layer chromatography and evaporate in vacuo to a residue comprising 7α,9α-difluoro-17α-chloro-16α-methyl-1,4-pregnadiene-11β,21-diol-3,20-dione 21-acetate.

In the above procedure, by substituting for N-chlorosuccinimide an equivalent quantity of N-bromosuccinimide, there is obtained the corresponding 17α-bromo compound, i.e., 7α,9α-difluoro-17α-bromo-16α-methyl-1,4-pregnadiene-11β,21-diol-3,20-dione 21-acetate.

(140

(2) In similar manner, treat 7α,9α-difluoro-16α-methyl-1,4-pregnadien-11β-ol-3,20,21-trione 21-ethylene ketal with either N-chlorosuccinimide or N-bromosuccinimide and hydrogen fluoride in tetramethylene sulfone in a manner similar to that described in Example 14E(1) to obtain either 7α,9α-difluoro-17α-chloro-16α-methyl-1,4-pregnadien-11β-ol-3,20,21-trione or 7α,9α-difluoro-17α-bromo-16α-methyl-1,4-pregnadien-11β-ol-3,20,21-trione, respectively. (3) In the procedure of Examples 14E(1) and 14E(2), by starting with the 7α-chloro or 7α-bromo analog corresponding to the 7α-fluoro-1,4-pregnadiene starting compound named therein, there is obtained either the 7α-chloro-17α-halogeno or 7α-bromo-17α-halogeno derivative corresponding to the 7α-fluoro-17α-halogeno products named therein, i.e. 7α,17α-dichloro-9α-fluoro-16α-methyl-1,4-pregnadiene-11β,21-diol-3,20-dione 21-acetate, 7α-bromo-9α-fluoro-17α-chloro-16α-methyl-1,4-pregnadiene-11β,21-diol-3,20-dione 21-acetate, 7α-chloro-9α-fluoro-17α-bromo-16α-methyl-1,4-pregnadiene-11β,21-diol-3,20-dione 21-acetate, 7α,17α-dibromo-9α-fluoro-16α-methyl-1,4-pregnadiene-11β,21-diol-3,20-dione 21-acetate, 7α,17α-dichloro-9α-fluoro-16α-methyl-1,4-pregnadien-11β-ol-3,20,21-trione, 7α-chloro-9α-fluoro-17α-bromo-16α-methyl-1,4-pregnadien-11β-ol-3,20,21-trione, 7α-bromo-9α-fluoro-17α-chloro-16α-methyl-1,4-pregnadien-11β-ol-3,20,21-trione, and 7α,17α-dibromo-9α-fluoro-16α-methyl-1,4-pregnadien-11β-ol-3,20,21-trione, respectively.

EXAMPLE 15

OTHER 7α,9α,11β-TRIHALOGENO-1,4-PREGNADIENE-3,20-DIONES

A. 7α,9α,11β-Trichloro-21-Fluoro-16-Methylene-1,4-Pregnadien-17α-OL-3,20-Dione 17-Propionate (1) 7αChloro-21-Fluoro-16-Methylene-1,4,9(11)-Pregnatriene-17α-Ol-3,20-Dione 17-Propionate In a manner similar to that described in Example 6A(1), treat 7α-chloro-21-fluoro-16-methylene-1,4-pregnadiene-11β,17αdiol-3,20-dione 17-propionate with methanesulfonyl chloride and sulfur dioxide in dimethylformamide and collidine. Isolate and purify the resultant product in a manner similar to that described to obtain 7α-chloro-21-fluoro-16-methylene-1,4,9(11)-pregnatrien-17α-ol-3,20-dione 17-propionate.

(2) In a manner similar to that described in Example 6B(1), treat the 7α-chloro-21-fluoro-1,4,9(11)-pregnatriene of Example 15A(1) with chlorine in chloroform and pyridine. Isolate and purify the resultant product in a manner similar to that to obtain 7α,9α,11β-trichloro-21-fluoro-16-methylene-1,4-pregnadien-17α-ol-3,20-dione 17-propionate.

B. 7α,9α,17α-Trichloro-11β-Fluoro-16α-Methyl-1,4-Pregnadien-21-Ol-3,20-dione 21-Pivalate (1) 7α-Chloro-16α-Methyl-1,4,9(11)-Pregnatrien-21-Ol-3,20-Dione 21-Pivalate In a manner similar to that described in Example 6A(1), treat 7α-chloro-16α-methyl-1,4-pregnadiene-11β,21-diol-3,20-dione 21-pivalate with methanesulfonyl chloride and sulfur dioxide in dimethylformamide and collidine to obtain 7α-chloro-16α-methyl-1,4,9(11)-pregnatrien-21ol-3,20-dione 21-pivalate.

(2) In a manner similar to that described in Example 14E(1), treat 7α-chloro-16α-methyl-1,4,9(11)-pregnatrien-21-ol-3,20-dione 21-pivalate with anhydrous hydrogen fluoride and N-chlorosuccinimide in tetramethylene sulfone. Isolate and purify the resultant product in a manner similar to that described to obtain 7α,9α,17α-trichloro-11β-fluoro-16α-methyl-1,4-pregnadien-21-ol-3,20-dione -21-pivalate.

C. Treat each of the following 7-unsubstituted-1,4-pregnadiene-3,20-diones with DDO and hydrogen chloride in a manner similar to that described in Preparation 1A, then react the resulting 1,4,6-pregnatriene-3,20-dione according to the procedures described in Preparation 11A followed by treatment of the resulting 7α-hydroxy derivative thereby obtained with either fluoramine according to the procedure of Example 8A or fluoramine together with lithium chloride according to the procedure of Example 10D or with fluoramine together with lithium bromide according to the procedure of Example 10A to obtain the corresponding 7α-fluoro- or 7α-chloro- or 7α-bromo-derivative, respectively, of each of the following starting compounds: n-butyl 9α-chloro-11β-fluoro-14α,17α-ethylidenedioxy-3,20-dioxo-1,4-pregnadiene-21-oate, methyl 9α,11β-dichloro-16α-methyl-17α-acetoxy-3,20-dioxo-1,4-pregnadiene-21-oate, n-butyl 11β-fluoro-9α-chloro-14α,17α-ethylidene-dioxy-3,20-dioxo-1,4-pregnadiene-21-oate, n-butyl 9α-chloro-11β-fluoro-14α,17α-ethylidenedioxy-3,20-dioxo-1,4-pregnadien-21-oate, n-butyl-9α-chloro-11α-fluoro-14α,17α-ethylidenedioxy-3,20-dione-1,4-pregnadien-21-pate, methyl 9α,11β-dichloro-16α-methyl-17α-acetoxy-3,20-dioxo-1,4-pregnadien-21-oate, methyl 9α,11β-dichloro-16α-methyl-17α-acetoxy-3,20-dioxo-1,4-pregnadien-21-oate, methyl 9α,11β-dichloro-16α-methyl-17α-acetoxy-3,20-dioxo-1,4-pregnadien-21-oate.

EXAMPLE 16

PREPARATION OF 17α-MONOESTERS

A. Via Malt Diastase (1) 7α-Bromo-16α-Methyl-1,4-Pregnadiene-11β,17α,21-Triol-3,20-Dione 17-Valerate To a suspension of diastase enzyme of malt (1.67 gms.) in ethanol (33.5 ml.) and water (167.5 ml.) add 7α-bromo-16α-methyl-1,4-pregnadiene-11β,17α,21-triol-3,20-dione 17-valerate 21-acetate (33.5 mg.). Stir the reaction mixture at room temperature for 3 days, then evaporate in vacuo at room temperature. Dissolve the resultant residue in ethyl acetate and water and filter the solution through a Celite pad washing with ethyl acetate. Separate the organic and aqueous layers, then extract the aqueous layer with ethyl acetate. Wash the combined organic extracts with water, dry over magnesium sulfate and evaporate in vacuo. Purify the resultant residue via thin layer chromatography utilizing as developing solvent chloroform:ethyl acetate (3:1). Remove the band containing the desired product as visualized under ultraviolet light. Elute with ethyl acetate and evaporate to a residue comprising 7α-bromo-16α-methyl; 1,4-pregnadiene-11α,17α,21-triol-3,20-dione 17-valerate. Purify by triturating with ether:hexane.

(2) In similar manner, treat each of 7α-chloro-16α-methyl-1,4-pregnadiene-11β,17α,21-triol-3,20-dione 17-valerate 21-acetate and 7α-chloro-16α-methyl-1,4-pregnadiene-11β,17α,21-triol-3,20-dione 17,21-dipropionate with the diastase enzyme of malt in aqueous ethanol according to the procedure of Example 16A(1) to obtain, respectively, 7α-chloro-16α-methyl-1,4pregnadiene-11β,17α,21-triol-3,20-dione 17-valerate and 7α-chloro-16α-methyl-1,4-pregnadiene-11β,17α,21-triol-3,20-dione 17-propionate.

(3) In similar manner, by treating any of the 7α-halogeno-21-acyloxy-1,4-pregnadiene derivatives of Examples 1-15 with the diastase enzyme of malt in aqueous ethanol in a manner similar to that described in Example 16A(1), there is obtained the corresponding 21-hydroxy derivative.

B. Via Acid Hydrolysis (1) 7α-Bromo-1,4-Pregnadiene-11β,17α,21-Triol-3,20-Dione 17-Benzoate To 7α-bromo-16α-methyl-1,4-pregnadiene-11β,17α,21-triol-3,20-dione 17-benzoate 21-acetate (0.44 gms.) in methanol (69 ml.) add 70% aqueous perchloric acid (1.76 ml.) and stir the reaction mixture for 4 hours. Bring the reaction mixture to neutrality with saturated aqueous sodium bicarbonate, remove the methanol evaporating in vacuo. Cool the aqueous reaction mixture and filter the resultant precipitate comprising a mixture of 7α-bromo-1,4-pregnadiene-11β, 17α,21-triol-3,20 -dione and the 17-monobenzoate and 21-monobenzoate esters thereof. Separate via thin layer chromatography on silica gel developing with ethyl acetate: chloroform (1:1), remove the band containing the desired 17-benzoate ester as visualized under ultraviolet light, elute with ethyl acetate and evaporate to a residue of 7α-bromo-1,4-pregnadiene-11β,17α,21-triol-3,20-dione 17-benzoate.

C. 7α-Halogeno-9α-Fluoro-1,4-Pregnadiene-11β,16α,1-7α,21-Tetrol-3,20-Dione 17-Hydrocarboncarboxylates (1) 7α-Chloro- and 7α-Bromo-9α-Fluoro-1,4-Pregnadiene-11β,16α,17α,21-Tetrol-3,20-Dione 17-Propionate (a) 9α-Fluoro-1,4,6-Pregnatriene-16α,17α,21-Triol-3,11,20-Trione 16,21-Diacetate 17-Lower alkanoate In a manner similar to that described in Preparation 5D, treat 9α-fluoro-1,4,6-pregnatriene-16α,17α,21-triol-3,11,20-trione-16,21-diacetate with trifluoroacetic anhydride, propionic acid and p-toluenesulfonic acid monohydrate and isolate the resultant product in a manner similar to that described to obtain 9α-fluoro-1,4,6-pregnatriene-16α,17α,21-triol-3,11,20-trione 16,21-diacetate 17-propionate.

In the above procedure, by substituting n-butyric acid for propionic acid, there is obtained 9α-fluoro-1,4,6-pregnatriene-16α,17α,21-triol-3,11,20-trione 16,21-diacetate 17-n-butyrate.

(b) 9α-Fluoro-1,4-Pregnadiene-7α,16α,17α-21-tetrol-3,11,20-Trione 16,21-Diacetate 17-Lower Alkanoate Subject each of the 16α,17α,21-alkanoyloxy-1,4,6-pregnatrienes prepared in Example 16C(1)(a) to a sequence of reactions similar to that described in Preparation 11A(1-4) to obtain, respectively, 9α-fluoro-1,4-pregnadiene-7β,16α, 17α, 21-tetrol-3,11,20-trione 16,21-diacetate 17-propionate and 9α-fluoro-1,4-pregnadiene-7β,16α,17α,21-tetrol-3,11,20-trione 16,21-diacetate 17-n-butyrate.

(c) 7α-Halogeno-9α-Fluoro-1,4-Pregnadiene-16α,1-7α,21-Triol-3,11,20-Trione 16,21-Diacetate 17-Alkanoate In a manner similar to that described in Example 8A, treat each of the 7β-hydroxy derivatives of Example 16C(1)(b) with fluoramine in methylene chloride to obtain, respectively, the 17-propionate and 17-n-butyrate of 7α,9α-difluoro-1,4-pregnadiene-16α,17α,21-triol-3,11,20-trione 16,21-diacetate.

In a manner similar to that described in Example 10A and 10C, treat each of the 7β-hydroxy pregnadiene compounds of Example 16C(1)(b) in methylene chloride with lithium bromide and fluoramine or with lithium chloride and fluoramine to obtain, respectively, the 17-propionate and 17-n-butyrate of 7α-bromo-9α-fluoro-1,4-pregnadiene-16α,17α,21-triol-3,11,20-trione 16,21-diacetate and of 7α-chloro-9α-fluoro-1,4-pregnadiene-16α,17α,21-triol-3,11,20-trione 16,21-diacetate.

(d) 7α-Halogeno-9α-Fluoro-1,4-Pregnadiene-11β,16α,17α,21-Tetrol-3,20-Dione 16,21-Diacetate 17-Alkanoate In a manner similar to that described in Example 1C and 2C, treat each of the products of Example 16C(1)(c) with sodium borohydride in tetrahydrofuran and methanol under an atmosphere of nitrogen, and isolate each of the resultant products in a manner similar to that described to obtain, respectively, 17-propionate and 17-n-butyrate of 7α,9α-difluoro-1,4-pregnadiene-11β,16α,17α,21-tetrol-3,20-dione 16,21-diacetate, the 17-propionate and the 17-n-butyrate ester of 7α-chloro-9α-fluoro-1,4-pregnadiene-11β,16α,17α,21-tetrol-3,20-dione 16,21-diacetate and the 17-propionate and 17-n-butyrate esters of 7α-bromo-9α-fluoro-1,4-pregnadiene-11β,16α,17α,21-tetrol-3,20-dione 16,21-diacetate.

(e) 7α-Halogeno-9α-Fluoro-1,4-Pregnadiene-11β,16α,17α,21-Tetrol-3,20-Dione 17-Alkanoate In a manner similar to that described in Example 16A, treat each of the products of Example 16C(1)(d) with the diastase enzyme of malt in aqueous ethanol and isolate and purify each of the resultant products in a manner similar to that described to obtain, respectively, the 17α-propionate and the 17α-n-butyrate of 7α,9α-difluoro-1,4-pregnadiene-11β,16α,17α,21-tetrol-3,20-dione and the 17-propionate and 17-n-butyrate of 7α-chloro-9α-fluoro-1,4-pregnadiene-11β,16α,17α,21-tetrol-3,20-dione and of 7α-bromo-9α-fluoro-1,4-pregnadiene-11β16α,17α,21-tetrol-3,20-dione.

(2) 7α-Chloro and 7α-Bromo-9α-Fluoro-1,4-Pregnadiene-11β,16α,17α,21-Tetrol-3,20-Dione 17-Benzoate (a) 9α-Fluoro-1,4,6-Pregnatriene-16α,17α,21-Triol-3,11,20-Trione 16,17-Methylorthobenzoate 21-Acetate In a manner similar to that described in Preparation 2C(1), treat 9α-fluoro-1,4,6-pregnatriene-16α,17α,21-triol-3,11,20-trione 21-acetate with trimethylorthobenzoate and pyridinium p-toluenesulfonate in dioxane and benzene and isolate the resultant product in the described manner to obtain 9α-fluoro-1,4,6-pregnatriene-16α,17α,21-triol-3,11,20-trione 16,17-methylorthobenzoate 21-acetate.

(b) 7α-Halogeno-9α-Fluoro-1,4-Pregnadiene-16α,1-7α,21-Triol-3,11,20-Trione 16,17-Methylorthobenzoate 21-Acetate In a manner similar to that described in Example 1B and 2B, treat the product of Example 16C(2)(a) with hydrogen chloride in tetrahydrofuran or with hydrogen bromide in glacial acetic acid and isolate each of the resultant products in a manner similar to that to obtain the 7α-chloro- and 7α-bromo- derivatives, respectively, of 9α-fluoro-1,4-pregnadiene-16α,17α,21-triol-3,11,20-trione 16,17-methylorthobenzoate 21-acetate.

(c) 7α-Halogeno-9α-Fluoro-1,4-Pregnadiene-11β,16α,17α,21-Tetrol-3,20-Dione 17-Benzoate 21-Acetate In a manner similar to that described in Preparation 2A(2), treat the 16,17-methylorthobenzoate derivatives of Example 16C(2)(b) with aqueous acetic acid, then isolate each of the resultant products in a manner similar to that to obtain, respectively the 17-propionate and 17-n-butyrate of 7α,9α-difluoro-1,4-pregnadiene-11β,16α,17α,21-tetrol-3,20-dione and the 17-propionate and 17-n-butyrate of 7α-chloro and 7α-bromo derivatives of 9α-fluoro-1,4-pregnadiene-11β,16α,17α,21-tetrol-3,20-dione 17-benzoate 21-acetate:

(d) 7α-Halogeno-9α-Fluoro-1,4-Pregnadiene-11β,16α,17α,21-Tetrol-3,20-Dione 17-Benzoate In a manner similar to that described in Example 16A, treat each of the products of Example 16C(2) (c) with diastase enzyme of malt in aqueous ethanol and isolate each of the resultant products in a manner similar to that to obtain the 7α-chloro- and 7α-bromo- derivaties of 9α-fluoro-1,4-pregnadiene-11β,16α,17α,21-tetrol-3,20-dione 17-benzoate.

EXAMPLE 17

7α-HALOGENO-1,4-PREGNADIENE-17α,21-DIOL-3,20-DIONE 17-HYDROCARBONCARBOXYLATE 21-RETINOATES

A. 7α-Chloro-16α-Methyl-1,4-Pregnadiene-11β,17α,21-Triol-3,20-Dione 17-Propionate 21-Retinoate To a suspension of 7α-chloro-16α-methyl-1,4-pregnadiene-11β,17α,21-triol-3,20-dione 17-propionate (464 mg., 1 mmol), in methylene chloride (50 ml.) under nitrogen and in the dark, add retinoic acid (300 mg., 1 mmol) and 1-cyclohexyl-3-(2-morpholinoethyl)carbodiimide metho-p-toluenesulfonate (424 mg., 1 mmol). Stir at room temperature for 17 hours, then add an additional mmol of retinoic acid and an additional mmol of the diimide, and continue stirring the reaction mixture for an additional 24 hours. Extract the reaction mixture sequentially with 2% hydrochloric acid, water, 5% aqueous sodium bicarbonate and again with water. Dry over sodium sulfate and evaporate in vacuo. Chromatograph the resultant residue on silica gel GF thick layer plates eluting with ethyl acetate:chloroform (1:2). Remove the steroidal retinoate band from the thick layer plate, extract with ethyl acetate and evaporate in vacuo in a residue comprising 7α-chloro-16α-methyl-1,4-pregnadiene-11β,17α,21-triol-3,20-dione 17-propionate 21-retinoate. Further purify by crystallization from ether:petroleum ether.

B. Similarly, by treating any 21-hydroxy-7α-halogeno-1,4-pregnadiene-3,20-dione of this invention prepared as described in Example 17A, there is obtained the corresponding 21-retinoate thereof.

EXAMPLE 18

HYDROLYSIS OF 17α- AND/OR 21-ESTERS

A. 7α-Chloro-16α-Methyl-1,4-Pregnadiene-11β,17α,21-Triol-3,20-Dione

To a solution of 7α-chloro-16α-methyl-1,4-pregnadiene-11β,17α,21-triol-3,20-dione 17,21-dipropionate (3.5 gms.) in methanol (300 ml.) and saturated aqueous sodium bicarbonate solution (30 ml.) and allow to stand at room temperature for 18 hours. Pour into water, filter the resultant precipitate, wash the precipitate with water until neutral, then air dry. Crystallize the dried precipitate from acetone/hexane to give 7α-chloro-16α-methyl-1,4-pregnadiene-11β,17α,21-triol-3,20-dione, yield 1.3 gms., m.p. 176°–179° C, $[\alpha]^{26}$ + 47.5 (dmf), $\lambda_{max}^{MeOH}$ 242 nm ($\epsilon$=15,500).

B. 7α-Bromo-1,4-Pregnadiene-11β,17α,21-Triol-3,20-Dione

To a solution of 1,4,6-pregnatriene-11β,17α,21-triol-3,20-dione 21-acetate (5 gms.) in glacial acetic acid (62 ml.) add dry hydrogen bromide (37.5 gms.) and allow the reaction mixture to stand at 0°–5° C for 45 minutes. Pour the reaction mixture into water, separate the resultant precipitte by filtration, wash the precipitate with water and air dry to obtain 7α-bromo-1,4-pregnadiene-11β,17α,21-triol-3,20-dione 21-acetate.

Dissolve the foregoing product in methanol (525 ml.), add 70% aqueous perchloric acid (13.2 ml.) and stir the reaction mixture at room temperature for 18 hours. Add water, then add saturated aqueous sodium bicarbonate until the solution is neutral, then evaporate the reaction mixture until the methanol is removed. Extract the aqueous reaction mixture with ethyl acetate, wash the combined ethyl acetate extracts with water, dry the ethyl acetate over sodium sulfate and evaporate. Crystallize the resultant residue from acetone to obtain 7α-bromo-1,4-pregnadiene-11β,17α,21-triol-3,20-dione, yield 0.3 gms., m.p. < 320° C, $[\alpha]_D^{26}$ + 48.2 (dmf), $\lambda_{max}^{MeOH}$ 241 nm (ε=15,100).

EXAMPLE 19

7α-IODO-9α-HALOGENO-16β-METHYL-1,4-PREGNADIENE-11β,17α,21-TRIOL-3,20-DIONE 17,21-DIPROPIONATE

A. 7α-Iodo-9α-Fluoro-16β-Methyl-1,4-Pregnadiene-11β,17α,21-Triol-3,20-Dione 17,21-Dipropionate (1) To a solution of dry hydrogen iodide (0.4 gms.) in glacial acetic acid (1.5 ml.) at room temperature, protected from light, add a solution of 9α-fluoro-16β-methyl-1,4,6-pregnatriene-11β,17α,21-triol-3,20-dione 17,21-dipropionate (0.05 gms.) in glacial acetic acid (0.5 ml.). Stir the reaction mixture (protected from light) at room temperature for 30 minutes, then add 5% of sodium thiosulfate solution (20 ml.). Extract the mixture with methylene chloride (two 50 ml. portions), wash the combined organic extracts twice with water, dry over anhydrous sodium sulfate and evaporate at room temperature in vacuo. Purify the resultant residue on silica gel via thick layer technique developing with ethyl acetate/chloroform (1:9). Scrape off the more polar band as shown under ultraviolet light, wash the silica gel with ethyl acetate, then evaporate the combined ethyl acetate washings in vacuo and crystallize the resultant residue from ether to obtain 7α-iodo-9α-fluoro-16β-methyl-1,4-pregnadiene-11β,17α,21-triol-3,20-dione 17,21-dipropionate, yield 16 mg. (39%); m.p. 145° C (decomp.); nmr (dmso-d$_6$) δ 0.95 ($C_{13}$-$CH_3$, s), 1.28 ($C_{16}$-$CH_3$, d J 6Hz), 1.55 ($C_{10}$-$CH_3$, s), 4.20 (11α-H, mult.), 4.59 ($C_{21}$-H, dd J 21, 17Hz), 4.70 (7β-H, mult.), 5.99 ($C_4$-H, s), 6.20 ($C_2$-H, dd J 10, 2Hz), 7.25 ($C_1$-H, d J 10Hz).

Alternatively, the compound of this example is prepared according to Examples 19A(2) and 19A(3) hereinbelow.

(2) 7α-Iodo-9α-Fluoro-16β-Methyl-1,4-Pregnadiene-17α,21-Diol-3,11,20-Trione 17,21-Dipropionate In a manner similar to that described in Example 19A(1), treat 9α-fluoro-16β-methyl-1,4,6-pregnatriene-17α,21-diol-3,11,20-trione 17,21-dipropionate (100 mg.) in glacial acetic acid (1 ml.) with dry hydrogen iodide (0.8 gms.) in acetic acid (3 ml.). Isolate and purify the resultant product in a manner similar to that described in Example 19A(1) to obtain 7α-iodo-9α-fluoro-16β-methyl-1,4-pregnadiene-17α,21-diol-3,11,20-trione 17,21-dipropionate, yield =80 mg., (64% theory). Further purify by crystallization from ether. (m.p. 106° C (decomp.))

(3) In a manner similar to that described in Example 3C(1), treat 7α-iodo-9α-fluoro-16β-methyl-1,4-pregnadiene-17α,21-diol-3,11,20-trione 17,21-dipropionate under an atmosphere of nitrogen with sodium borohydride at 0° C in a precooled solution of tetrahydrofuran and methanol. Isolate and purify the resultant product in a manner similar to that described to obtain 7α-iodo-9α-fluoro-16β-methyl-1,4-pregnadiene-11β,17α,21-triol-3,20-dione 17,21-dipropionate.

B. 7α-Iodo-9α-Chloro-16β-Methyl-1,4-Pregnadiene-11β,17α,21-Triol-3,20-Dione 17,21-Dipropionate (1) 7α-Iodo-9α-Chloro-16β-Methyl-1,4,6-Pregnatriene-11β,17α,21-Triol-3,20-Dione 17,21-Dipropionate In a manner similar to that described in Example 19A(1), treat 9α-chloro-16β-methyl-1,4,6-pregnatriene-11β,17α,21-triol-3,20-dione 17,21-dipropionate with hydrogen iodide in glacial acetic acid and isolate and purify the resultant product in a manner similar to that described to obtain 7α-iodo-9α-chloro-16β-methyl-1,4,6-pregnatriene-11β,17α,21-triol-3,20-dione 17,21-dipropionate, yield = 15%.

(2) Alternatively, the compound of this example is made by treating 9α-chloro-16β-methyl-1,4,6-pregnatriene-17α,21-diol-3,11,20-trione 17,21-dipropionate with hydrogen iodide in acetic acid according to the procedure of Example 19A(2) followed by reduction of the resulting 7α-iodo-9α-chloro-16β-methyl-1,4-pregnadiene-17α,21-diol-3,11,20-trione 17,21-dipropionate with sodium borohydride in methanol/tetrahydrofuran according to the procedure of Example 19A(3).

C. 7α-Iodo-9α-Bromo-16β-Methyl-1,4-Pregnadiene-11β,17α,21-Triol-3,20-Dione 17,21-Dipropionate Treat 9α-bromo-16β-methyl-1,4,6-pregnatriene-17α,21-diol-3,11,20-trione 17,21-dipropionate with hydrogen iodide in acetic acid according to the procedure of Example 19A(2) followed by treatment of the resulting 7α-iodo-9α-bromo-16β-methyl-1,4-pregnadiene-17α,21-diol-3,11,20-trione 17,21-dipropionate with sodium borohydride in methanol/tetrahydrofuran according to the procedure of Example 19A(3) to obtain 7α-iodo-9α-bromo-16β-methyl-1,4-pregnadiene-11β,17α,21-triol-3,20-dione 17,21-dipropionate.

EXAMPLE 20

7α-BROMO-9α-HALOGENO-16β-METHYL-1,4-PREGNADIENE-11β,17α,21-TRIOL-3,20-DIONE 17,21-DIPROPIONATE

A. 7α-Bromo-9α-Fluoro-16β-Methyl-1,4-Pregnadiene-11β,17α,21-Triol-3,20-Dione 17,21-Dipropionate (1) 7α-Bromo-9α-Fluoro-16β-Methyl-1,4-Pregnadiene-17α,21-Diol-3,11,20-Trione 17,21-Dipropionate To a solution of 9α-fluoro-16β-methyl-1,4,6-pregnatriene-17α,21-diol-3,11,20-trione 17,21-dipropionate (0.5 gms.) in glacial acetic acid (1 ml.), add a solution of dry hydrogen bromide in glacial acetic acid (48% w/w, 5 ml.). Stir at 5° C for one hour, then pour into ice water (300 ml.). Separate the resultant precipitate by filtration, wash thoroughly with water and air dry at room temperature. Further purify the resultant precipitate on thick layer silica gel plates developing with ethyl acetate/chloroform (1:5). Scrape off the band containing the desired compound as shown under ultraviolet light and elute the compound from the silica gel with ethyl acetate. Evaporate the combined ethyl acetate eluates to a residue comprising 7α-bromo-9α-fluoro-16β-methyl-1,4-pregnadiene-17α,21-diol-3,11,20-trione 17,21-dipropionate, yield = 60% theory, m.p. 115° C (decomp.).

(2) In a manner similar to that described in Example 19A(3), treat the 7α-bromo-9α-fluoro-16β-methyl-11-oxo compound of Example 20A(1) with sodium borohydride in methanol/tetrahydrofuran to obtain 7α-bromo-9α-fluoro-16β-methyl-1,4-pregnadiene-17α,21-diol-3,11,20-trione 17,21-dipropionate.

7α-Bromo-9α-Chloro-16β-Methyl-1,4-Pregnadiene-11β,17α,21-Triol-3,20-Dione 17,21-Dipropionate Treat 9α-chloro-16β-methyl-1,4,6-pregnatriene-17α,21-diol-3,11,21-trione 17,21-dipropionate with hydrogen bromide in acetic acid in a manner similar to that described in Example 20A(1) followed by treatment of the resulting 7α-bromo-9α-chloro-16β-methyl- 1,4-pregnadiene-17α,21-diol-3,11,20-trione 17,21-dipropionate with sodium borohydride in methanol/tetrahydrofuran according to the procedure of Example 19A(3) to obtain 7α-bromo-9α-chloro-16β-methyl-1,4-pregnadiene-11β,17α,21-triol-3,20-dione 17,21-dipropionate.

We claim:
1. A 3,20-dioxo-7-halogeno-1,4-pregnadiene of the following formula:

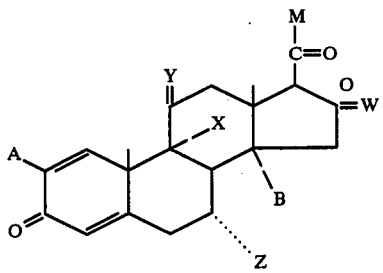

wherein A is hydrogen, and provided Y is (H,βOH), chlorine, fluorine or methyl;
B is hydrogen or, together with Q, is a 14α,17α-alkylideneoxy derivative;
X is a member selected from the group consisting of hydrogen having an atomic weight less than 100;
Y is a member selected from the group consisting of (H,H) provided X is hydrogen, oxygen, (H,βOH), (H,βOCOH); and (H,β-halogen) provided X is chlorine or bromine, said β-halogen having an atomic weight of less than 100 and being at least as electronegative as X;
Z is fluorine, chlorine, bromine and iodine;
Q is a member selected from the group consisting of hydrogen provided W is a member selected from the group consisting of (H,H) and (H, lower akyl); chlorine; bromine; and OV wherein V is a member selected from the group consisting of hydrogen and an acyl radical of a hydrocarboncarboxylic acid having up to 12 carbon atoms or of benzoic acid substituted by a halogen or methoxy group;
W is a member selected from the group consisting of (H,H); (H, lower alkyl); (H,α-OV₁) wherein V₁ is a member selected from the group consisting of hydrogen and an acyl radical of an acid selected from the group consisting of a hydrocarbonacarboxylic acid having up to 12 carbon atoms, benzoic acid substituted by a halogen or methoxy group, retinoic acid, and isonicotinic acid; =CHT wherein T is a member selected from the group consisting of hydrogen, lower alkyl, fluorine and chlorine, and
W and Q taken together is a member selected from the group consisting of 16α,17α-lower alkylidenedioxy; 16α,17α-cycloalkylidenedioxy; the grouping

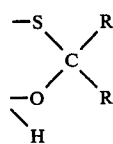

wherein R is lower alkyl; and the grouping

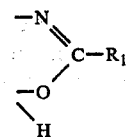

wherein R₁ is lower alkyl or phenyl;
M is a member selected from the group consisting of —OR₂ when Q is O-acyl, R₂ being lower alkyl or halogeno lower alkyl; —CHO, acetals, hemiacetals and acylals thereof; —COOR₃ wherein R₃ is an alkyl having up to 12 carbon atoms; —CH₂G wherein G is a member selected from the group consisting of hydrogen, halogen having an atomic weight of less than 100, OV₂ wherein V₂ is a member selected from the group consisting of hydrogen and an acyl radical of an acid selected from the group consisting of a hydrocarboncarboxylic acid having up to 12 carbon atoms, benzoic acid substituted by a halogen or methoxy group, retinoic acid, isonicotinic acid, phosphoric acid and mono- and dialkali, and alkaline earth metals salts thereof; and OV₂ together with OV is a member selected from the group consisting of alkylidene dioxy and alkylorthoalkanoate;
when W is hydrogen, the D-homo analogs thereof.
2. A compound of claim 1 wherein Z is chlorine or bromine.
3. A compound of claim 2 wherein X is hydrogen and Y is (H,βOH).
4. A 7α-Z compound of claim 1 wherein M is CH₂OV₂, Q is OV and A and B are hydrogen.
5. A compound of claim 4 wherein X is hydrogen, Y is (H,βOH), W is (H,CH₃) or =CH₂, and Z is chloro or bromo, said compound having the following formula:

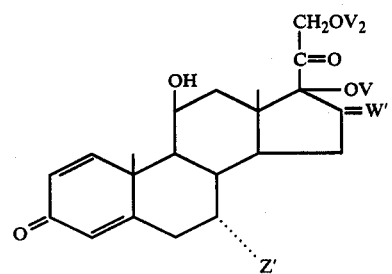

wherein Z' is chlorine or bromine;
W' is (H,CH₃) or =CH₂;
V and V₂ are each hydrogen or an acyl radical of a hydrocarboncarboxylic acid having up to 12 carbon atoms.
6. A compound of claim 5 wherein V and V₂ are acyl radicals of hydrocarboncarboxylic acids having up to 8 carbon atoms.
7. A compound of claim 6 wherein V is propionyl.
8. A compound of claim 6 wherein V is n-butyryl.
9. A compound of claim 6 wherein V is benzoyl.
10. A compound of claim 5 wherein W is (H,α—CH₃) and V and V₂ are acid residues of hydrocarboncarboxylic acids having up to 8 carbon atoms.
11. A compound of claim 10 wherein V is propionyl.
12. A compound of claim 10 wherein V and V₂ are each propionyl and Z' is chlorine, said compound being 7α-chloro-16α-methyl-1,4-pregnadiene-11β,17α,21-triol-3,20-dione 17,21-dipropionate.

13. A compound of claim 10 wherein V and V₂ are each propionyl and Z' is bromine, said compound being 7α-bromo-16α-methyl-1,4-pregnadiene-11β,17α,21-triol-3,20-dione 17,21-dipropionate.

14. A compound of claim 10 wherein V is benzoyl.

15. A compound of claim 10 wherein V is benzoyl, V₂ is acetyl and Z' is bromine, said compound being 7α-bromo-16α-methyl-1,4-pregnadiene-11β,17α,21-triol-3,20-dione 17-benzoate 21-acetate.

16. A compound of claim 5 wherein W is =CH₂, V and V₂ are each propionyl and Z' is chlorine, said compound being 7α-chloro-16-methylene-1,4-pregnadiene-11β,17α,21-triol-3,20-dione 17,21-dipropionate.

17. A compound of claim 1 wherein X, Y and Z are chlorine, W is (H,α-CH₃), V and V₂ are propionyl, said compound being 7α,9α,11β-trichloro-16α-methyl-1,4-pregnadiene-17α,21-diol-3,20-dione 17,21-dipropionate.

18. A compound of claim 4 wherein X is hydrogen, Y is oxygen, and W is (H,CH₃) or =CH₂, said compound having the following formula:

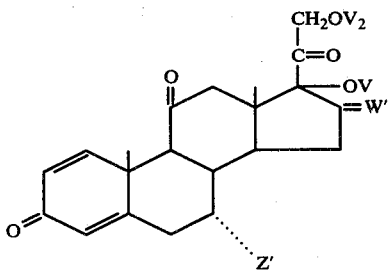

wherein Z' is chlorine or bromine;
W' is (H,CH₃) or =CH₂;
V and V₂ are each hydrogen or an acyl radical of a hydrocarboncarboxylic acid having up to 12 carbon atoms.

19. A pharmaceutical composition for use in the treatment of inflammation, which comprises an effective amount of a 3,20-dioxo-7α-halogeno-1,4-pregnadiene of claim 1 together with a non-toxic, pharmaceutically acceptable carrier.

20. A pharmaceutical composition of claim 19 for use in the topical treatment of inflammation, which comprises an effective amount of a 3,20-dioxo-7α-halogeno-1,4-pregnadiene of claim 5,
together with a non-toxic, pharmaceutically acceptable carrier.

21. A pharmaceutical composition of claim 20 comprising an effective amount of 7α-Z'-16α-methyl-1,4-pregnadiene-11β,17α,21-triol-3,20-dione 17-propionate 21-lower alkanoate, Z' being chlorine or bromine, together with a non-toxic, pharmaceutically acceptable carrier.

22. A pharmaceutical composition of claim 20 comprising an effective amount of 7α-Z'-16α-methyl-1,4-pregnadiene-11β,17α,21-triol-3,20-dione 17-benzoate 21-lower alkanoate, Z' being chlorine or bromine, together with a non-toxic, pharmaceutically acceptable carrier.

23. The method of treating an inflammatory condition in a warm-blooded animal responsive to treatment with anti-inflammatory agents which comprises administering to said animal a non-toxic, anti-inflammatory effective amount of a 3,20-dioxo-7α-halogeno-1,4-pregnadiene of claim 1 together with a non-toxic, pharmaceutically acceptable carrier.

24. The method according to claim 23 for the treatment of a topical inflammatory condition which comprises applying to the inflamed area in a concentration effective for the topical treatment of inflammation, a 3,20-dioxo-7α-halogeno-1,4-pregnadiene of claim 5, together with a non-toxic, pharmaceutically acceptable carrier.

25. The method of claim 24 wherein said 7α-halogeno-3,20-dioxo-1,4-pregnadiene is 7α-chloro-16α-methyl-1,4-pregnadiene-11β,17α,21-triol-3,20-dione 17,21-dipropionate.

26. The method according to claim 24 wherein said 7α-halogeno-3,20-dioxo-1,4-pregnadiene is 7α-bromo-16α-methyl-1,4-pregnadiene-11β,17α,21-triol-3,20-dione 17-benzoate 21-acetate.

27. The method according to claim 24 wherein said 7α-halogeno-3,20-dioxo-1,4-pregnadiene is 7α-bromo-16α-methyl-1,4-pregnadiene-11β,17α,21-triol-3,20-dione 17,21-dipropionate.

28. A compound of claim 1 wherein A, B and X are hydrogen, Y is (H,βOH); W is (H,α—CH₃); Q is benzoyloxy; M is —CH₂OCOCH₃, and Z is fluorine, said compound being 7α-fluoro-16α-methyl-1,4-pregnadiene-11β,17α,21-triol-3,20-dione 17-benzoate 21-acetate.

29. A compound of claim 1 wherein A, B and X are hydrogen; Y is (H,βOH); Q and W together are isopropylidenedioxy; M is —CH₂OCOCH₃, and Z is bromine, said compound being 7α-bromo-16α,17α-isopropylidenedioxy-1,4-pregnadiene-11β,21-diol-3,20-dione 21-acetate.

* * * * *

UNITED STATES PATENT AND TRADEMARK OFFICE
CERTIFICATE OF CORRECTION

PATENT NO. : 4,124,707

DATED : November 7, 1978

INVENTOR(S) : Michael J. Green et al

It is certified that error appears in the above-identified patent and that said Letters Patent are hereby corrected as shown below:

Column 2, lines 5-10, Formula I, " 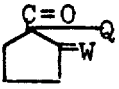 " should read

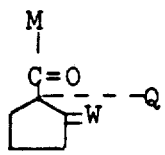 ---; lines 53-59, " 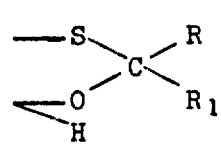 R " should read

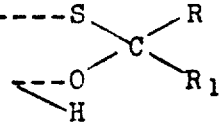 ---; lines 61-64, " 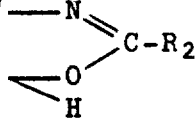 " should read

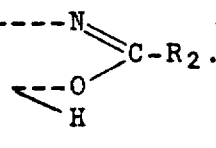. Column 4, lines 32-37, " 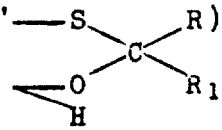 )," should read

UNITED STATES PATENT AND TRADEMARK OFFICE
CERTIFICATE OF CORRECTION

PATENT NO. : 4,124,707

DATED : November 7, 1978

INVENTOR(S) : Michael J. Green et al

It is certified that error appears in the above-identified patent and that said Letters Patent are hereby corrected as shown below:

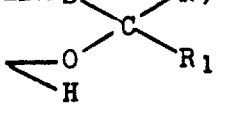 

Column 6, line 46, "11β,21-triol-" should read ---11β,17α,21-triol---. Column 7, line 7, "-11α,17α,21-" should read ---11β,17α,21---; line 10, "-11α,17α,21-" should read ---11β,17α, 21---; line 15, "the 16α-" should read ---the 16β---; line 22, "-11α," should read ---11β,---. Column 8, lines 1-7,

UNITED STATES PATENT AND TRADEMARK OFFICE
CERTIFICATE OF CORRECTION

PATENT NO. : 4,124,707

DATED : November 7, 1978

INVENTOR(S) : Michael J. Green et al

It is certified that error appears in the above-identified patent and that said Letters Patent are hereby corrected as shown below:

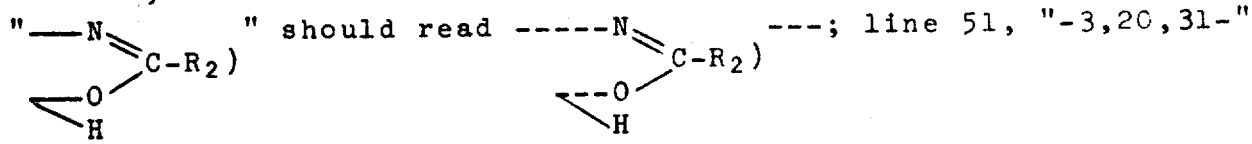

should read ---3,20,21---; line 53, "-9α9α-fluoro-16α-methyl-2,21-" should read ---9α-fluoro-16α-methyl-21,21---; line 56, "-methyl-,4-" should read ---methyl-1,4---; lines 61 and 62, "-p-homo-1,4-pregnadiene-11β,17α,21-triol-3,2-" should read ---D-homo-1,4-pregnadiene-11β,17α,21-triol-3,20---. Column 9, line 5, "-2-acetate," should read ---21-acetate---; line 10, "ae more" should read ---are more---; line 18, Formula III,

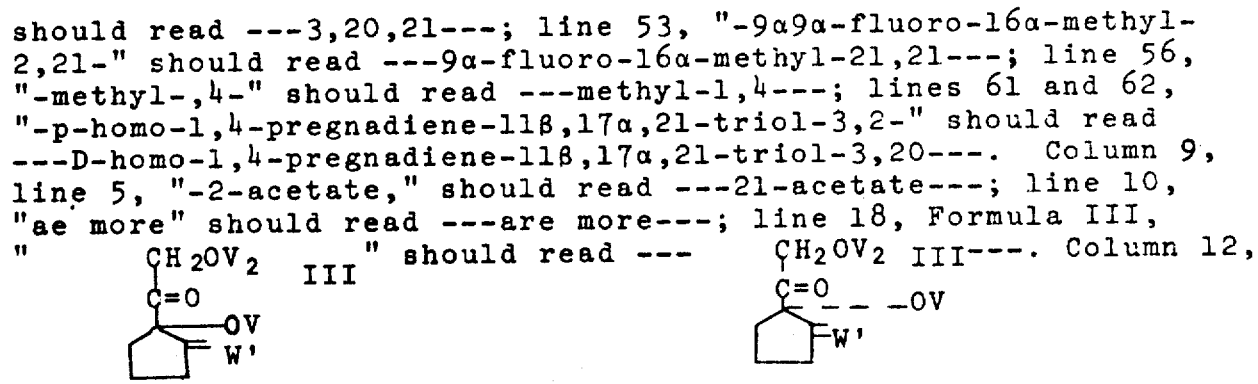

line 1, "-7α-chloro-9α-halogen-" should read ---7α-chloro-9α-halogeno---. Column 13, line 2, "a 7α-halogen-" should read ---a 7α-halogeno---; lines 8 and 9, "(e.g. 7α,9α,11β-trichloro

UNITED STATES PATENT AND TRADEMARK OFFICE
CERTIFICATE OF CORRECTION

PATENT NO. : 4,124,707
DATED : November 7, 1978
INVENTOR(S) : Michael J. Green et al It is certified that error appears in the above-identified patent and that said Letters Patent are hereby corrected as shown below:

derivative (e.g. 7α,9α,11β-trichloro-16α-methyl,1,4-pregnadiene-" should read ---(e.g. 7α,9α,11β-trichloro-16α-methyl-1,4-pregnadiene---.  Column 14, lines 21 and 22, "-17α-hydroxy-17α-monoesters" should read ---17α-monoesters---; line 55, "formed by be" should read ---formed may be---.  Column 15, line 13, "-7α-halogen-" should read ---7α-halogeno---.  Column 25, line 58, "-6β-bromo-16β-bromo-16α-methyl-" should read ---6β-bromo-16α-methyl---.  Column 27, line 17, "-17m21-" should read ---17,21---; line 21, "-16α-,etju;-" should read ---16α-methyl---; line 24, "-11ε,17α-" should read ---11β,17α---.  Column 38, line 35, "B. 7α,11β-" should read ---B. 7α,9α,11β---; line 61, "-3,20-diene-" should read ---3,20-dione---.  Column 39, line 53, "-16αα-- should read ---16α---.  Column 40, line 39, "on this layer" should read ---on thin layer---.  Column 41, line 21, "an vacuo at" should read ---in vacuo at---; line 44, "$[\alpha]^{26}$ +" should read $[\alpha]_D^{26}$ +---; line 59, "acetic acetic" should read ---acetic---.  Column 42, lines 32 and 33, "and 9α-fluoro-7β-hydroxy-" should read ---and 9α-bromo analogs of the 9α-fluoro-7β-hydroxy---; line 66, ";$[\alpha]^{26}$ +" should read ---; $[\alpha]_D^{26}$ +---.

UNITED STATES PATENT AND TRADEMARK OFFICE
CERTIFICATE OF CORRECTION

PATENT NO. : 4,124,707

DATED : November 7, 1978

INVENTOR(S) : Michael J. Green et al

It is certified that error appears in the above-identified patent and that said Letters Patent are hereby corrected as shown below:

Column 44, line 3, "-17-n-butyrate-n-butyrate and 17-benzoate-diol-" should read ---17-n-butyrate and the 17-benzoate---; lines 6 and 7, "i.e. the 17-n-benzoate of" should read ---i.e. the 17-n-butyrate and the 17-benzoate of---. Column 45, line 43, "-nadiene$[$17,16α-d$]$" should read ---nadieno$[$17,16α-d$]$---. Column 47, line 49, "and DDO" should read ---and DDQ---. Column 48, line 56, "acetate acid" should read ---acetic acid---. Column 50, line 60, "with DDO" should read ---with DDQ---; line 65, "-7α-" should read ---7β---. Column 51, line 12, "-9α-chloro-11α-" should read ---9α-chloro-11β---; line 13, "-21-pate," should read ---21-oate,---; line 42, "-methyl; 1,4-pregnadiene-11α,17α,21-" should read ---methyl-1,4-pregnadiene-11β,17α,21---.

Column 54, line 50, "$[α]^{26}$ +" should read ---$[α]^{26}_D$ +---.

Column 55, line 5, "m.p. $<$ 320°C," should read ---m.p. $>$ 320°C,---;

line 65, "-3,11,21-" should read ---3,11,20---. Column 57, lines 11-17, " 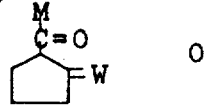 O " should read --- 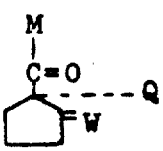 Q ---; line 28, "hydrogen having" should

UNITED STATES PATENT AND TRADEMARK OFFICE
CERTIFICATE OF CORRECTION

PATENT NO. : 4,124,707
DATED : November 7, 1978
INVENTOR(S) : Michael J. Green et al It is certified that error appears in the above-identified patent and that said Letters Patent are hereby corrected as shown below:

read ---hydrogen and halogen having---; lines 61-65, 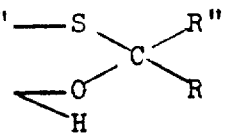

should read 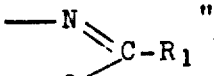. Column 58, lines 1-7, 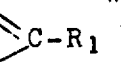

should read ; lines 39-44, 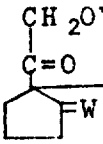 should read

--- 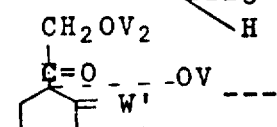 ---. Column 59, lines 22-29, 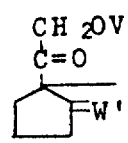 should read --- 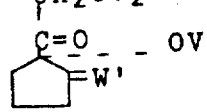 ---.

Signed and Sealed this

Fourth Day of December 1979

[SEAL]

Attest:

SIDNEY A. DIAMOND

Attesting Officer    Commissioner of Patents and Trademarks